US008426432B2

(12) United States Patent
Anderson et al.

(10) Patent No.: US 8,426,432 B2
(45) Date of Patent: Apr. 23, 2013

(54) INHIBITORS OF DIHYDROFOLATE REDUCTASE WITH ANTIBACTERIAL ANTIPROTOZOAL, ANTIFUNGAL AND ANTICANCER PROPERTIES

(75) Inventors: Amy C. Anderson, Storrs, CT (US); Dennis L. Wright, Storrs, CT (US); Phillip M. Pelphrey, Williamsville, NY (US); Tammy M. Joska, Hartford, VT (US); Erin S. D. Bolstad, Vernon, CT (US); David B. Bolstad, Vernon, CT (US); Veljko Popov, Hanover, NH (US)

(73) Assignee: University of Connecticut, Farmington, CT (US)

( * ) Notice: Subject to any disclaimer, the term of this patent is extended or adjusted under 35 U.S.C. 154(b) by 1206 days.

(21) Appl. No.: 12/133,099

(22) Filed: Jun. 4, 2008

(65) Prior Publication Data
US 2009/0105287 A1   Apr. 23, 2009

Related U.S. Application Data

(60) Provisional application No. 60/941,828, filed on Jun. 4, 2007.

(51) Int. Cl.
*A01N 43/54* (2006.01)
*A61K 31/505* (2006.01)
*C07D 239/02* (2006.01)

(52) U.S. Cl.
USPC .......................................... 514/275; 544/323

(58) Field of Classification Search .................. None
See application file for complete search history.

(56) References Cited

U.S. PATENT DOCUMENTS
5,622,954 A * 4/1997 Henrie et al. ............ 514/256

FOREIGN PATENT DOCUMENTS
WO    WO 98/20878    *  5/1998
WO    WO-9820878       5/1998
WO    2009025919 A3    2/2009

OTHER PUBLICATIONS

Anderson, et. al., Proteins: Structure, Function, and Bioinformatics 66:375-387 (2007).*
Anderson, et. al., Journal of Medicinal Chemistry (2007), 50(5), 940-950.*
Patani, et. al., Chem. Rev. 1996, 96, 3147-3176.*
Pelphrey, P. M. et al., "Highly efficient ligands for dihydrofolate reductase from *Cryptosporidium hominis* and *Toxoplasma gondii* inspired by structural analysis", *J. Med. Chem; 50* Mar. 8, 2007, 940-950.
Wright, et al., "Antifolate agents: a patent review (2006-2010)", Expert Opinion, 2011, 1-16.

* cited by examiner

*Primary Examiner* — Jeffrey Murray
(74) *Attorney, Agent, or Firm* — Porter Wright Morris & Arthur

(57) ABSTRACT

The compositions and methods described herein discloses the design, synthesis and testing of compounds that act as inhibitors of DHFR. The basic scaffold of these inhibitors includes a 2,4-diaminopyrimidine ring with a propargyl linker to another substituted aryl, bicyclo or heteroaryl ring. These DHFR inhibitors are potent and selective for many different pathogenic organisms, including the DHFR enzyme from bacteria such as *Bacillus anthracis* and methicillin-resistant *Staphylococcus aureus*, fungi such as *Candida glabrata*, *Candida albicans* and *Cryptococcus neoformans* and protozoa such as *Cryptosporidium hominis* and *Toxoplasma gondii*. These compounds and other similar compounds are also potent against the mammalian enzyme and may be useful as anti-cancer therapeutics.

17 Claims, 12 Drawing Sheets

Figure 2:
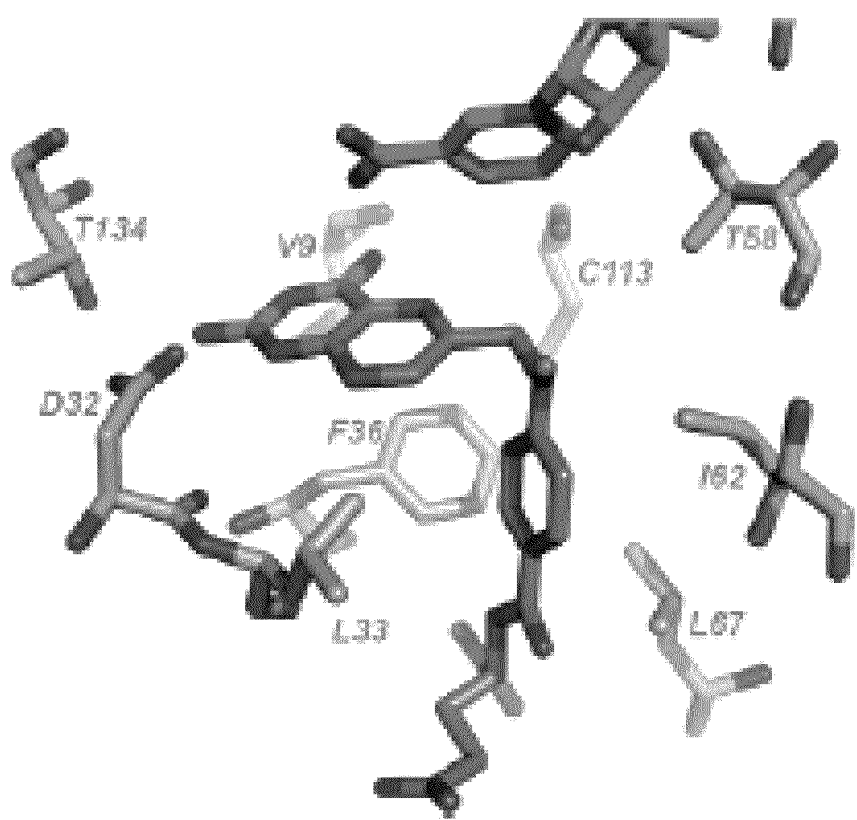
Figures 3A, 3B:
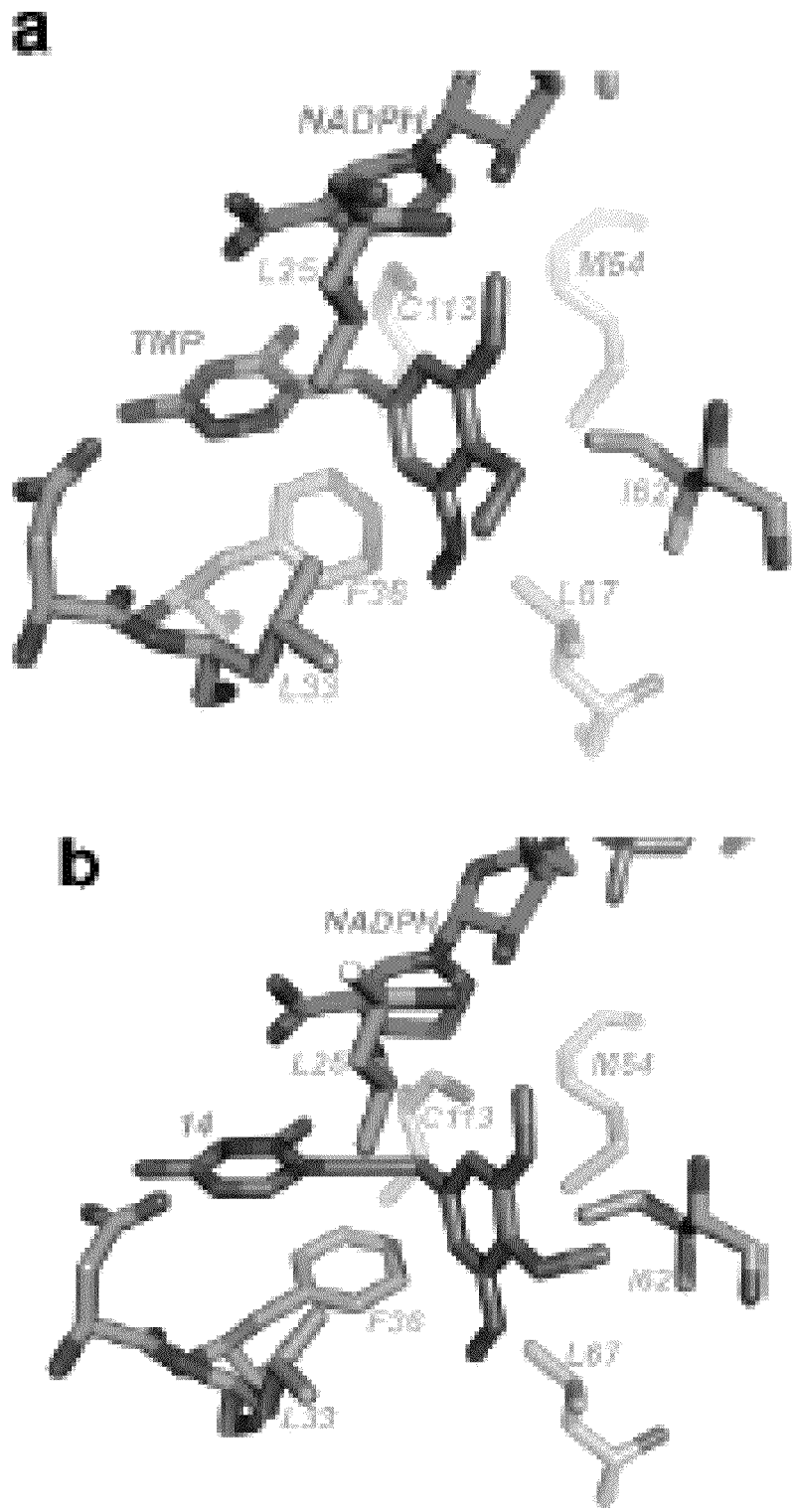
Figure 4A:
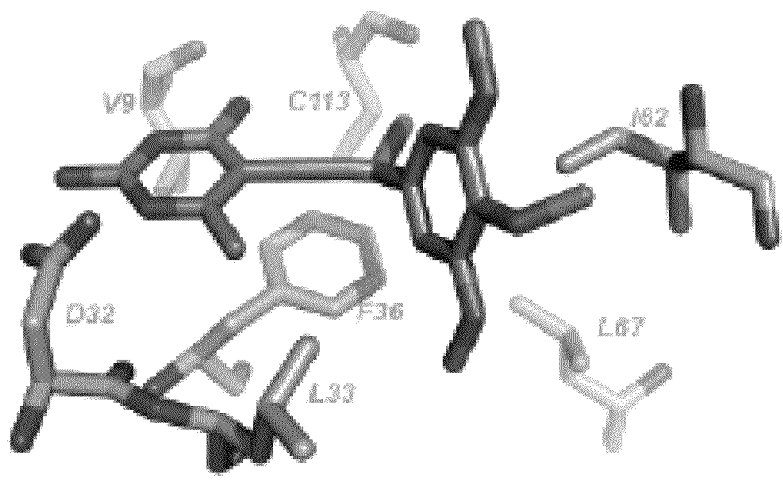
Figure 4B:
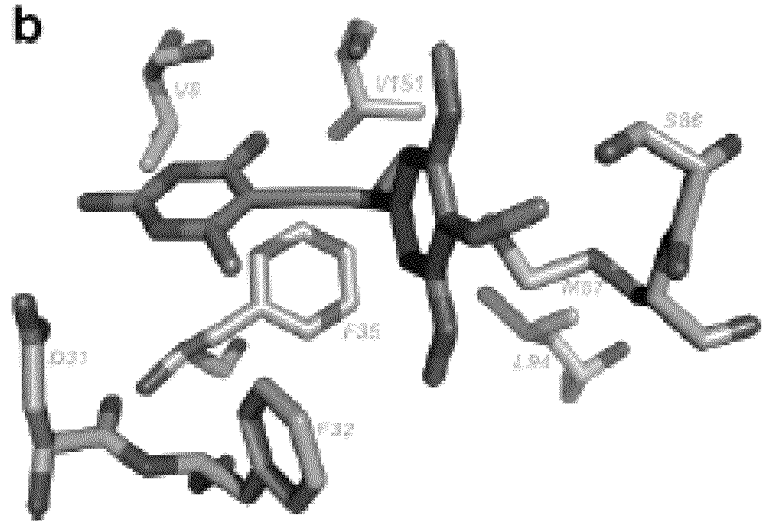

```
C.hominis    1   MSEKNVSIVVAASVLSSGIGINGQLPWS-ISEDLKPFSKITNNKCDSNKK----------
T.gondii     1   -MQKPVCLVVAMTP-KRGIGINNGLPWPHLTTDFKHFSRVTKTTPEEASRLNGWLPRKFA
                  :*  *.:***  :  . *****. :**.:  ::  *:*.**::*:..  :. .:

C.hominis   50   ----------------NALIMGRKTWDSIGR--RPLKNRIIVVISSSL---------PQD
T.gondii    59   KTGDSGLPSPSVGKRFNAVVMGRKTWESMPRKFRPLVDRLNIVVSSSLKEEDIAAEKPQA
                                 **::******:*; *  *** :*; :*:****          **

C.hominis   84   EADPNVVVFRNLEDSIENLMND--DSIENIFVCGGESIYRDALKDNFVDRIYLTRVALED
T.gondii   119   EGQQRVRVCASLPAALSLLEEEYKDSVDQIFVVGGAGLYEAALSLGVASHLYITRVARE-
                 *.:  .* *   .*    ::.  * ::  **::***  **  ..:*. **.  ....::*;**** *

C.hominis  142   IEFDTYFPEIP-------------------------------------ETFLPVYMSQTFC
T.gondii   178   PPCDVFFPAFPGDDILSNKSTAAQAAAPAESVFVPPCPELGREKDNEATYRPIFISKTFS
                 :  *.:** :*                                       *: *:::*:**.

C.hominis  167   TKNISYD--------
T.gondii   239   DNGVPYDFVVLEKRR
                   :.:.**
```

Figure 1

A

B

INHIBITORS OF DIHYDROFOLATE REDUCTASE WITH ANTIBACTERIAL ANTIPROTOZOAL, ANTIFUNGAL AND ANTICANCER PROPERTIES

PRIOR RELATED APPLICATIONS

The present application claims the benefit of priority to U.S. Provisional Patent Application Ser. No. 60/941,828 filed Jun. 4, 2007, the contents of which are incorporated herein by reference.

STATEMENT REGARDING FEDERALLY SPONSORED RESEARCH

This invention was made with government support under Grant No. GM067542 awarded by the National Institutes of Health. The government has certain rights in the invention.

TECHNICAL FIELD

This relates to compounds that inhibit dihydrofolate reductase (DHFR) and methods of using the compounds for treating pathogenic infections and neoplasias.

BACKGROUND OF THE INVENTION

Species of *Bacillus*, including *B. anthracis* and *B. cereus*, present significant health hazards. *B. anthracis* is the highly pathogenic, gram-positive bacteria that is responsible for the acute and often fatal disease, anthrax. It is categorized as a Type A pathogen by the National Institute of Allergy and Infectious Disease. Current therapeutics for *B. anthracis* infections have serious limitations including expense, resistance and contraindications in children. *B. anthracis* and *B. cereus* are closely related, in fact, biochemical and genetic evidence suggests that they should be considered a single species. Exposure to *B. cereus*, usually as a food contaminant, causes a number of infections including endophthalmitis, bacteremia, septicemia, endocarditis, pneumonia and meningitis, some of which have proven fatal.

*Cryptosporidium* and *Toxoplasma* are apicomplexan parasitic protozoa that cause severe disease in the population worldwide. Cryptosporidiosis, caused by *C. hominis*, is characterized by wasting disease and most often affects immune-compromised patients, the elderly, and day-care children, although very large outbreaks have occurred in otherwise healthy populations. Effective therapy for cryptosporidiosis is hard to find. At this time, there is a single approved therapeutic agent, nitazoxanide, against *Cryptosporidium* although the application of this drug is limited to immune-competent patients and effects have not been studied in children under 12 years of age. Toxoplasmosis, when transmitted congenitally as *T. gondii*, can cause neonatal death and, when transmitted through ingestion of contaminated meat or water, can cause fever and sore throat, or cerebral inflammation in immune-compromised patients. Both of these parasitic protozoa have been classified as Category B biodefense agents.

Systemic fungal infections are a significant and increasing cause of death and severe illness worldwide. Mortality rates due to *Candida* spp. infections were 38% between 1983 and 1986 and 49% between 1997 and 2001. The incidence of these infections has risen because of the increased number of immune-compromised patients. Up until the 1980s, *Candida albicans* was the primary cause of systemic candidemia infection and could be treated with traditional therapeutics including azole derivatives and amphotericin B. However, shifting epidemiology dictates that while *C. albicans* infections still represent the majority (~50%), other species of *Candida*, primarily *C. glabrata*, now cause a significant (~20%) number of bloodstream infections.

Dihydrofolate reductase (DHFR) has been a validated drug target for the treatment of bacterial and protozoal infections for decades. DHFR is an essential enzyme and plays a key role in the folate biosynthetic pathway. Occurring as a bifunctional protein with thymidylate synthase (DHFR-TS) in the apicomplexan protozoa, DHFR utilizes the cofactor NADPH to catalyze the reduction of dihydrofolate to tetrahydrofolate, thereby performing a key reaction in the sole de novo synthesis of deoxythymidine monophosphate (dTMP). Since DHFR is an essential enzyme to all cells, inhibitors targeting pathogenic organisms must be selective as well as potent in order to avoid complications resulting from inhibiting the human enzyme. The difficulty of achieving both potency and selectivity for *Cryptosporidium* DHFR was underscored by a study from Nelson and Rosowsky (*Antimicrob Agents Chemother* (2001) December; 45(12): 3293-303) in which they examined 96 structurally diverse DHFR inhibitors and were unable to identify compounds that were both potent and selective for *C. hominis* DHFR. DHFR has been widely conserved throughout evolution. However, several residue differences exist in the active sites of different species that make achieving selectivity for the pathogenic form of the enzyme possible.

The DHFR inhibitor pyrimethamine (i.e., 5-(4-chlorophenyl)-6-ethylpyrimidine-2,4-diamine) has been effectively used to treat toxoplasmosis as well as malaria, caused by another apicomplexan parasite, *Plasmodium* (such as against *Plasmodium falciprum*). However, many patients have had severe reactions to pyrimethamine, limiting its efficacy.

Trimethoprim (i.e., 5-(3,4,5-trimethoxybenzyl)pyrimidine-2,4-diamine) has been used effectively in the clinic as an antibacterial agent since the 1960s. For example, it has been used against *E. coli* and species of *Streptococcus*. It possesses excellent drug-like characteristics including a relatively low molecular weight (MW=290 Daltons). However, trimethoprim also exhibits a high affinity for only a small subset of species of DHFR from pathogenic organisms such as *Escherichia coli*. This limits its widespread application. Moreover, trimethoprim exhibits only moderate in vitro potency against DHFR from *C. hominis* (ChDHFR) and *T. gondii* (TgDHFR). Trimethoprim is less potent against DHFR from *Cryptosporidium* and *Toxoplasma*, two *Apicomplexan* protozoa.

Amphotericin B and azole derivatives have traditionally been used to treat *C. albicans* infections. However, other species of *Candida*, primarily *C. glabrata* have a lower susceptibility toward azole compounds, especially the commonly used agent, fluconazole. The therapeutic window to treat *C. glabrata* is even narrower since *C. glabrata* strains are also often resistant to Amphotericin B.

During drug development, it is often appreciated that during the lead optimization process, increases in potency correlate with increases in molecular weight. However, the additional molecular weight frequently represents a liability as it compromises the drug-like properties of the lead. The necessary compromise between increasing molecular weight and increasing affinity can be examined quantitatively with the concept of ligand efficiency. Ligand efficiency is defined as the overall binding energy per nonhydrogen atom; a higher ligand efficiency defines a superior compound. Interestingly, although methotrexate (i.e., (S)-2-(4-(((2,4-diaminopteridin-6-yl)methyl)methylamino)benzamido)pentanedioic acid or MTX) is a much more potent compound ($IC_{50}$ values against ChDHFR and TgDHFR are 23 nM and 14 nM, respectively) than trimethoprim, it has the same ligand efficiency as trimethoprim, implying that the increased potency is largely dependent on the increased molecular weight rather than a more optimal positioning of pharmacophoric elements.

Therefore, what are needed are pharmaceutical compositions containing relatively low molecular weight compounds that are specific and effective for the treatment of various pathogenic infections.

BRIEF SUMMARY OF THE INVENTION

Compounds, compositions, processes of making compounds, and methods of treating individuals suffering from bacterial, fungal, and protozoal infections using the compounds and compositions described herein are provided. Also provided is a method of treating an individual who is suffering from cancer, or neoplastic disease, by the compounds described herein.

Various pyrimidine systems, such as pyrido[2,3-d]pyrimidine ring systems, have been studied due to their involvement in the inhibition of dihydrofolate reductase (DHFR) enzyme activity. The structure of the DHFR enzyme from *Cryptosporidium hominis* and *Toxoplasma gondii* is described in an article in the *Journal of Medicinal Chemistry* (2007) 50: 940-950, which is herein incorporated by reference in its entirety.

The compounds disclosed herein are pyrimidine derivatives that function as a new class of DHFR inhibitors. These compounds have been tested as inhibitors of DHFR from bacterial, fungal, and protozoal organisms such as *B. anthracis, S. aureus, C. hominis, C. albicans*, and *C. glabrata*, and results indicate that these compounds are potent and selective for the inhibition of these types of pathogenic organisms and the treatment of bacterial, fungal, and protozoal infection.

Moreover, structure-activity relationships have been developed for a number of DHFR inhibitors based on a homology model of the *B. anthracis* enzyme. In brief, among the most potent compounds previously tested for *B. anthracis* and *B. cereus* DHFR was an annulated 2,4-diaminopyrimidine ring with an alkyl linker attached to a substituted phenyl ring. However, the compounds of the present invention are more generic and more potent inhibitors. For example, the clinically used trimethoprim (which has a methylene linker) does not appear to place the substituted phenyl ring deep enough into the hydrophobic pocket, which may explain the decrease in potency.

Importantly, the compounds provided herein are effective antifungal and antibacterial agents in vitro using cultures of organisms (*B. subtilis, B. cereus, C. albicans, C. glabrata* and *C. neoformans*). Although most of the antipathogenic inhibitors described herein are nontoxic for mammalian cells, at least one of the newly developed inhibitors displays mammalian cell toxicity and is, therefore, useful as an anticancer agent.

The propargyl-based DHFR inhibitors of the compositions and methods described herein are good drug candidates having low molecular weight (under 500 Daltons) and therefore plenty of capacity for added functionality. Modifications of the compounds provided herein are relatively straightforward to synthesize, costs can be minimized, and the compounds can have departure points for focused libraries for increased diversity. As inhibitors of *B. anthracis*, the compounds described herein present an opportunity for decreased side effects. As inhibitors of *S. aureus*, these compounds provide a desperately needed alternative. As antifungal inhibitors, the compounds described herein potently and selectively inhibit DHFR from several fungal species, presenting the opportunity to develop a broad-spectrum inhibitor that can be administered without diagnosing the exact fungal infection. As antiprotozoal inhibitors, the compounds provided herein are first-in-class (such as for *Cryptosporidium*) and/or may offer an opportunity for fewer side effects (such as for *Toxoplasma*).

BRIEF DESCRIPTION OF THE SEVERAL VIEWS OF THE DRAWINGS

FIG. 1 shows the amino acid sequence alignment between ChDHFR and TgDHFR (PDB codes: AAB00163 and XP665866, respectively) wherein the arrows represent amino acids at the active sites.

FIG. 2 is a molecular model showing methotrexate (MTX) in the ChDHFR active site.

FIGS. 3A and 3B are molecular models showing, in FIG. 3A, trimethoprim (TMP) modeled in the active site of ChDHFR; and in FIG. 3B, 5-[3-(3,4,5-trimethoxyphenyl) prop-1-yn-1-yl]pyrimidine-2,4-diamine modeled in the active site of ChDHFR.

FIGS. 4A and 4B are molecular models showing (R)-6-methyl-5-[3-(3,4,5-trimethoxyphenyl)but-1-yn-1-yl]pyrimidine-2,4-diamine bound to ChDHFR in FIG. 4A and bound to TgDHFR in FIG. 4B.

FIGS. 5A and 5B are molecular models showing the aza-bridged bicyclic ring occupying the "central" hydrophobic pocket with the apical position pointing "up" in FIG. 5A and pointing "down" in FIG. 5B.

FIG. 6 shows a model of the oxabicyclic ring system in the active site of BaDHFR (blue). Both endo and exo substituents from the 3-carbon bridge are easily accommodated in the "up" pocket.

FIG. 7 shows a model of the carbabridged bicyclic system in the active site of BaDHFR.

FIGS. 8A and 8B are molecular models as seen from the same view with co-crystallized ligands in the active site (FIG. 8A: ChDHFR (green) and FIG. 8B hDHFR (blue) (PDB codes: 1SEJ and 1KMV, respectively)), demonstrating the substantial difference in active site opening. The PEKN loop residues are labeled on hDHFR, with Asn64 indicated on the underside of the loop.

FIGS. 9A-C are molecular models of UCP111A also referred to herein as compound X, (pink) (9A), UCP 111D (yellow) (9B) and UCP 111F (white) (9C) docked into ChDHFR in their computationally preferred docking orientation. ChDHFR is shown as a surface mapped with lipophilicity moving from lipophilic (red) to neutral (green) to hydrophilic (blue).

FIGS. 10A-C are molecular models showing UCP111A (compound X) (pink), UCP111D series (yellow) and UCP111F series (UCP111F and UCP111F2Me white, UCP111F26Me blue) docked into the hDHFR ensemble member with the widest opening. hDHFR surface is colored based on lipophilicity, moving from lipophilic (red) to neutral (green) to hydrophilic (blue).

FIGS. 11A and 11B are molecular models showing the structure of CgDHFR bound to NADPH and compound 11. FIG. 11A shows the overall structure of CgDHFR (NADPH and the crystallized ligand are shown in red); and in FIG. 11B, showing CgDHFR (purple) superimposed with CaDHFR (cyan). The CgDHFR insert and loop proximal to the active site are noted.

FIGS. 12A and 12B are models showing interactions of compound 11 with CgDHFR (FIG. 12A), with FIG. 12B showing a comparison of CgDHFR (purple) and hDHFR (salmon) (only key residues in hDHFR at the active site are shown for clarity).

Figure 13:
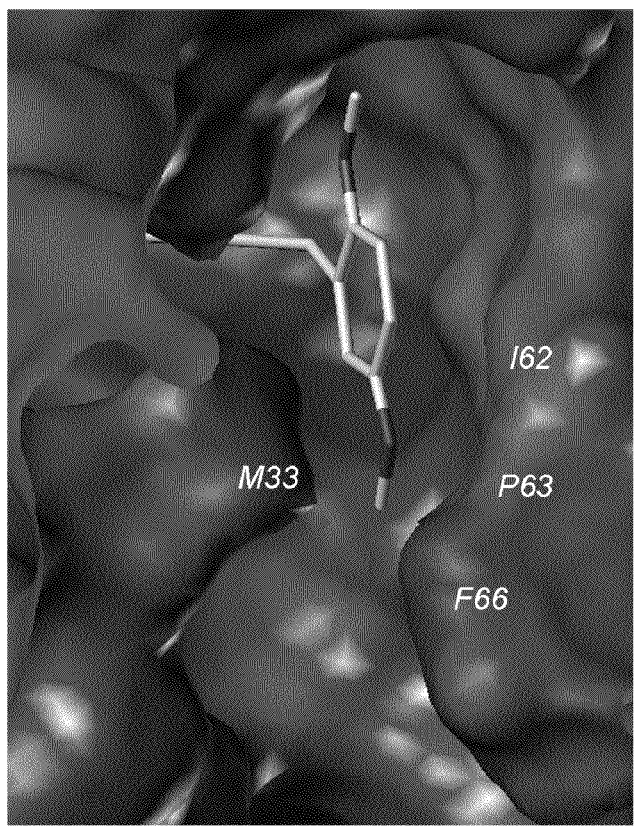

FIG. 13 is a surface representation of CgDHFR at the active site with compound 11 bound. The surface is colored using a gradient that extends from lipophilic (red) to neutral (green) to hydrophilic (blue). The view is the same as that shown in FIG. 11A. Residues near the 5' position of the aryl ring are labeled.

DETAILED DESCRIPTION

Compounds, compositions containing the compounds, and methods of using the compounds and compositions as antibacterials, antifungals, antiprotozoals, and anti-cancer agents are provided. The compounds described herein include a 2,4-diaminopyrimidine ring with a propargyl linker to an optionally substituted aryl or heteroaryl ring. The compounds are pyrimidine derivatives that function as a new class of DHFR inhibitors.

The compositions provided herein are novel, relatively low molecular weight compounds that act as DHFR inhibitors and exhibit good potency against DHFR from a plurality of species. The structures of the enzymes will guide the design of additional derivative compounds. These compounds allow the incorporation of additional functionality for selectivity without overstepping molecular weight boundaries.

DHFR as part of its molecular mechanism reduces dihydrofolate to tetrahydrofolate. Thus, the inhibition of DHFR deprives the cell of tetrahydrofolate, without which the cell cannot produce 5,10-methylenetetrahydrofolate. 5,10-Methylenetetrahydrofolate is essential for cell growth. The inhibition of DHFR by the compounds, and pharmaceutically acceptable salts thereof, described herein therefore results in the inhibition of DNA synthesis and leads to cell death. Thus, the compounds provided herein are useful as anti-cancer, or anti-neoplastic, agents.

In addition to the above-recited molecular mechanism, the pyrimidine derivative compounds described herein also function as thymidylate synthase (TS) inhibitors. TS, along with DHFR, forms part of the system responsible for the synthesis of deoxythymidylate (dTMP) from deoxyuridylate (dUMP). TS catalyzes the sole de novo synthesis of dTMP from dUMP. Inhibition of TS, therefore, deprives the cell of thymidine, which is an essential constituent of DNA. Accordingly, this inhibition means that the compounds described herein are useful for targeting any of a number of organisms, such as bacteria involved in bacterial infections, fungi, and protozoa. Moreover, this inhibition also provides an alternative molecular mechanism for targeting various cancers.

One embodiment of the compositions and methods described herein relates to compounds of Formula I, wherein Formula I is

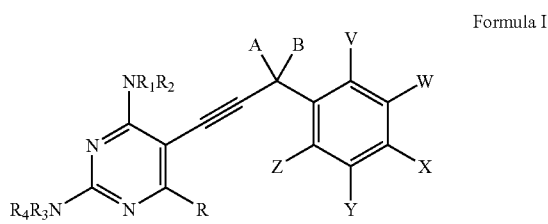

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-5}$alkyl, cycloalkyl (e.g., cyclohexyl), alkoxyalkyl (e.g., —$C_3H_6OC_2H_5$), alkoxyalkoxyalkyl (e.g., —$C_2H_4OC_2H_4OC_2H_5$), arylalkyl (e.g., phenylmethyl or 2-pyridylmethyl), alkylcarbonyl, [e.g., —(C═O)$CH_3$, —(C═O)CH($CH_3$)$_2$, —(C═O)$C_{11}H_{23}$], cycloalkylcarbonyl (e.g., cyclohexylcarbonyl), alkoxycarbonyl[e.g., —(C═O)O$C_2H_5$], alkoxyalkylcarbonyl[e.g., —(C═O)$C_2H_4OC_2H_5$], alkoxyalkoxyalkylcarbonyl[e.g., —(C═O)$C_2H_4OC_2H_4OC_2H_5$], arylcarbonyl (e.g., benzoyl), pyridinylcarbonyl (e.g., 3-pyridinylcarbonyl), aryloxyalkyl[e.g., —C(═O)$CH_2OC_6H_5$], haloalkylcarbonyl[e.g., —C(═O)($CH_2$)$_2$F], and cyanoalkylcarbonyl[e.g., —C(═O)($CH_2$)$_3$CN];

wherein A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

wherein, A and B together with the carbon to which they are connected can form a ring of from 3 to 7 members wherein the ring members are selected form the group consisting of alkylene, alkenylene, and alkynylene, wherein any of the alkylene, alkenylene, and alkynylene groups may optionally be interrupted by one or more heteroatoms selected from the group consisting of O, N, S, and Se. In a variation of this embodiment, the alkylene or alkenylene may be optionally substituted with one or more of $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

wherein V, W, X, Y, and Z are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally independently substituted one or more times with halogen, lower haloalkyl, lower alkyl, lower alkoxy, or lower alkylsulfonyl, wherein lower used in conjunction with any of the above groups is preferably $C_1$ to $C_6$.

In an embodiment, at least one of V, W, X, Y, and Z is an alkoxy group. In a variation of this embodiment, at least one of V, W, X, Y, and Z is a methoxy group. In a further variation of this embodiment, at least one of W, X, and Y is a methoxy group.

In an alternate embodiment, at least two of V, W, X, Y, and Z are alkoxy groups. In a variation of this embodiment, at least one of V, W, X, Y, and Z is a methoxy group. In a further variation of this embodiment, at least one of W, X, and Y is a methoxy group.

In a further embodiment, at least three of V, W, X, Y, and Z are substituted with a substituent other than hydrogen and at least one of V, W, X, Y, and Z is an alkoxy group. In a variation of this embodiment, the alkoxy group is a methoxy group.

In a further embodiment, at least one of V, W, X, Y, and Z is not hydrogen or halogen. In a variation of this embodiment, at least one of V, W, X, Y, and Z is not hydrogen, fluoro, or chloro.

In an embodiment, at least one of A and B is not $C_{1-5}$ alkyl and at least one of V, W, X, Y, and Z is not hydrogen or halogen. In a variation of this embodiment, at least one of V, W, X, Y, and Z is not hydrogen, fluoro, or chloro. In a variation of this embodiment, none of V, W, X, Y, and Z is fluoro or chloro.

In an embodiment, at least one of V, W, X, Y, and Z is not a hydrogen, fluoro, chloro, trifluoromethyl, methylsulfonyl, or a 4-chlorophenyloxy substituent. In a variation of this embodiment, at least one of V, W, X, Y, and Z is not a hydrogen, fluoro, chloro, trifluoromethyl, methylsulfonyl, or a 4-chlorophenyloxy substituent or is a substituent that contains a carbonyl.

In an embodiment, A and/or B is a hydrogen, methyl or ethyl group.

In an alternate embodiment, compounds of the compositions and methods described herein are encompassed by Formula IA

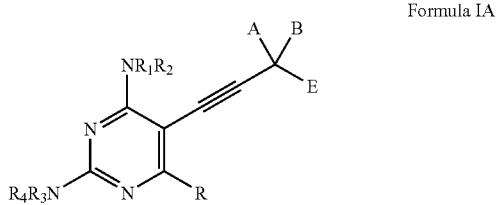

Formula IA wherein R, $R_1$, $R_2$, $R_3$, $R_4$, and A and B are defined as above when they are substituents in Formula I;

wherein E can be a phenyl group, which is substituted by V, W, X, Y and Z as in Formula I; alternatively, E can be a azabicyclo, oxabicylo, or carbabridged substituent as shown in Formulas IIIA, IIIB, and IIIC, respectively.

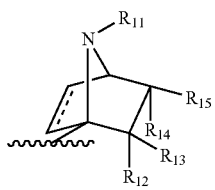

Formula IIIA

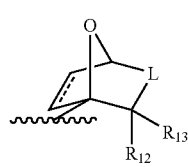

Formula IIIB

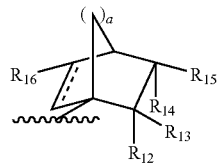

Formula IIIC wherein a is 1 or 2;

wherein the propargyl linker as shown in Formula IA is joined at the bridgehead carbon in each of Formulas IIIA, IIIB, and IIIC;

wherein $R_{11}$, $R_{12}$, $R_{13}$, $R_{14}$, $R_{15}$ and $R_{16}$ are selected from the group consisting of hydrogen, $C_{1-3}$alkyl, —C(O)$C_{1-3}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally independently substituted one or more times with halogen, lower haloalkyl, lower alkyl, lower alkoxy, or lower alkylsulfonyl, wherein "lower" used in conjunction with any of the above group means $C_1$ to $C_6$;

wherein L is a $C_{1-2}$alkylene or $C_{1-2}$alkenylene group optionally and independently substituted with one to four substituents selected from the group consisting of hydrogen, $C_{1-3}$alkyl, —C(O)$C_{1-3}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally independently substituted one or more times with halogen, lower haloalkyl, lower alkyl, lower alkoxy, or lower alkylsulfonyl, wherein "lower" used in conjunction with any of the above group means $C_1$ to $C_6$; and wherein the dotted line in the above Formulas IIIA, IIIB, and IIIC represents a single or double bond.

In an alternate embodiment, compounds of the compositions and methods described herein are encompassed by the compounds of Formula II:

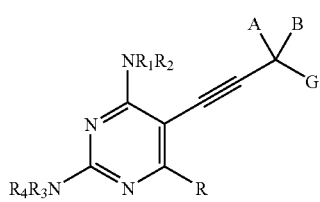

Formula II wherein R, $R_1$, $R_2$, $R_3$, $R_4$, and A and B are defined as above when they are substituents in Formula I;

wherein G is selected from the group consisting of Formula IVA, Formula IVB, Formula IVC, Formula IVD, Formula IVE, and Formula IVF;

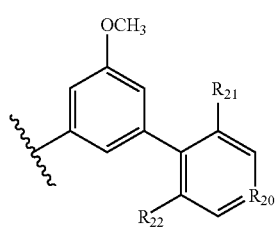
Formula IVA

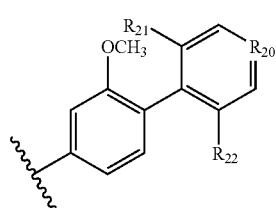
Formula IVB

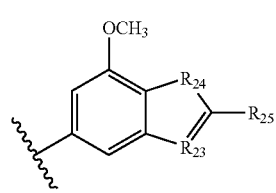
Formula IVC

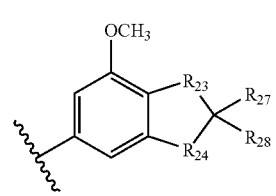
Formula IVD

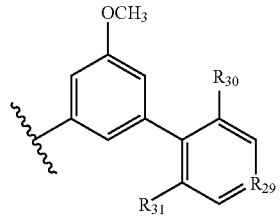
Formula IVE

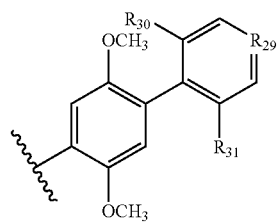
Formula IVF wherein $R_{20}$, $R_{23}$, $R_{24}$, and $R_{29}$ is selected from the group consisting of CH, $CH_2$, O, N, and NH so that the valence for each of these substituents is neutral (i.e., these substituents are neither positively nor negatively charged);

wherein $R_{21}$, $R_{22}$, $R_{25}$, $R_{27}$, $R_{28}$, $R_{30}$ and $R_{31}$ are selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl.

A general reaction scheme to generate the compounds of Formula I is shown below in scheme I.

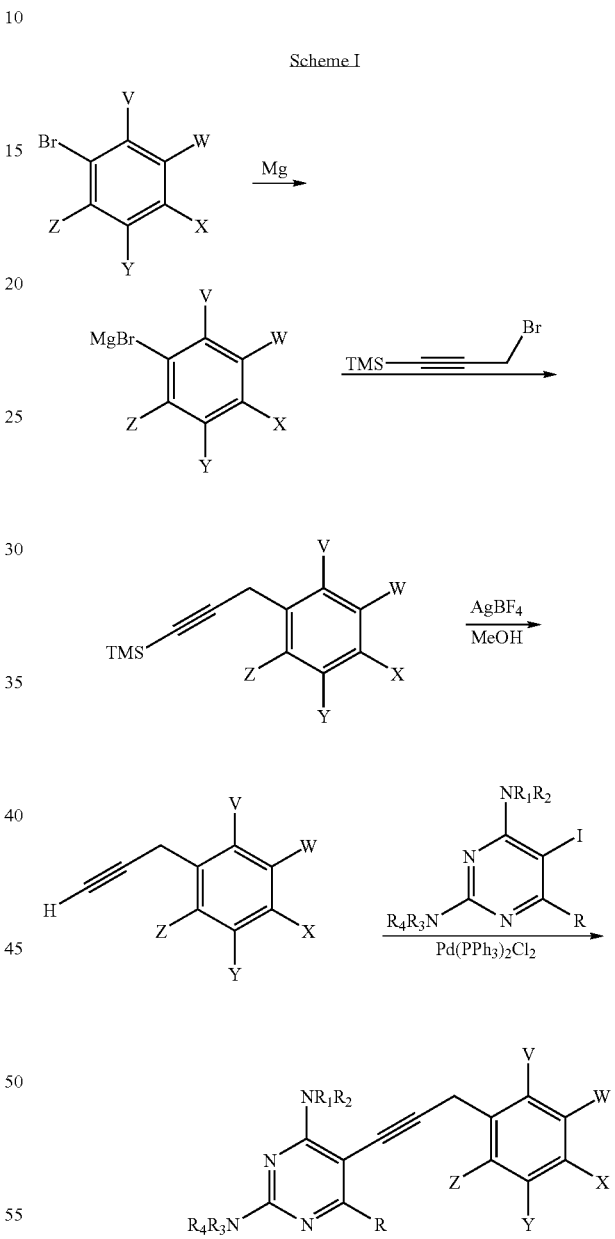
Scheme I

In scheme I, it should be recognized that protecting groups may need to be used depending on the substituents that are represented by V, W, X, Y, and Z. Moreover, it should be recognized that A and/or B may be added to the above scheme I (as shown in Formula I) to place a substituent on the methylene functionality adjacent to carbon-carbon triple bond.

Another possible reaction scheme that may be used to generate the compounds of the Formula I is shown below in scheme II.

Scheme II

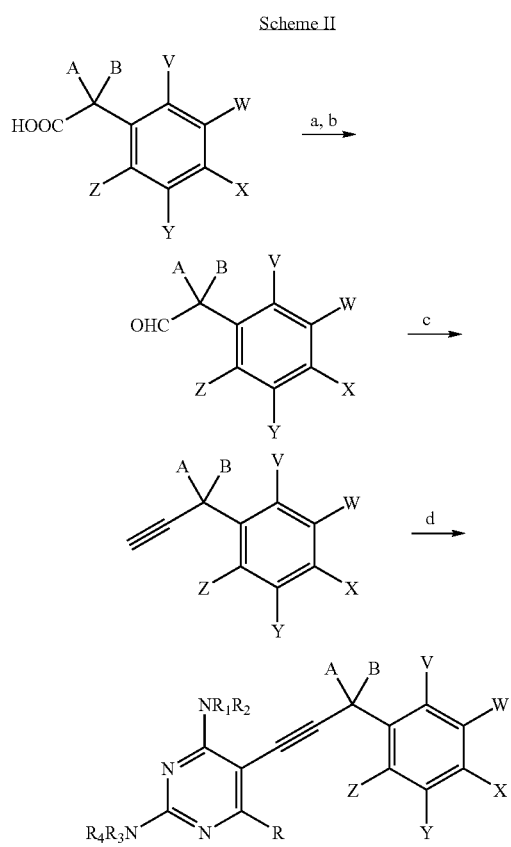

a) LAH, Et2O
b) Dess-Martin periodance, DCM
c) dimethyl(1-diazo-2-oxopropyl)phosphonate, $K_2CO_3$, MeOH
d) pyrimidinyl derivative, $Pd(PPh_3)_2Cl_2$, CuI, $Et_3N$, DMF It should be understood that the appropriate protecting and deprotecting groups may need to be used depending on the various substituents represented by A, B, V, W, X, Y, and Z in scheme II. Likewise, one should recognize that the appropriate protecting and deprotecting groups may need to be used depending on the various substituents that may be present on the nitrogens at the 2 and 4 position of the pyrimidinyl derivative that are represented by $R_1$, $R_2$, $R_3$ and $R_4$. It should also be recognized that the carbon that contains substituents A and B in the above scheme may be chiral (and one enantiomer may be present in large excess over the other isomer). Accordingly, in scheme II, any enantiomeric excess will be maintained when scheme II is followed to generate the pyrimidinyl propargyl aryl compound (such as shown in Formula I). Alternatively, substituents A and B can be incorporated during the synthetic process. For example, in scheme II, substituents A and B may be added after steps a) and b) are performed but prior to performing step c).

Some of the compounds can be made by the methods that are shown in the reference Pelphrey et al. (*J. Med. Chem.*, 2007, 50, pp. 940-950), which is herein incorporated by reference in its entirety for all purposes.

Moreover, it should be recognized that the above reaction schemes I and II can easily be modified to make any of the compounds of Formula IA; for example, the compounds wherein E in Formula IA is any of Formulas IIIA, IIIB, or IIIC.

It is believed that even greater levels of potency may be achieved by taking advantage of regions of space that have yet to be explored by the compounds that have presently been made. Analysis of representative inhibitors bound to BaDHFR has suggested five distinct library topologies that may lead to increased potency against the bacterial enzyme. These five libraries can be roughly grouped into two major superfamilies, two projecting a planar, aromatic ring in the central hydrophobic pocket and three which present a non-aromatic, bridged bicyclic scaffold into the same general region. See the compounds listed below.

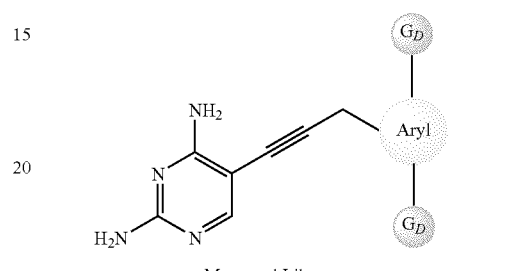

Monoaryl Library

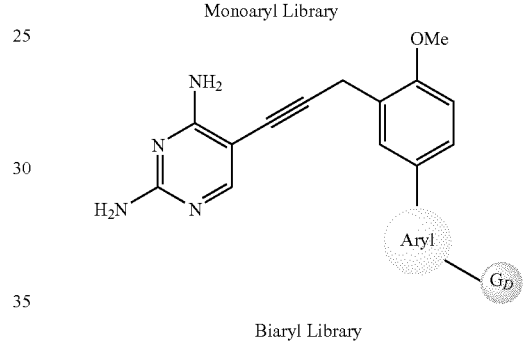

Biaryl Library

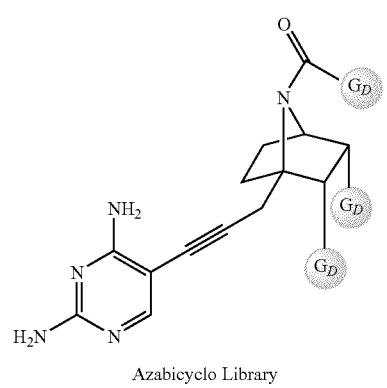

Azabicyclo Library

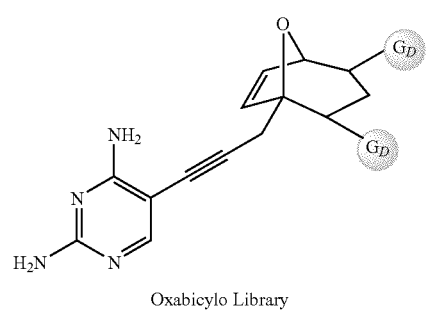

Oxabicylo Library

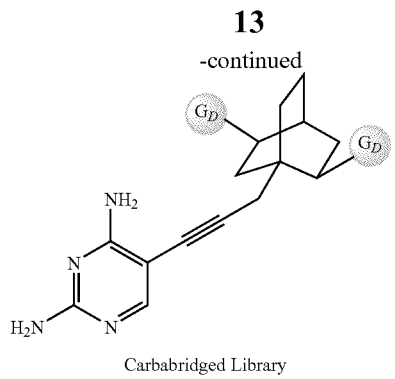

Carbabridged Library

The above families show the general topology of the DHFR inhibitor libraries. In the above representations of the library components, aryl represents a diverse group of benzenoid or non-benzenoid aromatics and GD represents a diverse collection of substituents appended onto a conserved core region.

Azabridged Library

Figure 5A:
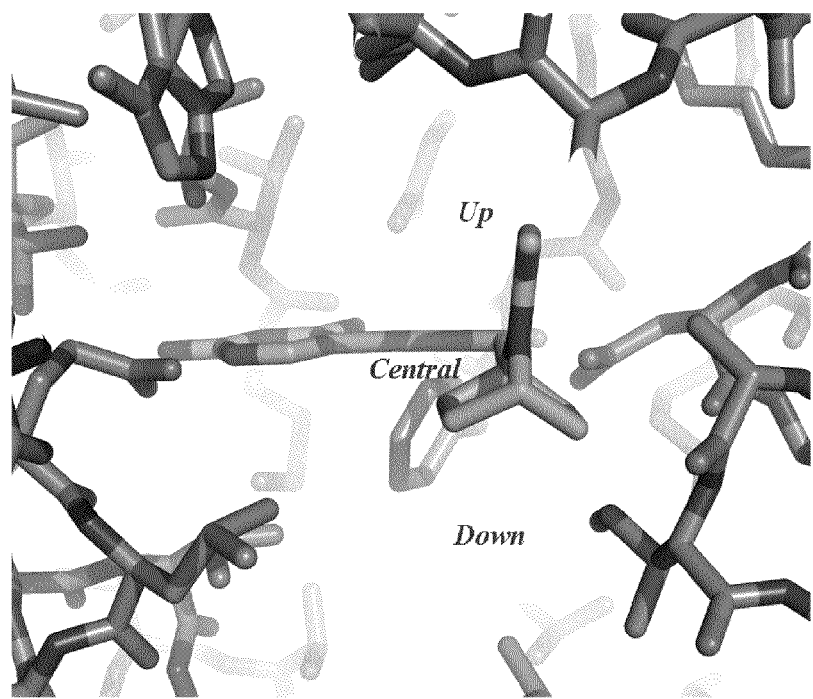
Figure 5B:
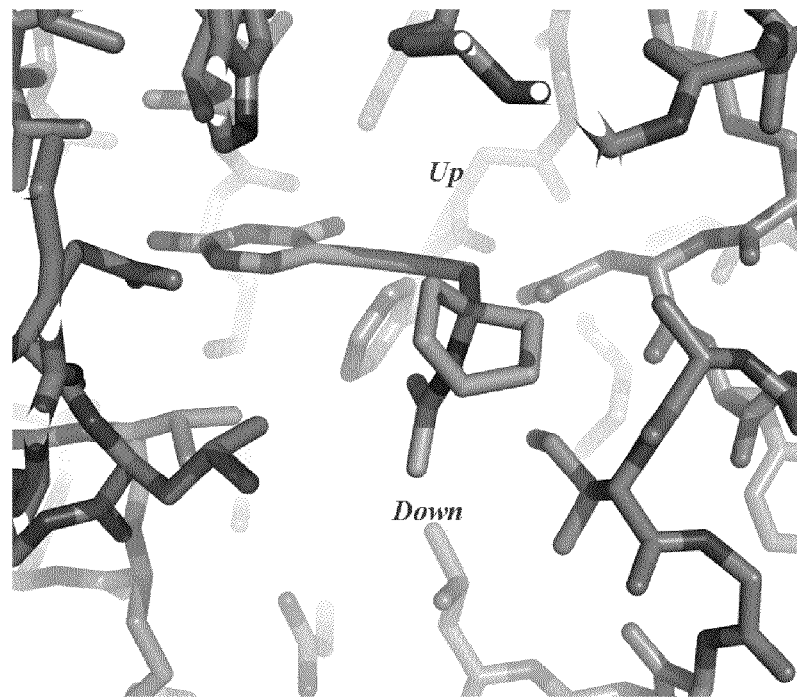
Figure 6:
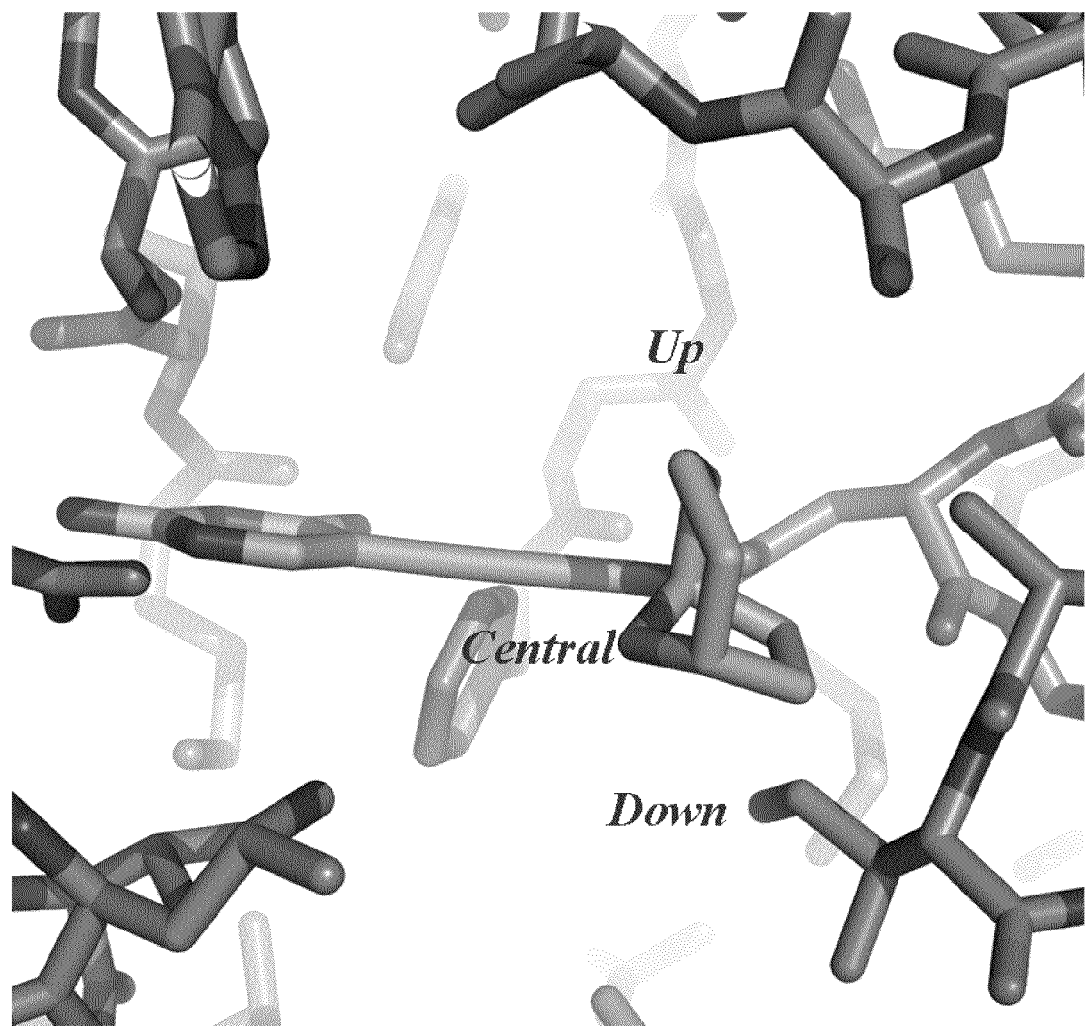

In one embodiment, the scaffold is based on an azabicyclo [2.2.1]heptane nucleus. Docking of the parent aza-bridged analog to the active site of BaDHFR suggests that functionality projecting from the apical position is well-suited to occupy either the "up" or "down" pocket depending on which rotameric state is bound to the enzyme (see FIG. 5). In either case, once this functionality is placed in one pocket the opposite pocket is directly accessible from functionality projecting from the endo-substituents of the bicyclic system. A number of different rotamers have been explored and found that keeping one of the two carbon bridges unsubstituted in order to avoid steric conflicts with Ile 51 generates a good fit. Our first-generation aza-bridged design will originate from two isomeric scaffolds, each containing two points of diversity, the bridging nitrogen and an endo hydroxy group that is either proximal or distal to the propargyl linker.

A Diels-Alder approach to the azabicyclo[2.2.1]heptane scaffold (see formula IIIA) may face the problem of competing electrophilic substitution or generally low reactivity due to appreciable resonance stabilization of the pyrrole nucleus. However, it has been shown that acetyelenic dieneophiles such as dimethylacetylene dicarboxylate and tosylacetylene add effectively to both unsubstituted and 2,5-disubstituted pyrroles. Mono-substituted pyrroles may have regiocontrol issues. These scaffolds may have utility beyond those in this application as few preparative routes to this class of compounds exist despite general interest in fused-ring systems. (see Scheme 5).

Scheme 5. Diels-Alder route to azabridged scaffolds

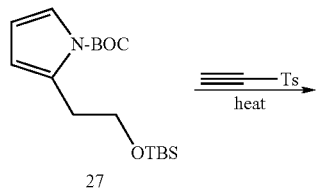

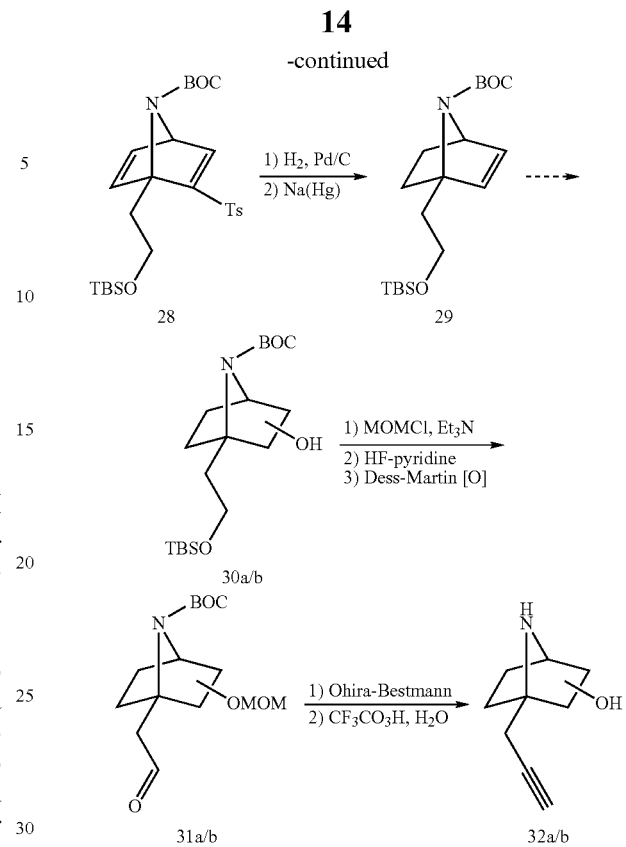

The protected pyrrole-2-ethanol 27 has been previously prepared for unrelated studies. Diels-Alder cycloaddition with tosyl acetylene is expected to give regioisomer 28 based on simple electronic considerations. Following well-known precedent for the parent system, the unsubstituted olefin and tosyl moiety are sequentially reduced to give alkene 29. The common intermediate 29 will be processed to the regioisomeric alcohols 30a and 30b as outlined below. Protecting group adjustments and oxidation to the aldehydes 31a and 31b will be followed by homologation and a global deprotection to give the common scaffolds 32a and 32b. In the parent azabicyclic system related to 29 without bridgehead substitution, it is known that addition to the olefin (epoxidation, dihydroxylation) takes place exclusively from the exo-face. However, the presence of substitution at the bridgehead may provide additional steric impedance around the olefin and switch the selectivity to an endo-mode attack. Alternate routes from intermediate 29 based on the intrinsic facial control are shown in Scheme 6.

Scheme 6. Elaboration of common azabridged intermediate

Exo-preference

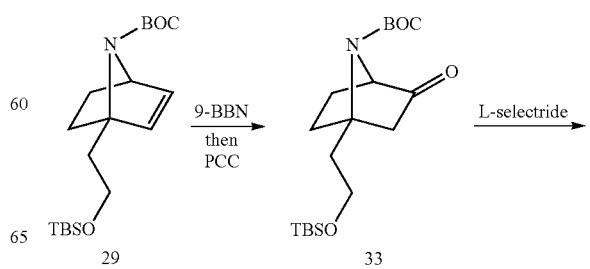

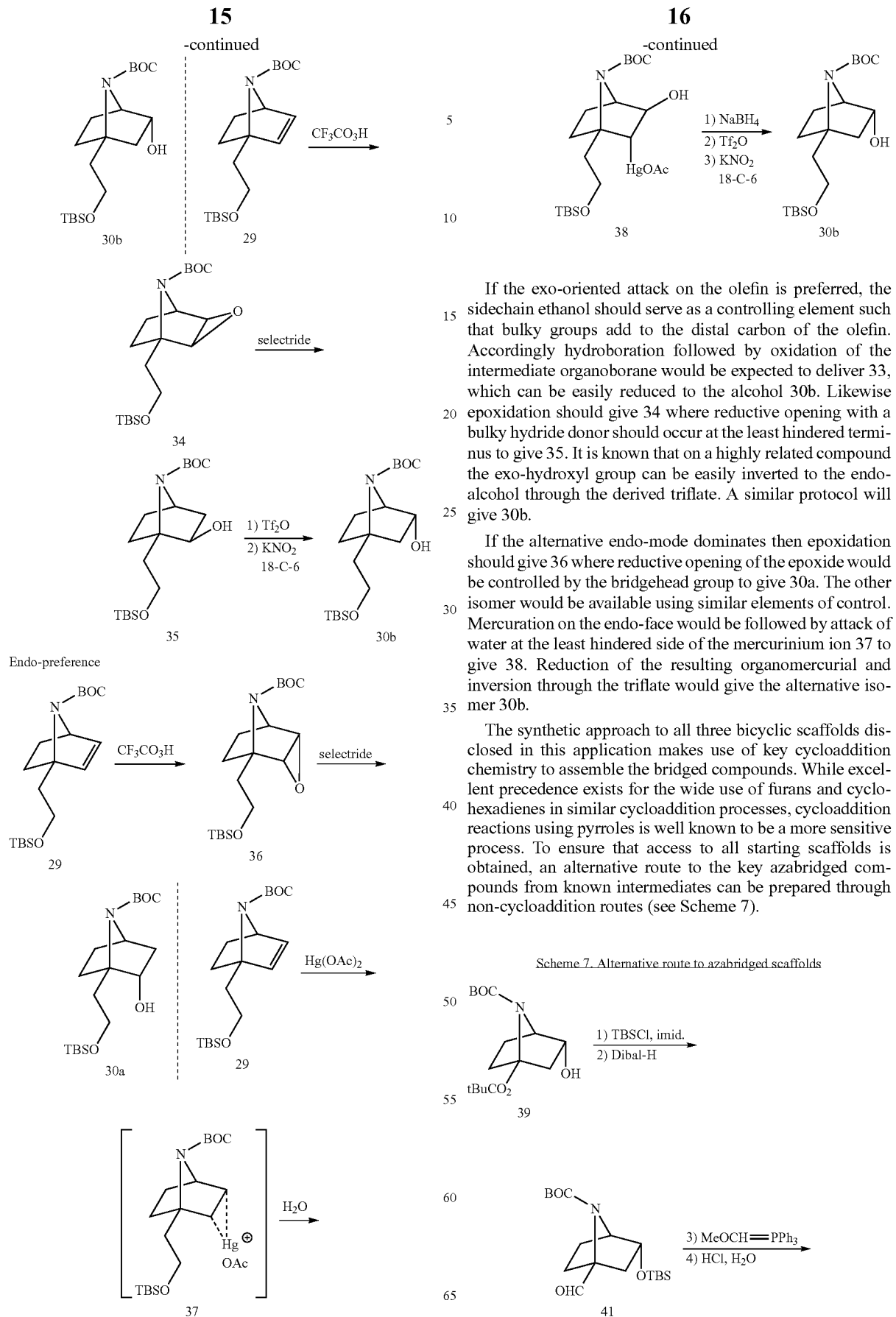

If the exo-oriented attack on the olefin is preferred, the sidechain ethanol should serve as a controlling element such that bulky groups add to the distal carbon of the olefin. Accordingly hydroboration followed by oxidation of the intermediate organoborane would be expected to deliver 33, which can be easily reduced to the alcohol 30b. Likewise epoxidation should give 34 where reductive opening with a bulky hydride donor should occur at the least hindered terminus to give 35. It is known that on a highly related compound the exo-hydroxyl group can be easily inverted to the endo-alcohol through the derived triflate. A similar protocol will give 30b.

If the alternative endo-mode dominates then epoxidation should give 36 where reductive opening of the epoxide would be controlled by the bridgehead group to give 30a. The other isomer would be available using similar elements of control. Mercuration on the endo-face would be followed by attack of water at the least hindered side of the mercurinium ion 37 to give 38. Reduction of the resulting organomercurial and inversion through the triflate would give the alternative isomer 30b.

The synthetic approach to all three bicyclic scaffolds disclosed in this application makes use of key cycloaddition chemistry to assemble the bridged compounds. While excellent precedence exists for the wide use of furans and cyclohexadienes in similar cycloaddition processes, cycloaddition reactions using pyrroles is well known to be a more sensitive process. To ensure that access to all starting scaffolds is obtained, an alternative route to the key azabridged compounds from known intermediates can be prepared through non-cycloaddition routes (see Scheme 7).

Scheme 7. Alternative route to azabridged scaffolds

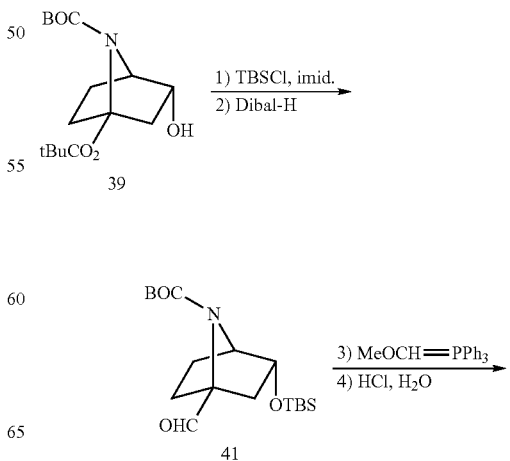

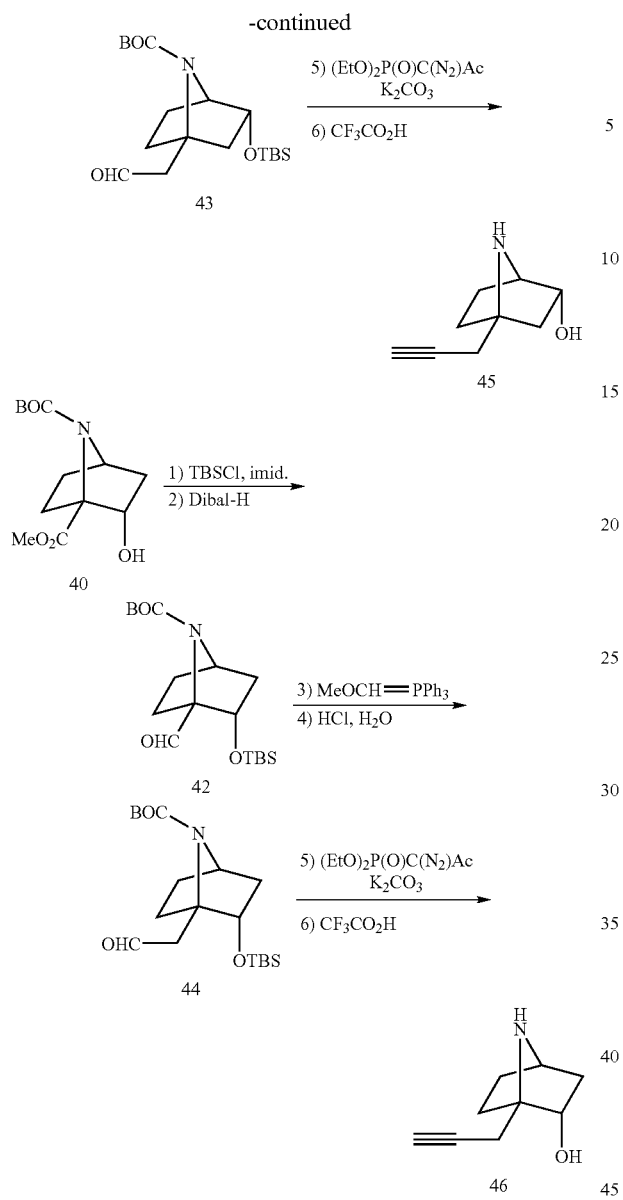

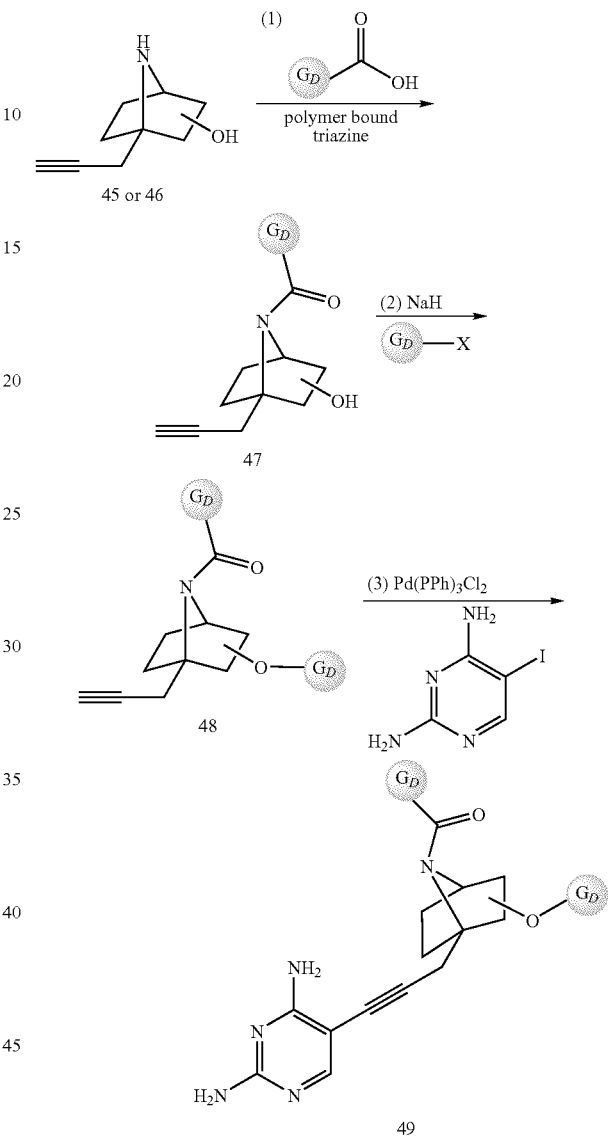

Scheme 8. Elaboration of azabicyclic scaffolds to give inhibitor libraries

Endo-alcohols 39 and 40 are known and both can be prepared through short sequences and in both racemic and enantiomeric pure form. Racemic compounds can be used to prepare specific compounds as single enantiomers. Initial protection of the free hydroxyl group as a silyl ether will be followed by semi-reduction of the bridgehead ester to the corresponding aldehydes 41 and 42. Key to the preparation of the scaffolds is the ability to homologate the aldehyde. Chain extension will then be performed by employing the well-known methoxy Wittig reagent which will generate aldehydes 43 and 44 upon simple acidic hydrolysis. Once the aldehyde is in-hand, a second homologation to the terminal acetylene will follow using the Ohira-Bestmann protocol and a final simultaneous deprotection of the BOC and TBS groups under acidic condition will give the two key scaffolds 45 and 46 for library construction.

Although the preparation of these bridged scaffolds requires several steps, diversity is not introduced until the very end of the synthesis meaning that very few transformations or purifications need to be conducted in parallel. Parallel synthesis of the library means that the library compounds can be generated in three steps from the scaffolds (see Scheme 8).

Scaffolds 45 and 46 both contain two sites for diversification. The bridging nitrogen is expected to react much faster than the endo alcohol such that an initial acylation using a solid phase coupling reagent will be conducted in parallel to give amides 47. A second diversification can be accomplished on the alcohol such as direct alkylation to form a diverse array of ethers, esters or other oxygen containing compounds 48. The final stage of library construction will involve the standard Sonagashira coupling with the iodopyrimidine to give the final library 49.

Oxabridged Library

Another attractive scaffold is based on the oxabicyclo [3.2.1]octane skeleton (see Formula IIIB). This scaffold appears only slightly different than the previously described azabicyclic system. However, the change in the size of the bridges appears to alter the binding mode of the bicyclic scaffold. The larger and more flexible 3-carbon bridge, with varying substitutions forms good van der Waals contacts with residues in the "up" pocket (see FIG. 5). The two-carbon bridge when it is unsubstituted and in the alkene oxidation state provides compounds that dock well in that they limit potential steric interactions with Ile 51.

A variety of methods exist for the preparation of these types of ring systems. It has been shown that unsubstituted, 2-monosubstituted and 2,5-disubstituted furans undergo a cyclocondensation reaction with terabromocyclopropene (TBCP) to give a highly functionalized oxabicyclo[3.2.1] octadiene core. The high degree of functionality around this compact system allows for the straightforward and stereoselective introduction of groups onto the three-carbon bridge. Methodologies have also been developed to prepare enantiopure versions of these types of derivatives. For these scaffolds the TBCP reaction can be employed with a protected 3-furylethanol, a compound that has been previously prepared (see Scheme 9).

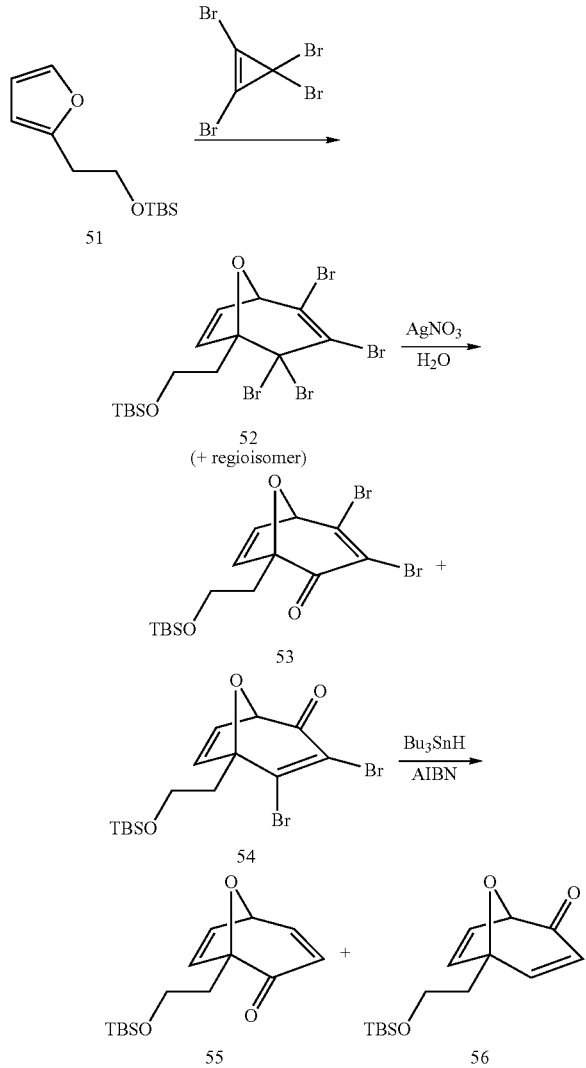

Cyclocondensation of TBCP and 51 will give two regioisomeric tetrabromides 52 that will be converted to a dibromoenone intermediate through a silver-mediated hydrolysis. Previously, it had been shown that attack of a small nucleophile like water on a presumed allylic cation intermediate gives a mixture (~2:1 when methyl is at the bridgehead, ~5:1 when it is phenyl at the bridgehead) of the regioisomeric ketones which can typically be separated by simple chromatography. It is expected that both ketones 53 and 54 can be prepared in scale. It has also known that the parent derivative can be easily obtained by radical debromination under standard conditions. The dibromoenone gives quite a few options for parallel derivitization. For example, the enones 55 and 56 can be generated. Conversion of these two regioisomeric intermediates to the key starting scaffolds will follow by analogy to the azabridged systems (see Scheme 10).

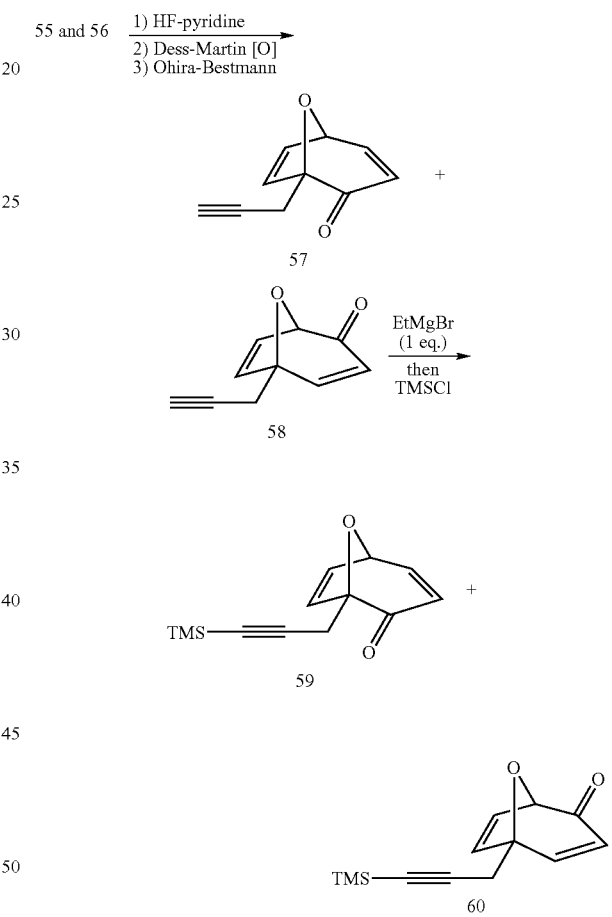

Removal of the silyl group, oxidation and alkyne formation leads to the acetylenes 57 and 58 (see Scheme 10). In this series, organocuprates can be employed to allow for a diversification step. Should the terminal acidic acetylene not be compatible with the reagents used in the previous step(s), TMS can be added to protect this acidic hydrogen. Alternatively, should the unprotected alkyne not need protection, then the incorporation of TMS will be eliminated. Modeling of these compounds in the active site of BaDHFR showed that the three carbon bridge is highly flexible and that both endo and exo-substituents are likely to provide favorable contacts with the enzyme. Both isomers can be explored (see Scheme 11).

Scheme 11. Diversification of oxabridged scaffolds.

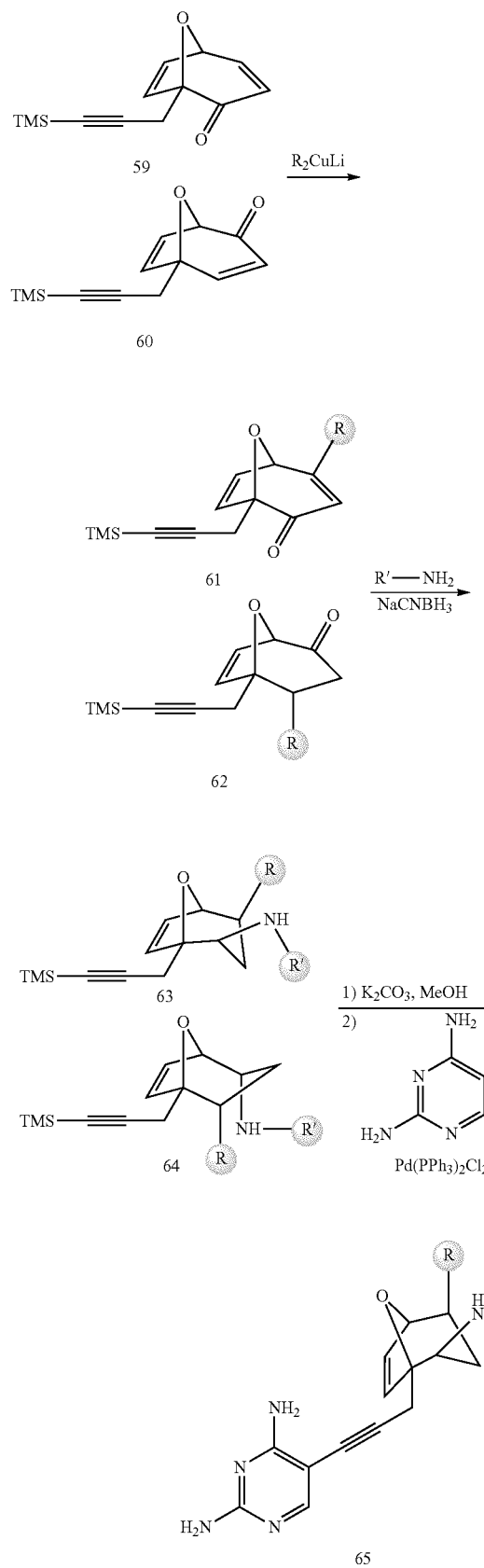

Addition of a cuprate reagent to the β-position of the enone will be controlled by the local steric environment such that addition to 59 is favored on the generally more accessible exo-face while in 60, addition is guided by interference from the bridgehead substituent such that an endo-mode should be observed. A second parallel diversification step through reductive amination of the ketone is controlled by the same factors to give intermediates 63 and 64 where diversity is positioned on opposite faces of the three carbon bridge. Final conversion to the analogs can attained by deblocking of the acetylene followed by standard Sonagashira coupling to furnish the lead series exemplified by 65 and 66.

Carbabridged Library

Figure 7:
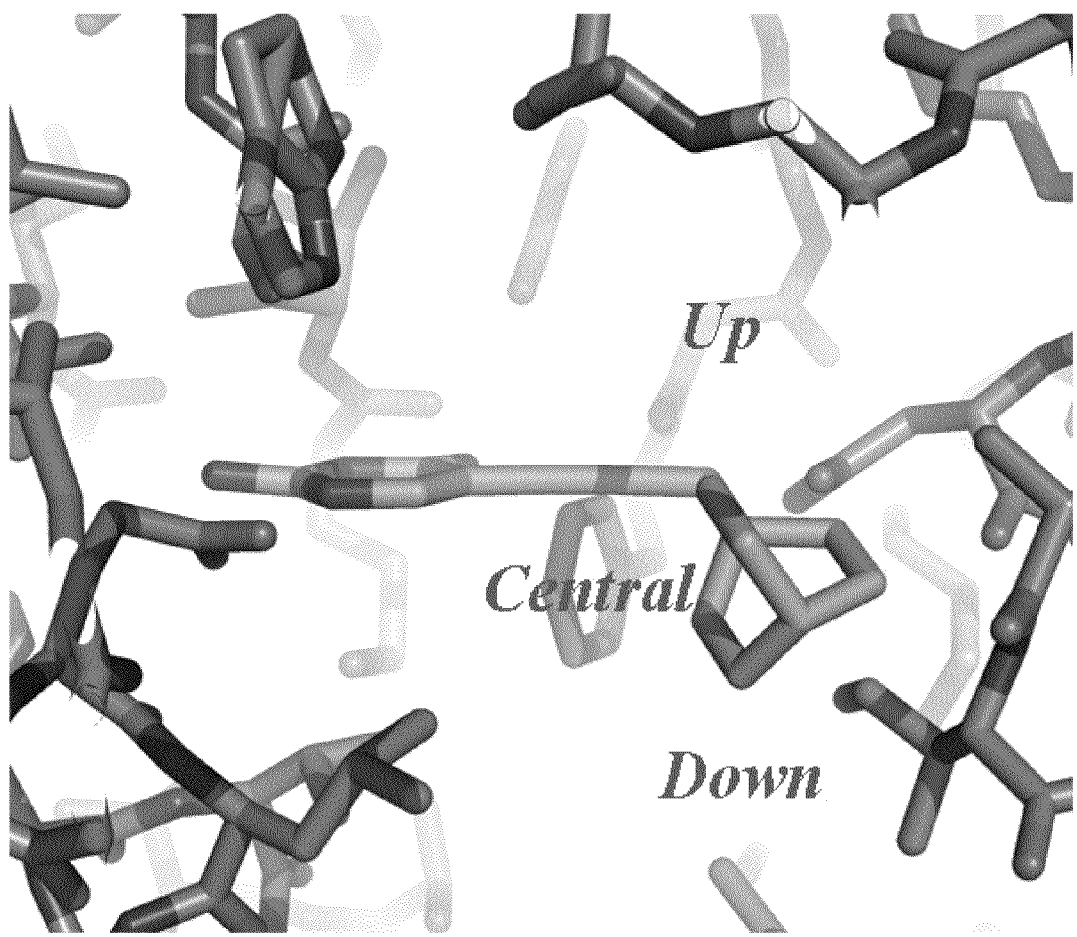

In an embodiment, the bicyclo[2.2.2]octane can be generated. This relatively rigid and compact bicyclic system possesses a higher degree of internal symmetry than the previous bicyclic scaffolds. Modeling studies suggest that one bridge can remain unsubstituted, while the other two bridges can be substituted in varying patterns (FIG. 7).

Three related scaffolds can be prepared from a common keto derivative that is available by slight modification of known routes (see Scheme 12).

Scheme 12. Synthesis of key bicyclo[2.2.2]octane core structures

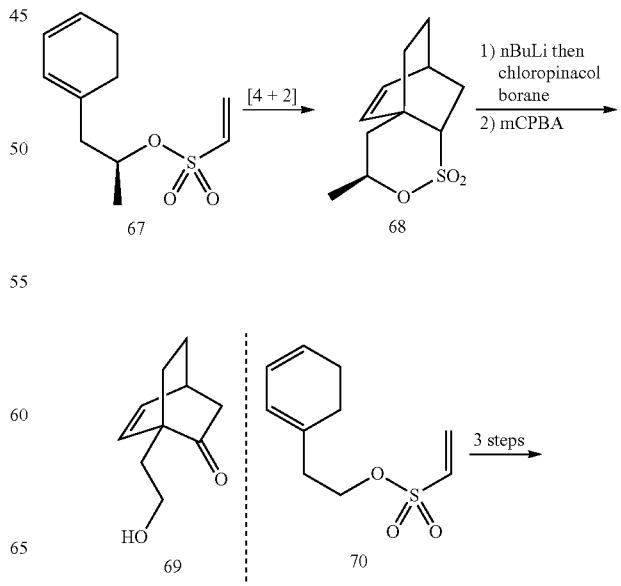

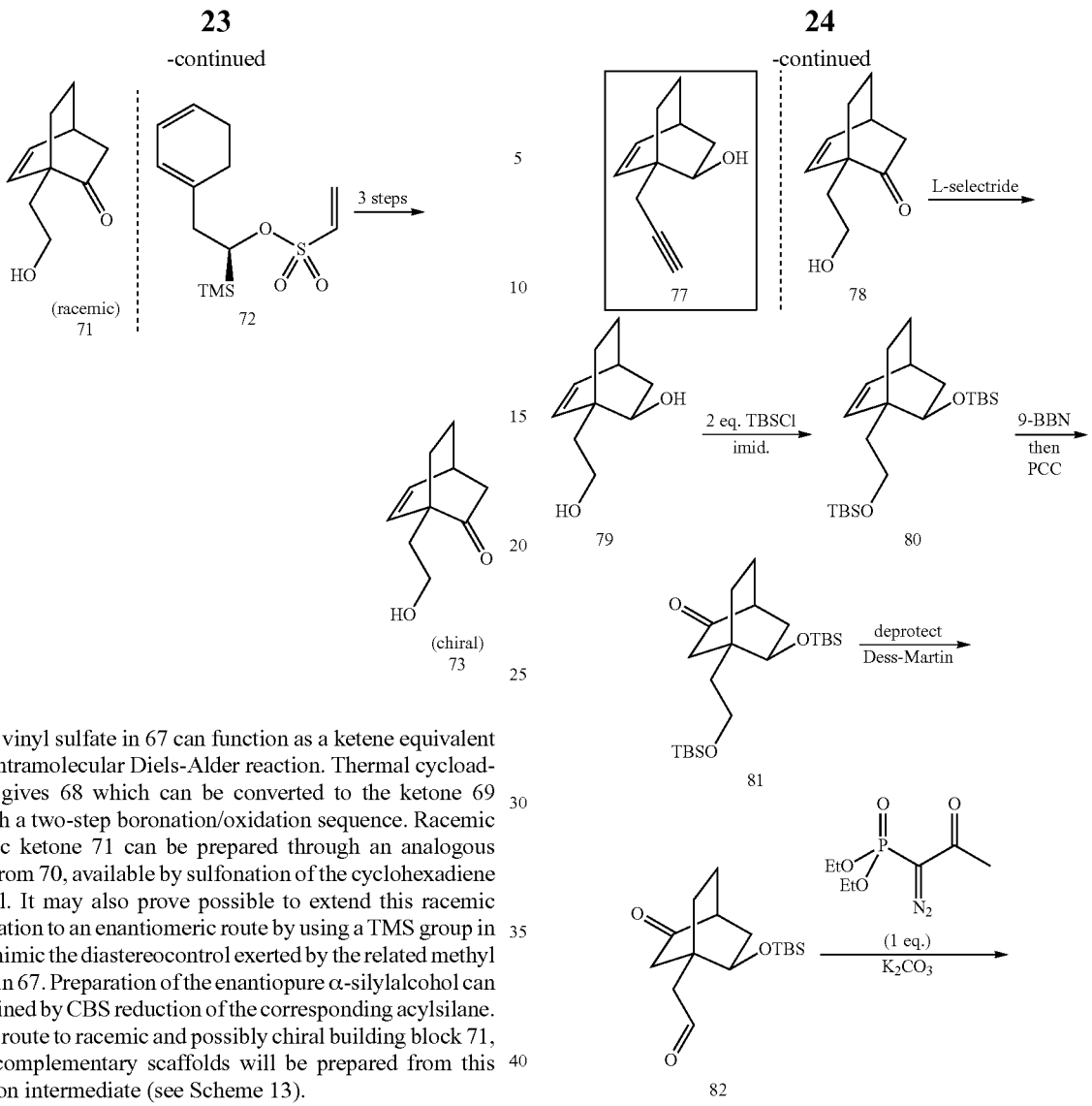

The vinyl sulfate in 67 can function as a ketene equivalent in an intramolecular Diels-Alder reaction. Thermal cycloaddition gives 68 which can be converted to the ketone 69 through a two-step boronation/oxidation sequence. Racemic bicyclic ketone 71 can be prepared through an analogous route from 70, available by sulfonation of the cyclohexadiene ethanol. It may also prove possible to extend this racemic preparation to an enantiomeric route by using a TMS group in 72 to mimic the diastereocontrol exerted by the related methyl group in 67. Preparation of the enantiopure α-silylalcohol can be attained by CBS reduction of the corresponding acylsilane. With a route to racemic and possibly chiral building block 71, three complementary scaffolds will be prepared from this common intermediate (see Scheme 13).

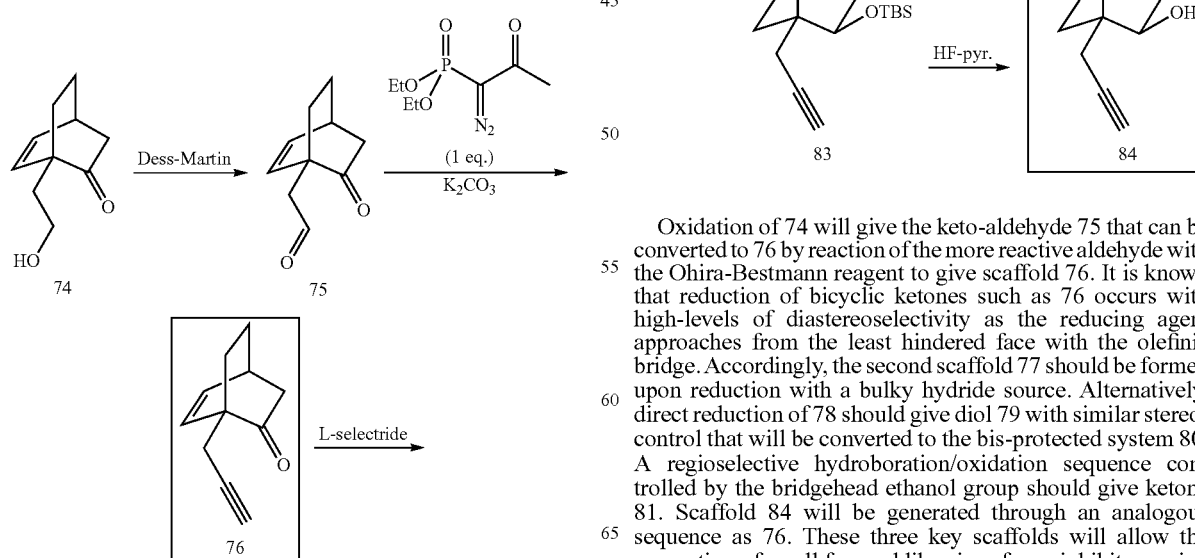

Scheme 13. Synthesis of carbabridged scaffolds

Oxidation of 74 will give the keto-aldehyde 75 that can be converted to 76 by reaction of the more reactive aldehyde with the Ohira-Bestmann reagent to give scaffold 76. It is known that reduction of bicyclic ketones such as 76 occurs with high-levels of diastereoselectivity as the reducing agent approaches from the least hindered face with the olefinic bridge. Accordingly, the second scaffold 77 should be formed upon reduction with a bulky hydride source. Alternatively, direct reduction of 78 should give diol 79 with similar stereocontrol that will be converted to the bis-protected system 80. A regioselective hydroboration/oxidation sequence controlled by the bridgehead ethanol group should give ketone 81. Scaffold 84 will be generated through an analogous sequence as 76. These three key scaffolds will allow the generation of small focused libraries of new inhibitors using rather brief diversification procedures (see Scheme 14).

Scheme 14. Diversification stratgey for hydroxy-ketones

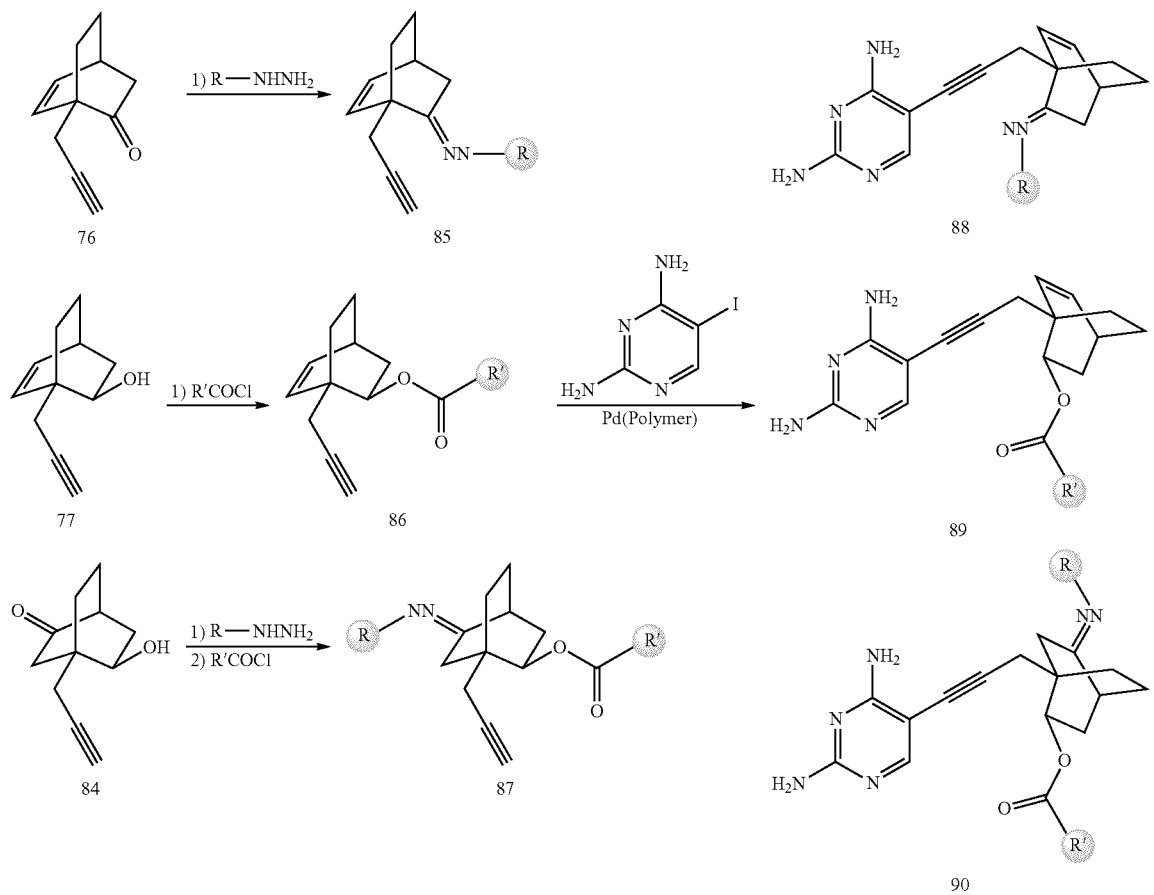

Diversification of these scaffolds can be attained by using the orthogonality of the hydroxyl and keto groups. Diversification of the keto group will occur by condensation with diverse hydrazines, sulfonylhydrazines and acylhydrazines using resin capture to remove excess reagents. Standard acylation procedures will be used to elaborate the alcohol functionality. Final attachment to the diaminopyrimidine completes the route to analog families 88-90.

In an embodiment, compounds of the compositions and methods described herein include the compounds as shown below in Table 1.

TABLE 1

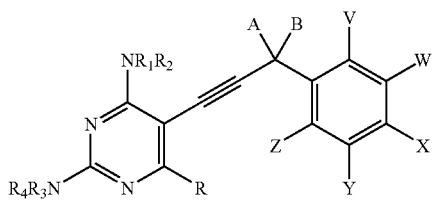

| Compound No. | R | $R_1$ | $R_2$ | $R_3$ | $R_4$ | A | B | V | W | X | Y | Z |
|---|---|---|---|---|---|---|---|---|---|---|---|---|
| 14 | H | H | H | H | H | H | H | H | $OCH_3$ | $OCH_3$ | $OCH_3$ | H |
| 16 | $CH_3$ | H | H | H | H | H | H | H | $OCH_3$ | $OCH_3$ | $OCH_3$ | H |
| 20 | H | H | H | H | H | $CH_3$ | H | H | $OCH_3$ | $OCH_3$ | $OCH_3$ | H |
| 21 | $CH_3$ | H | H | H | H | $CH_3$ | H | H | $OCH_3$ | $OCH_3$ | $OCH_3$ | H |
| 24 | H | H | H | H | H | OH | H | H | $OCH_3$ | $OCH_3$ | $OCH_3$ | H |
| 25 | $CH_3$ | H | H | H | H | OH | H | H | $OCH_3$ | $OCH_3$ | $OCH_3$ | H |
| 127 | H | H | H | H | H | $OCH_3$ | H | H | $OCH_3$ | $OCH_3$ | $OCH_3$ | H |
| 128 | $CH_3$ | H | H | H | H | $OCH_3$ | H | H | $OCH_3$ | $OCH_3$ | $OCH_3$ | H |

TABLE 1-continued

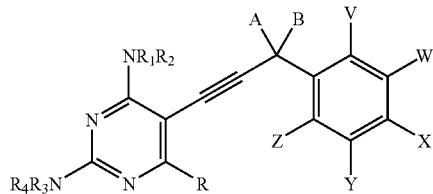

| Compound No. | R | $R_1$ | $R_2$ | $R_3$ | $R_4$ | A | B | V | W | X | Y | Z |
|---|---|---|---|---|---|---|---|---|---|---|---|---|
| 137 (R) | $CH_3$ | H | H | H | H | $CH_3$ | H | H | $OCH_3$ | $OCH_3$ | $OCH_3$ | H |
| 138 (S) | $CH_3$ | H | H | H | H | $CH_3$ | H | H | $OCH_3$ | $OCH_3$ | $OCH_3$ | H |
| 15 | H | H | H | H | H | H | H | $OCH_3$ | H | H | $OCH_3$ | H |
| 17 | $CH_3$ | H | H | H | H | H | H | $OCH_3$ | H | H | $OCH_3$ | H |
| 18 | $CH_3$ | H | H | H | H | H | H | $OCH_3$ | H | H | $OCH_3$ | H |
| 6 | $CH_3CH_2$ | H | H | H | H | H | H | $OCH_3$ | H | H | $OCH_3$ | H |
| 7 | n-propyl | H | H | H | H | H | H | $OCH_3$ | H | H | $OCH_3$ | H |
| 8 | $CH_3$ | H | H | H | H | $CH_3CH_2$ | H | H | $OCH_3$ | $OCH_3$ | $OCH_3$ | H |
| 9 | $CH_3$ | H | H | H | H | $CH_3$ | $CH_3$ | H | $OCH_3$ | $OCH_3$ | $OCH_3$ | H |
| 10 | $CH_3$ | H | H | H | H | $CH_3$ | H | H | $OCH_3$ | H | phenyl | H |
| 11 | $CH_3$ | H | H | H | H | $CH_3$ | H | H | $OCH_3$ | H | 2-Me-phenyl | H |
| 12 | $CH_3$ | H | H | H | H | $CH_3$ | H | H | $OCH_3$ | H | 2,6-Me-phenyl | H |
| 13 | $CH_3$ | H | H | H | H | $CH_3$ | H | H | $OCH_3$ | H | Br | H |
| 116 | $CH_3$ | H | H | H | H | $CH_3$ | H | H | $OCH_3$ | H | phenyl | $OCH_3$ |

Synthesis and experimental data for the above enumerated compounds are provided herein.

In other embodiments of the compositions and methods described herein relate to compounds possessing protozoal activity. Based on the structure of the DHFR enzyme from *C. hominis*, a novel scaffold was developed that led to the discovery of potent and efficient inhibitors of the DHFR enzyme. Initial development of a structure-based drug design approach began with determination of crystal structures of ChDHFR to 2.7 Å resolution. Based on the structure of ChDHFR, a lead series of compounds that maintained good drug-like characteristics and synthetic accessibility were developed, defined by a propargyl linker between a 2,4-diaminopyrimidine ring and aryl ring. One embodiment of a highly efficient ligand with an inhibition constant ($IC_{50}$) of 38 nM and molecular weight of 342 Da is compound X (also referred to herein as UPC111A).

Compound X:

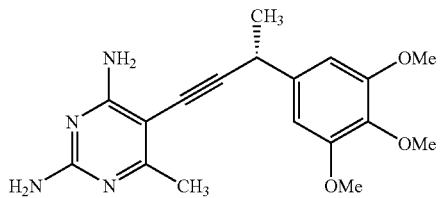

A second generation of propargyl analogs inspired by structural analysis that not only maintained high levels of potency against the parasitic enzyme as observed with the first series of compounds but also exhibited extremely high levels of selectivity were subsequently developed.

Figures 8A, 8B:
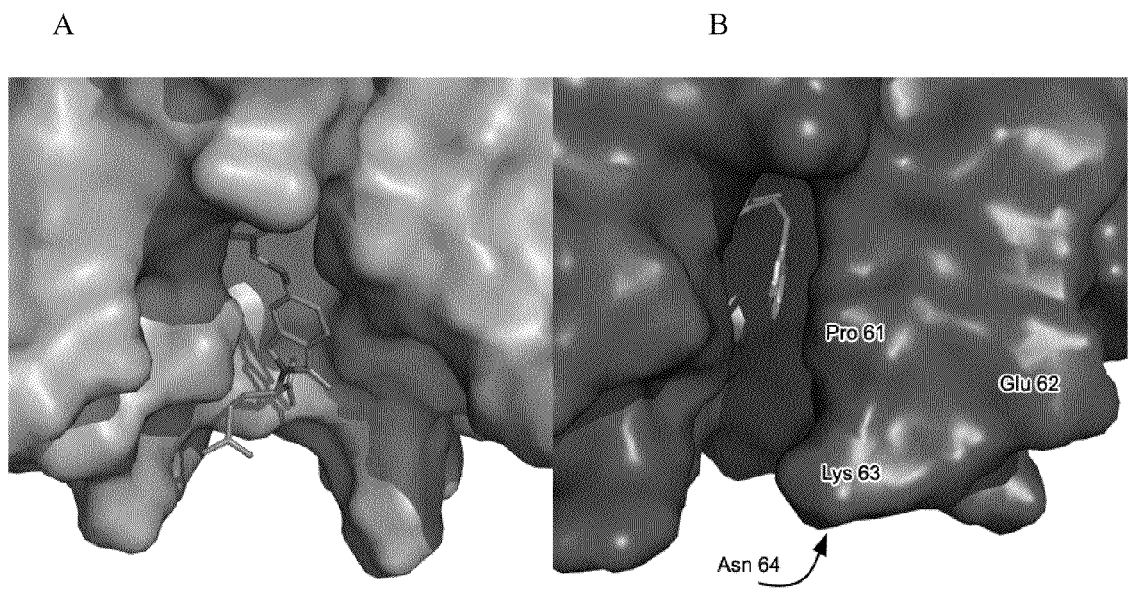

Inspection of the ChDHFR and human DHFR (hDHFR) structures revealed that the active sites are highly homologous and residue differences that exist maintain the same chemical properties. A striking difference between the two enzymes is located at the opening to the active site. In hDHFR, access to the active site is effectively restricted by a four-residue loop (Pro 61, Glu 62, Lys 63, Asn 64 or PEKN loop) that is notably absent in ChDHFR (see FIG. 8). By exploiting the structural differences between the two enzymes, ligands with selectivity for ChDHFR were designed.

Initial structural analysis with the first generation propargyl inhibitors showed that lead compound X did not appear to exploit the above structural differences. Indeed, compound X showed only a 8-fold preference for the parasitic enzyme over the human enzyme (see Table 3). Examination of the structures of ChDHFR and hDHFR led to two biphenyl series of derivatives in which the second aryl ring was installed at the 5' or 4' position of the proximal aryl ring.

Inspection of docked complexes of the lead compound in ChDHFR and hDHFR suggested that functionality projecting from the 3' or 4' position on the aromatic core of compound X would be correctly poised to interact with a region of space filled by the PEKN loop in hDHFR. The overall strategy for adding steric substitutions to the 3' or 4' positions of the initial lead compound is shown in Scheme 15. By predicting steric substitutions at these positions it was possible to specifically stabilize or destabilize interactions with the loop region. Accordingly, it was found that particular steric interactions destabilize binding to the human enzyme, maintain high potency against the protozoal form, while also probing the degree of flexibility of the residues in the active site. The newly designed analogs maintained three moieties: one, the methyl at C6 of the pyrimidine, which is predicted to interact with Phe 36, Leu 33 and Leu 25; two, the propargyl methyl, which is predicted to interact favorably with residues Thr 58 and Ile 62; and three, the 3' methoxy group, predicted to interact with both the backbone and side chain of Leu 25 in the active site.

Computational analysis of the biphenyl series led to the synthesis of eight new compounds, all of which exhibit improved potency and selectivity (see Table 3). The racemic 5'-biphenyl analog was the most potent and selective of the racemic compounds, with the single R enantiomer being the most potent and selective compound overall. Furthermore, combining additional elements into the initial lead compound resulted in the development of highly selective compounds.

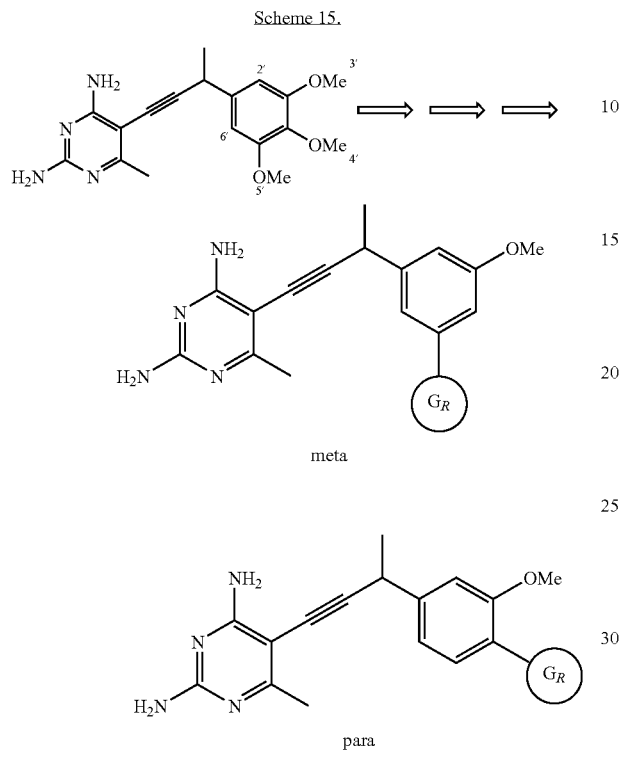

meta para

A direct method for introducing steric bulk onto the aromatic core region was required for synthesis of the second generation DHFR inhibitors. A biaryl type of scaffold where steric bulk would be introduced in the form of an additional aromatic ring was utilized. The biaryl scaffold provided flexibility and versatility offered by Suzuki cross-coupling for the preparation of a wide range of potential inhibitors.

Analog families that varied both the placement and substitution pattern of the second aryl ring were created virtually and docked into both ChDHFR and hDHFR using the program, Surflex (Tripos, Inc) in the Sybyl environment. Surflex-Dock flexibly docks ligands to a protomol representation of the active site, created by probing the active site with small molecular fragments. Ligands are fragmented and built into the protomol based on an empirical scoring function that includes hydrophobic, polar, repulsive, entropic and solvation terms. In order to explore protein flexibility, ensembles of receptor structures were created based on minimized conformational snapshots across a molecular dynamics time course; scores were averaged over the ensemble. Docking scores are returned with an associated "crash value" that largely approximates the penetration of the ligand into the receptor. "Crash values" that are closer to 0 are preferred.

Employing these computational methods, a series of eight potential inhibitors were evaluated. Four of the potential inhibitors were in the 5' series of inhibitors and four were in the 4' series (see FIG. 10). Each series was comprised of derivatives that incorporated increasing steric bulk at the ortho positions of the second aryl ring. Computational analysis predicted that the crash values against hDHFR for these inhibitors became increasingly negative as the steric volume of the second aryl ring increased with minimal change in ChDHFR. For example, a compound with an unsubstituted aryl ring yielded a crash value of −1.31 in ChDHFR and −2.79 in hDHFR. An analogous compound with isopropyl groups in both ortho positions yielded increased crash values of −4.08 and −12.76 in ChDHFR and hDHFR, respectively.

The selection of a biaryl-based scaffold in second-generation inhibitors was partially driven by the reliability of Suzuki coupling in assembling sterically demanding biphenyls. The 5'-linked biphenyl analogs were accessed by selective functionalization of commercially available 3,5-dibromoanisole 4 (see Scheme 16).

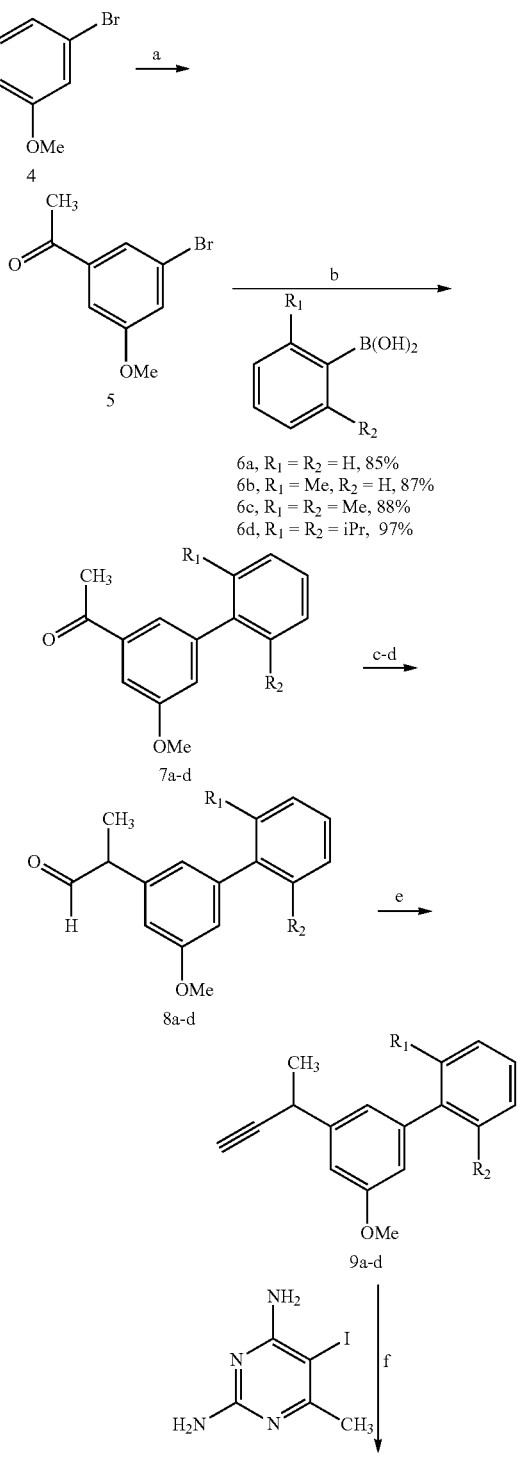

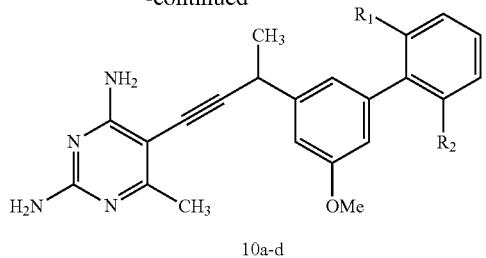

10a-d a) nBuLi, -78° C. then CH₃C(O)N(CH₃)₂, 71%;
b) Pd(Ph₃)₂Cl₂, Cs₂CO₃, dioxane;
c) Ph₃P = CHOMe, THF;
d) conc. HCl, THF, reflux 57-82% for two steps;
e) dimethyl (1-diazo-2-Oxopropyl)phosphonate, K₂CO₃, MeOH 64-99%;
f) Pd(PH₃)₂Cl₂, CuI, Et₃N, DMF 67-94%.

Metal-halogen exchange followed by addition of N,N-dimethylacetamide gave acetophenone derivative 5 which was cross-coupled with four arylborinic acid derivatives 6a-d resulting in corresponding biphenyl derivatives 7a-d. The di-isopropyl boronic acid 6d was not previously known but was easily prepared from 2,6-diisopropylaniline by diazotization, iodination and final conversion to boronic acid via lithiation/boronation. Homologation of the acetyl moiety by condensation with a methoxy substituted phosphorous ylide and hydrolysis of the resulting enolether gave aldehydes e8a-d in very good yield. Condensation with the Ohira-Bestmann reagent gave the corresponding terminal acetylenes 9a-d that were converted to inhibitors 10a-d by a final Sonagashira coupling with iodopyrimidine 11.

The 4'-linked biphenyl analogs were accessed through a similar route from the commercially available benzoic acid derivative 12. Conversion of the acid to acyl chloride and treatment of the crude material with Gilman reagent produced an excellent yield of the acetophenone 13 (See Table 2). The acetyl group was homologated through a series of identical reactions as outlined previously to arrive at the inhibitor series. Biphenyl functionality was installed via Suzuki coupling as per the 5'-linked series.

In another embodiment, the compositions and methods described herein relate to compounds possessing antifungal activity. A series of lead compounds were prepared by analyzing the structure of DHFR from a parasitic protozoan, *Cryptosporidium hominis* (ChDHFR), and are characterized by a propargyl-based linker between the pyrimidine and substituted aryl ring. The propargyl linker extends the distance between the pyrimidine and aryl rings, relative to trimethoprim, allowing the aryl ring to fit more optimally in a hydrophobic pocket of the DHFR enzyme.

While the structure of *C. glabrata* DHFR (CgDHFR) had not yet been determined, a comparison of a homology model of CgDHFR, based on the structure of *C. albicans* (CaDHFR) and ChDHFR suggested that the propargyl-linked inhibitors may also serve as potential antifungal lead compounds. In fact, in a homology model of CgDHFR, the hydrophobic pocket occupied by the aryl ring is displaced an additional 2 Å from the pyrimidine ring, suggesting that the extended compounds may be even more effective in CgDHFR than in ChDHFR.

Analysis of the structure revealed the detail of interactions between the ligand and the enzyme and also revealed a hydrophobic region flanked by residues in a loop near the active site where additional binding interactions can be exploited for increased inhibitor potency and selectivity. After expressing and purifying CgDHFR, inhibition constants (IC₅₀) for eleven propargyl-linked compounds based on two different scaffolds were measured in enzyme assays (Table 2). Many of the compounds were very potent inhibitors of CgDHFR with IC₅₀ values less than 100 nM; four inhibitors (Compounds 5, 6, 9, 11) have IC₅₀ values equal to or less than 25 nM. Moreover, when the propargyl compounds were assayed with human DHFR, selectivity ratios as high as 156-fold (Table 2) were observed.

TABLE 2

Enzyme inhibition and antifungal assay results for propargyl-linked inhibitors

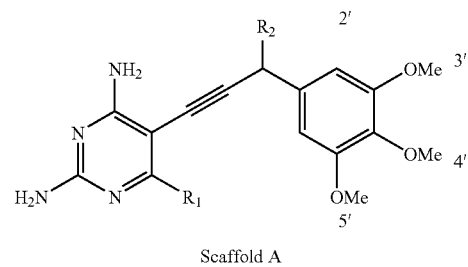

Scaffold A

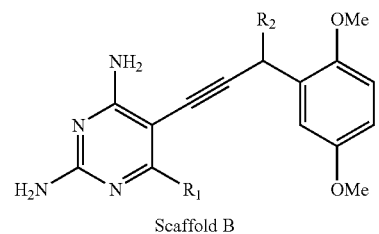

Scaffold B

| Compound | Scaffold type | $R_1$ | $R_2$ | CgDHFR IC₅₀ (nM) | hDHFR IC₅₀ (nM) | Selectivity (h/CgDHFR) | Antifungal activity MIC (μg/mL) |
|---|---|---|---|---|---|---|---|
| 1 | A | H | H | 33 | 1460 | 44 | Inact* |
| 2 | A | H | CH₃ | 36 | 1460 | 40.6 | Inact |

TABLE 2-continued

Enzyme inhibition and antifungal assay results for propargyl-linked inhibitors

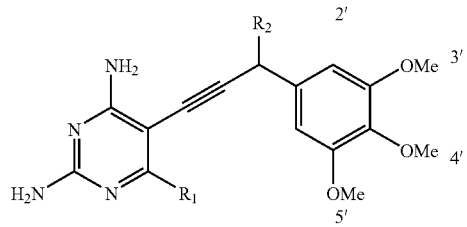

Scaffold A

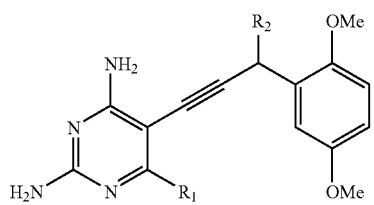

Scaffold B

| Compound | Scaffold type | R₁ | R₂ | CgDHFR IC₅₀ (nM) | hDHFR IC₅₀ (nM) | Selectivity (h/CgDHFR) | Antifungal activity MIC (µg/mL) |
|---|---|---|---|---|---|---|---|
| 3 | A | H | OH | 2700 | 14300 | 5.3 | 328 |
| 4 | A | H | OMe | 450 | 1160 | 2.6 | Inact |
| 5 | A | CH₃ | H | 17 | 400 | 23.5 | 20 |
| 6 | A | CH₃ | CH₃ | 25 | 1380 | 55.2 | 21 |
| 7 | A | CH₃ | OH | 39 | 5710 | 146 | Inact |
| 8 | A | CH₃ | OMe | 30 | 1220 | 40.7 | Inact |
| 9 | B | H | H | 21 | 3200 | 152 | 71 |
| 10 | B | CH₃ | H | 32 | 1300 | 40.6 | 56 |
| 11 | B | Et | H | 8.2 | 1280 | 156 | 78 |

*Inact: not active at 2 mM (~600 µg/mL)

The compounds were then tested as antifungal agents in an antifungal assay against *C. glabrata*. Several of the compounds, in particular compounds 5 and 6 of Table 2, exhibited antifungal properties.

Using the above structural information, a second generation of CgDHFR inhibitors were designed that resulted in subnanomolar potency and very high levels of selectivity toward the *C. glabrata* enzyme. The second generation of CgDHFR inhibitors were also found to kill *C. glabrata* in culture at concentrations that mirror those of clinically used antifungal agents.

Pharmaceutical Compositions

Pharmaceutical compositions containing the compounds as disclosed above combined with one or more pharmaceutically acceptable diluents, excipients, carriers, or delivery systems are provided. One or more of the compounds can be prepared in a physiologically acceptable formulation, such as in a pharmaceutically acceptable carrier, using known techniques. For example, the compound is combined with a pharmaceutically acceptable excipient to form a therapeutic composition.

In another embodiment, the compositions provided herein can be administered together with, or in addition to, sulfa compounds to form therapeutic pharmaceutical compositions. It is recognized in the art that sulfa compounds exhibit high activity against pathogenic bacteria. Non-limiting examples of sulfa compounds and the processes by which the sulfa compounds are made is provided in U.S. Pat. No. 3,091,610, which is herein incorporated by reference in its entirety for all purposes.

The compositions provided herein may be administered in the form of a solid, liquid or aerosol. Examples of solid compositions include pills, creams, and implantable dosage units. Pills may be administered orally. Therapeutic creams may be administered topically. Implantable dosage units may be administered locally, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal or parenteral (for example, intravenous, subcutaneous, or intramuscular) routes. In addition, the composition may be incorporated into a sustained release matrix or matrices such as biodegradable polymers, the polymers being implanted in the vicinity of where delivery is desired. The method includes administration of a single dose, administration of repeated doses at predetermined time intervals, and sustained administration for a predetermined period of time.

A sustained release matrix, as used herein, is a matrix made of materials, usually polymers that are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It should be understood that in addition to the ingredients particularly mentioned above, the formulations of the present invention may include other agents conventional in the art having regard to the type of formulation in question.

The dosage of the composition will depend on the progression of infection or cancer, the particular composition used, and other clinical factors such as weight and condition of the patient, and the route of administration.

Methods of Treatment

Methods of treating bacterial, fungal and protozoal infections and cancer using the compounds described herein are provided. In accordance with the methods, one or more of the pharmaceutical compositions described above, containing a therapeutically effective concentration of compound, is administered to an individual in need of treatment.

The DHFR inhibitory compounds described herein are potent and selective for many different pathogenic organisms, including, but not limited to, the DHFR enzyme from bacteria such as *Bacillus anthracis* and methicillin-resistant *Staphylococcus aureus*, fungi such as *Candida glabrata, Candida albicans* and *Cryptococcus neoformans* and protozoa such as *Cryptosporidium hominis* and *Toxoplasma gondii*. These compounds and other similar compounds are also potent against the mammalian enzyme and may be useful as anti-cancer therapeutics. In other words, the compounds of the present invention have been shown to have strong activity in vitro against the mammalian enzyme and some of the compounds of the present invention have been shown to have activity against mammalian cell lines. Specifically, inhibitor compound 5-[3-(3-methoxy-2'6'-diisopropylbiphenyl-4-yl)but-1-yn-1-yl]-6-methylpyrimidine-2,4-diamine has been shown to display mammalian cell toxcity and may be useful as an anti-cancer therapeutic.

Treatment of a patient having a bacterial, fungal and protozoal disease or cancer can be accomplished by administering to the patient a pharmaceutically acceptable composition containing one of more of the compounds described, as described herein, at an effective dosage. Effective results may be obtained with a single dose. Multiple doses may be necessary to achieve optimal and sustained benefits. The compounds can be provided as substantially purified compositions or placed in pharmaceutically acceptable formulations or delivered for sustained release using formulations and methods known to those of ordinary skill in the art as described above. These formulations can be administered by standard routes. In general, the compositions may be administered various routes (e.g., intravenous, transdermal, intraperitoneal, intraspinal, subcutaneous or intramuscular) as described above.

The effective dosage of one or more of the pharmaceutical compositions provided herein will depend on the disease state or condition being treated and other clinical factors such as weight and condition of the animal or human and the route of administration. Depending upon the half-life of the compound in the particular animal or human, it can be administered between several times per day to once a month or less. The methods described herein contemplate single as well as multiple administrations, given either simultaneously or over an extended period of time.

It is to be understood that the methods provided herein have applications for both human, mammalian and veterinary use. It is also to be understood that the term "individual" as used herein refers to an animal, human, mammal or patient in need of treatment using the compounds described herein.

In an embodiment for the treatment of a bacterial infection, a pharmaceutically acceptable amount of the compound of formula I or a pharmaceutical acceptable salt thereof is administered to an individual, wherein formula I is

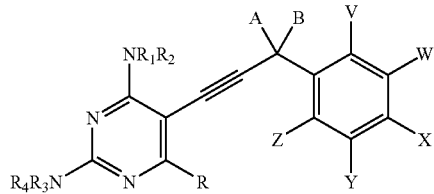

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-5}$alkyl, cycloalkyl, alkoxyalkyl, arylalkyl, alkylcarbonyl, cycloalkylcarbonyl, alkoxycarbonyl, alkoxyalkylcarbonyl, alkoxyalkoxyalkylcarbonyl, arylcarbonyl, pyridinylcarbonyl, aryloxyalkyl, haloalkylcarbonyl, and cyanoalkylcarbonyl;

A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

A and B together with the carbon to which they are connected can form a ring of from 3 to 7 members wherein the ring members are selected form the group consisting of alkylene, alkenylene, and alkynylene, wherein any of the alkylene, alkenylene, and alkynylene groups may optionally be interrupted by one or more heteroatoms selected from the group consisting of O, N, S, and Se and the alkylene or alkenylene may be optionally substituted with one or more of $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

V, W, X, Y, and Z are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups is preferably $C_1$ to $C_6$.

In one embodiment at least one of V, W, X, Y and Z is a methoxy group. In another embodiment all of W, X, and Y are methoxy groups. In another embodiment at least one of V and Y is a methoxy group. In another embodiment both V and Y are methoxy groups. In another embodiment at least one of A and B is not $C_{1-5}$ alkyl.

In an embodiment for the treatment of a fungal infection, a pharmaceutically acceptable amount of the compound of formula I or a pharmaceutical acceptable salt thereof is administered to an individual, wherein formula I is

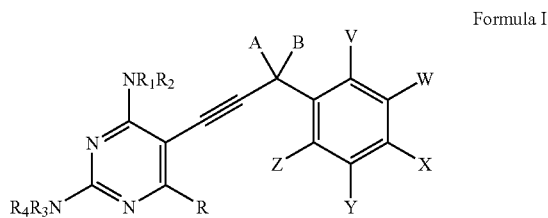

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-5}$alkyl, cycloalkyl, alkoxyalkyl, arylalkyl, alkylcarbonyl, cycloalkylcarbonyl, alkoxycarbonyl, alkoxyalkylcarbonyl, alkoxyalkoxyalkylcarbonyl, arylcarbonyl, pyridinylcarbonyl, aryloxyalkyl, haloalkylcarbonyl, and cyanoalkylcarbonyl;

A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

A and B together with the carbon to which they are connected can form a ring of from 3 to 7 members wherein the ring members are selected form the group consisting of alkylene, alkenylene, and alkynylene, wherein any of the alkylene, alkenylene, and alkynylene groups may optionally be interrupted by one or more heteroatoms selected from the group consisting of O, N, S, and Se and the alkylene or alkenylene may be optionally substituted with one or more of $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

V, W, X, Y, and Z are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups is preferably $C_1$ to $C_6$.

In one embodiment at least one of V, W, X, Y and Z is a methoxy group. In another embodiment all of W, X, and Y are methoxy groups. In another embodiment at least one of V and Y is a methoxy group. In another embodiment both V and Y are methoxy groups. In another embodiment at least one of A and B is not $C_{1-5}$ alkyl.28.

In an embodiment for the treatment of a protozoal infection, a pharmaceutically acceptable amount of the compound of formula I or a pharmaceutical acceptable salt thereof is administered to an individual, wherein formula I is

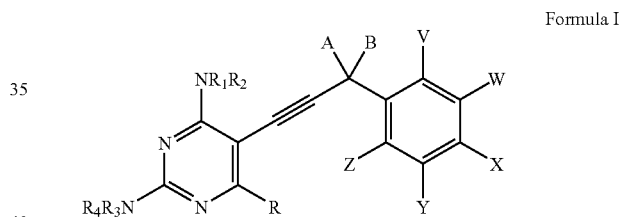

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-5}$alkyl, cycloalkyl, alkoxyalkyl, arylalkyl, alkylcarbonyl, cycloalkylcarbonyl, alkoxycarbonyl, alkoxyalkylcarbonyl, alkoxyalkoxyalkylcarbonyl, arylcarbonyl, pyridinylcarbonyl, aryloxyalkyl, haloalkylcarbonyl, and cyanoalkylcarbonyl;

A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

A and B together with the carbon to which they are connected can form a ring of from 3 to 7 members wherein the ring members are selected form the group consisting of alkylene, alkenylene, and alkynylene, wherein any of the alkylene, alkenylene, and alkynylene groups may optionally be interrupted by one or more heteroatoms selected from the group consisting of O, N, S, and Se and the alkylene or alkenylene may be optionally substituted with one or more of $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

V, W, X, Y, and Z are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups is preferably $C_1$ to $C_6$.

In one embodiment at least one of V, W, X, Y and Z is a methoxy group. In another embodiment all of W, X, and Y are methoxy groups. In another embodiment at least one of V and Y is a methoxy group. In another embodiment both V and Y are methoxy groups. In another embodiment at least one of A and B is not $C_{1-5}$ alkyl.

In an embodiment for the treatment of a protozoal infection, a pharmaceutically acceptable amount of the compound of formula I or a pharmaceutical acceptable salt thereof is administered to an individual, wherein formula I is as indicated above.

In an embodiment for the treatment of cancer, a pharmaceutically acceptable amount of the compound of formula I or a pharmaceutical acceptable salt thereof is administered to an individual, wherein formula I is

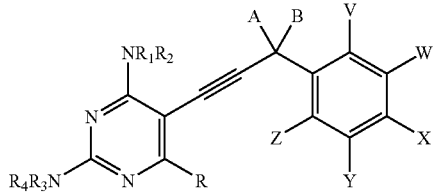

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-15}$alkyl, cycloalkyl, alkoxyalkyl, arylalkyl, alkylcarbonyl, cycloalkylcarbonyl, alkoxycarbonyl, alkoxyalkylcarbonyl, alkoxyalkoxyalkylcarbonyl, arylcarbonyl, pyridinylcarbonyl, aryloxyalkyl, haloalkylcarbonyl, and cyanoalkylcarbonyl;

A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

A and B together with the carbon to which they are connected can form a ring of from 3 to 7 members wherein the ring members are selected form the group consisting of alkylene, alkenylene, and alkynylene, wherein any of the alkylene, alkenylene, and alkynylene groups may optionally be interrupted by one or more heteroatoms selected from the group consisting of O, N, S, and Se and the alkylene or alkenylene may be optionally substituted with one or more of $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups means $C_1$ to $C_6$ alkyl;

V, W, X, Y, and Z are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein "lower" used in conjunction with any of the above groups is preferably $C_1$ to $C_6$.

In one embodiment at least one of V, W, X, Y and Z is a methoxy group. In another embodiment all of W, X, and Y are methoxy groups. In another embodiment at least one of V and Y is a methoxy group. In another embodiment both V and Y are methoxy groups. In another embodiment at least one of A and B is not $C_{1-5}$ alkyl.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Enzyme Expression, Purification, and Assays

ChDHFR: ChDHFR-TS was expressed in *E. coli* and purified using a methotrexate agarose column (Sigma).

hDHFR: The gene for hDHFR was amplified using PCR from cDNA obtained from ATCC. The gene was inserted in a pET41 vector with a C-terminal histidine tag for affinity chromatography. The resulting construct was verified by sequencing. The hDHFR protein was expressed in *E. coli* and purified using a nickel affinity column.

TgDHFR: DHFR cloned from *T. gondii* DHFR-TS was determined to be insoluble after refolding at relatively low protein concentrations (>1 mg/mL). The presence of an unstructured loop region (residues 43-70) that is not present in other DHFR proteins was predicted to render the protein insoluble. These residues were removed, leaving a five residue loop region characteristic of several other species of DHFR. The removal of this unstructured loop region yielded a soluble preparation of TgDHFR at concentrations in excess of 18 mg/mL, a single species by native gel electrophoresis and with an activity level equal to *T. gondii* DHFR-TS and characteristic of other DHFR proteins after refolding.

CgDHFR: The gene coding CgDHFR was amplified by PCR from *C. glabrata* genomic DNA obtained from ATCC. The gene was inserted in a pET41 vector that includes a C-terminal histidine tag for nickel affinity chromatography. *E. coli* cells were transformed and the resulting plasmid was verified by sequencing. The protein was expressed in *E. coli* BL21(DE3) cells with isopropyl β-D-thiogalactoside induction. Following growth, the cells were lysed with BugBuster (Novagen) and centrifuged; the supernatant was loaded on a Ni-NTA column. The column was washed with 20 mM Tris (pH 8.0)/0.4 M NaCl and the protein was eluted using a gradient of 20 mM Tris (pH 8.0), 0.3 M NaCl, 20% glycerol, 0.1 mM EDTA, 2 mM DTT, 250 mM imidazole. Fractions containing CgDHFR were identified by SDS-PAGE, combined and desalted using a PD-10 column with a buffer containing 20 mM Tris pH 8.0, 20% glycerol, 0.1 mM EDTA and 2 mM DTT. The protein was concentrated to 13 mg/mL.

Enzyme activity assays were performed 25° C. by monitoring the change in UV absorbance at 340 nm in a solution containing 50 mM tris(hydroxymethyl)methyl-2-aminoethanesulfonic acid pH 7.0, 1 mM EDTA, 75 µM 2-mercaptoethanol, 1 mg/mL bovine serum albumin, 1 mM dihydrofolate (Eprova), and 100 µM nicotinamide adenine dinucleotide phosphate (NADPH) (Sigma) and limiting concentrations of enzyme. Enzyme and inhibitor were allowed to incubate for 5 min before adding dihydrofolate to initiate the reaction. Enzyme assays were performed at least four times. $IC_{50}$ values and their standard deviations were calculated in the presence of varying concentrations of inhibitor near the $IC_{50}$ concentration. Standard deviations are within 10% of the reported value.

Antifungal assays were performed using *C. glabrata* as a suspension in 50% glycerol at −78° C. For susceptibility testing, a streak of stock culture was made on SDA agar and grown at 30° C. for 48 h. One pure colony of the test organism was recovered from the plate, suspended in appropriate media and grown in a 5 mL shake flask culture. A sample of the shake flask culture was diluted to $1\times10^5$ cells/mL in media and added to 96-well test plates (100 µL per well) containing test compounds dispensed in DMSO (1 µL). Amphotericin and ketoconazole were used as controls. After an incubation period determined from the strain specific doubling time, Alamar Blue (10 µL) was added, allowed to incubate; each well was scored for dye reduction. The MIC value was taken as the lowest concentration of test compound that inhibits growth such that less than 1% reduction of the blue resazurin ($\lambda_{max}$ 570 nm) component of the Alamar Blue to the pink resorufin ($\lambda_{max}$ 600 nm) was observed.

Calculation of Ligand Efficiency

Ligand efficiency is expressed as binding energy per non-hydrogen atom (¢G/Nnon-hydrogen atoms) where ΔG) −RT ln Kd, although $IC_{50}$ values can be substituted for Kd.9 Therefore, ligand efficiencies were calculated using the quotient of ¢G) (1.99 cal K$^{-1}$ mol$^{-1}$)(300 K) (ln $IC_{50}$)(0.001 kcal/cal) and the number of non-hydrogen atoms.

Computational Modeling

All ligands were created in Sybyl (Tripos, Inc.) and checked for correct geometries. These were selectively protonated at N I of the 2,4-diaminopyrimidine ring. Formal charges were calculated automatically.

Ensembles of receptors were used to model protein flexibility. Receptors were prepared by adding hydrogens, removing waters and calculating formal charges. Ensemble sets were created by taking 500 fs conformational snapshots across a 10000 fs molecular dynamics run at 300 K using the Amber Force Field in Sybyl. All structures were then brought to their local energy minima with a 1000 iteration energy change gradient, under the assumption that high-energy conformations are not likely to be the bioactive ones. Mobility was limited to a specific active site, as defined by all atoms falling within a sphere of a specific radius around the co-crystallized ligand. For ChDHFR, the structure 1SEJ was used with a 6 Å sphere around the tricyclic core of the ligand defining the active site. 1KMV was used as the hDHFR structure. The unresolved sidechains of Asp 21 and Lys 62 were constructed using the most common sidechain angles from a Lovell dictionary. Motion of 1KMV was confined to a 6 Å sphere around the ligand and PEKN loop region residues 59-68. The conserved acidic residue (Glu 30) was held rigid throughout the MD to preserve the essential N1H hydrogen bonding contact. It was not necessary to hold the conserved acidic residue rigid in the case of ChDHFR as the contact was preserved across the time course.

Docking was carried out using Surflex-Dock as implemented by Sybyl 7.3. Due to the conserved orientation of the 2,4-diaminopyrimidine moiety in the active site, the correct placement of the ligand could be determined. The scores reported are the top scoring poses with this conserved orientation, as determined by the N1H falling within hydrogen bond distance of the conserved acidic residue and the C2 NH$_2$ falling within 4.3 Å of the conserved Thr oxygen to preserve planar orientation of the monocyclic ring. Scores were averaged across the ensemble.

Example 2

Chemistry, Modeling, and Biological Evaluation

Structural Analysis of DHFR from *C. hominis* and *T. gondii*.

The crystal structure of ChDHFR with different ligands has been previously reported, however, to date, there has been no experimentally determined structure of TgDHFR. Homology models of TgDHFR have been created based on the closely related structure of DHFR from *Mus musculus* (PDB ID: 1U7014). The TgDHFR model was minimized, and a Ramachandran analysis showed good morphology conservation such that the backbone geometry fell outside allowed regions for only six residues in loop regions. The model was further validated by docking eleven inhibitors with determined $IC_{50}$ values into the active site and achieving a 50.2% correlation with the measured inhibition constants.

Superpositions of the crystal structure of ChDHFR and the homology model of TgDHFR show that the two enzymes are very similar, both in overall fold and in the identity and arrangement of many active site residues. Surrounding the pteridine ring system of methotrexate, a potent inhibitor modeled into both sites, are residues that are conserved between the two species: an aspartic acid residue (amino acid 32 in Ch, and amino acid 31 in Tg) forms an electrostatic interaction with the protonated N1 and a hydrogen bond with the amino group at position as well as Thr (amino acid 134 in Ch, and amino acid 172 in Tg), Val (amino acid 9 in Ch, and amino acid 8 in Tg) and Phe (amino acid 36 in Ch and amino acid 35 in Tg) that form van der Waals interactions. The linker between the pteridine and the para-aminobenzoic acid (pABA) is surrounded by one conserved Thr (amino acid 58 in Ch and amino acid 83 in Tg) and one nonconserved residue: Cys 113 in Ch and Val 151 in Tg. The pABA ring is bound in a less well-conserved hydrophobic pocket comprised of Ile 62 in Ch (Met 87 in Tg), Leu 67 in Ch (Leu 94 in Tg) and Leu 33 in Ch (Phe 32 in Tg).

In both species, models of TMP show electrostatic and hydrogen bond interactions between the protonated N I and the amino group at the C2 position of the pyrimidine ring and the conserved Asp in the active site. This interaction between the 2,4-diaminopyrimidine and an acidic residue in the active site is conserved across many species of DHFR. However, the linker region of TMP appears to be too short to extend the trimethoxyphenyl ring fully into the hydrophobic pocket normally occupied by the pABA ring of MTX, possibly explaining the lower in vitro potency of TMP against these species. Based on these structural analyses, a relatively simple strategy emerged to increase the potency of TMP for both of the target organisms by extending the length of the linker between the two aromatic rings.

Example 3

Design and Synthesis of Extended TMP Analogues

In order to test the hypothesis that extending the distance between the diaminopyrimidine and phenyl rings of TMP would achieve greater potency against ChDHFR and TgDHFR, the use of a two-carbon linker was explored in place of the single methylene bridge found in TMP. The synthesis of several 5-ethynylpyrimidine derivatives with non-benzyl moieties has been previously reported and these compounds appeared to inhibit *T. gondii* and two species of fungal DHFR. TMP derivatives containing saturated aliphatic, cis and trans-olefinic, or acetylenic linkers were docked into the crystal structure of ChDHFR, chosen because it was determined from experimental data. TMP analogues with rigid olefinic and acetylenic linkers allowed the diaminopyrimidine to dock into the proper orientation but these linkers prevented the trimethoxyphenyl ring from occupying the biologically relevant hydrophobic pocket. However, the high degree of flexibility allowed by a saturated ethylene bridge appeared to allow both rings to occupy their respective pockets. A direct and high-yielding synthetic route to a pyrimidinyl compound with an ethylene linker was developed that incidentally allowed for the preparation of the entire series of TMP analogues of the compositions and methods described herein.

The commercially available diaminopyrimidine 4 could be directly iodinated at the C5 position to give 5-iodopyrimidine-2,4-diamine. Direct conversion to the tolan derivative 5-[(3,4,5-trimethoxyphenyl)ethynyl]pyrimidine-2,4-diamine was achieved through a palladium catalyzed Sonagashira coupling reaction with trimethoxyphenyl acetylene, prepared by Corey-Fuchs extension of the corresponding aldehyde. Catalytic hydrogenation of 5-[(3,4,5-trimethoxyphenyl)ethynyl]pyrimidine-2,4-diamine was next employed to prepare the fully saturated analogue (i.e., 5-[2-(3,4,5-trimethoxyphenyl)ethyl]pyrimidine-2,4-diamine). Interestingly, under standard hydrogenation conditions, the second reduction was found to be quite slow, and the Z-olefinic linker could be isolated and purified. Equilibration to the more thermodynamically stable E-isomer was accomplished by treatment with iodine and allowed easy access to the entire two carbon bridge series. Examination of these extended TMP in standard enzyme inhibition assays revealed that the analogues were inactive. Analogues containing an ethynyl linker or E or Z ethenyl group were expected to show poor activity from the docking studies, but the opposite was expected for the fully saturated derivative. However, the fully saturated ethylene linker did not show good activity.

Example 4

Design and Synthesis of the Propargyl-Linked Series

The failure to obtain active compounds containing an ethynyl linker, an E or Z ethenyl group linker, or an ethylene linker was presumed to be due to a mixture of entropic and conformational effects. While a compound containing an ethylene linker can easily adopt a conformation that allows both aromatic rings to occupy their respective binding pockets, it does so at a significant entropic penalty induced by the organization around the highly flexible linker (there is an increase from two rotatable bonds in TMP to three). The other three compounds in this series (i.e., the ethynyl linker and E or Z ethenyl group linker) have lower internal entropy but cannot reach conformations that are productive for binding. Redesign in this series pointed toward analogues with a limited number of rotatable bonds but more freedom for the two aromatic rings to find appropriate binding pockets. The use of a three-carbon propargylic tether appeared as a potential design, as it maintains the same number of degrees of freedom as TMP but allows the two rings to explore more structural space independent of the other. Docking of the two alternative propargyl-linked structures revealed that attaching the trimethoxyphenyl group to the methylene carbon rather than the alkyne carbon would be preferred. The homologated alkyne derivative (5-ethynyl-1,2,3-trimethoxybenzene) used for the synthesis was prepared in three steps from the commercially available acid (3,4,5-trimethoxyphenyl)acetic acid. Reduction of (3,4,5-trimethoxyphenyl)acetic acid to the alcohol, followed by Dess-Martin oxidation, produced the corresponding aldehyde that was condensed with the Ohira-Bestmann reagent to directly deliver the terminal acetylene 5-ethynyl-1,2,3-trimethoxybenzene. This alkyne was engaged in Sonagashira coupling reactions with the pyrimidinyl derivatives to give the compounds of the compositions and methods described herein. It was found that 5-[3-(3,4,5-trimethoxyphenyl)prop-1-yn-1-yl]pyrimidine-2,4-diamine inhibited ChDHFR with an $IC_{50}$ value better than 100 μM and TgDHFR with an $IC_{50}$ value also better than 100 μM. Extending the phenyl ring appeared to increase interactions with the hydrophobic pocket, specifically with Ile 62 and Leu 67, as predicted. However, the extension of the phenyl also caused a loss of lipophilic interactions with Leu 25, Leu 33, and Phe 36 and created a pocket near the C6 position of the pyrimidine ring. This area is normally occupied by secondary ring fusions in potent inhibitors such as MTX. Further analysis of the docked TMP and 5-[3-(3,4,5-trimethoxyphenyl)prop-1-yn-1-yl]pyrimidine-2,4-diamine also revealed a second empty space near Cys 113 within the binding site.

For docking procedures using Flo98, the active sites of both proteins were defined as all residues with an atom falling within an 11 Å sphere around the cocrystallized ligand. The automatic protomol mapping protocol within Surflex-Dock explored the entire active site and was used for docking purposes. The cocrystallized NADPH was included in the definition of the active site. Libraries of the analogues were docked using Flo98 as discussed previously and also using Surflex-Dock as a Sybyl module. All docking results were checked for correct orientation as defined by the conserved hydrogen bond interactions between the protonated N1 of the 2,4-diaminopyrimidine and Asp 32. The resulting conformational energies were also checked for steric clashes and unrealistic geometries.

Example 5

Analysis and Properties of Compounds

HPLC

Samples (0.1 mg/mL in 14% $CHCl_3$, 10 mM $Na_2HPO_4$, pH 6) were analyzed isocratically (4% $CH_3CN$, 10 mM $Na_2HPO_4$ pH 6, 1.5 mL/min) using a Chrom Tech Chiral-AGP column (4.0 mm×100 mm) and a Beckman Coulter System Gold HPLC with PDA detector.

A combination of Flo98 and Surflex-Dock within the Sybyl environment were used to assess docking scores for methyl substitutions at the 6 position of the pyrimidine ring and propargyl locations on 5-[3-(3,4,5-trimethoxyphenyl)prop-1-yn-1-yl]pyrimidine-2,4-diamine. Flo98 performs a Monte Carlo search for the best docking poses into a flexible target and saves an ensemble of protein: ligand complexes with associated energy scores. Surflex-Dock does not dock into the binding site but rather uses a protomol target that is created by probing the active site with small molecular fragments. Ligands are then fragmented and built into the protomol based on an empirical scoring function that accounts for hydrophobic, polar, repulsive, entropic, and solvation terms.

The docking score of 5-[3-(3,4,5-trimethoxyphenyl)prop-1-yn-1-yl]pyrimidine-2,4-diamine with methyl groups in the two noted pockets was greater than that of the unsubstituted compound 5-[3-(3,4,5-trimethoxyphenyl)prop-1-yn-1-yl]pyrimidine-2,4-diamine. Because Surflex-Dock cannot assess a racemic compound, both the R and S enantiomers of the compound with a methyl at the propargyl position were evaluated. Both appear equally viable upon visual analysis and had many of the same interactions with nearby residues. All complexes presented the 'correct' 2,4-diaminopyrimidine positioning within the binding site, with hydrogen bonds to Val 9, Val 10, Asp 32, and Thr 134.

The propargyl scaffold appeared to be superior to TMP for placing substituents in these pockets as well as for synthetic impact in the conformational distribution while interactions between the C6 substitution and the aryl ring in the propargyl series were computationally shown to not be significant. It proved possible to extend the previous success of the Sonagashira coupling reactions to install substitution at C6 of the extended inhibitors. Cross-coupling of acetylene derivative 5-ethynyl-1,2,3-trimethoxybenzene with the known iodopyrimidine derivative 5-iodo-6-methylpyrimidine-2,4-diamine (prepared from commercially available 2-amino-4-chloro-6-methylpyrimidine by amination and iodination) yielded the C6-methyl derivative (i.e., 6-methyl-5-[3-(3,4,5-trimethoxyphenyl)prop-1-yn-1-yl]pyrimidine-2,4-diamine). As predicted by both visual analysis of the docked compound and the docking scores, this compound showed good against both enzymes with $IC_{50}$ values of better than 100 μM against ChDHFR and TgDHFR, respectively.

The second vacant pocket near residue Cys 113 in ChDHFR was also explored by employing substitutions on the methylene bridge of TMP. C7-methyl TMP (rac) has an $IC_{50}$ value of 340 μM, and C7-ethyl TMP (rac) showed improvement over TMP, with an $IC_{50}$ value of 4 μM. Modifying the propargyl extended scaffold appeared to be a better route for exploiting this pocket, as the substitution would potentially form higher affinity interactions with Cys 113. Three different substituents (methyl, hydroxyl, and methoxy) at the propargylic position were also explored. The new terminal acetylenes for these derivatives were prepared, as racemates, in a straightforward manner. The commercially available trimethoxyacetophenone was homologated to the corresponding aldehyde through Wittig condensation and hydrolysis of the resulting enol ether.

A modified Corey-Fuchs homologation provided the racemic acetylene that was coupled with several iodopyrimidine derivatives (such as 5-iodopyrimidine-2,4-diamine and 5-iodo-6-methylpyrimidine-2,4-diamine) to produce the corresponding analogues. Installation of a hydroxy or methoxy substituent could be accomplished in a straightforward manner from the corresponding aldehyde (i.e., 3,4,5-trimethoxybenzaldehyde). This was converted to the propargyl alcohol through the addition of acetylide, and then standard Sonagashira couplings gave analogues 3-(2,4-diaminopyrimidin-5-yl)-1-(3,4,5-trimethoxyphenyl)prop-2-yn-1-ol and 3-(2,4-diamino-6-methylpyrimidin-5-yl)-1-(3,4,5-trimethoxyphenyl)prop-2-yn-1-ol in high yield. Alternatively, the alcohol can be converted to the corresponding methyl ether (i.e., 1,2,3-trimethoxy-5-(1-methoxyprop-2-yn-1-yl)benzene) under standard conditions and cross-coupled in an analogous manner to deliver pyrimidines 5-[3-methoxy-3-(3,4,5-trimethoxyphenyl)prop-1-yn-1-yl]pyrimidine-2,4-diamine and 5-[3-methoxy-3-(3,4,5-trimethoxyphenyl)prop-1-yn-1-yl]-6-methylpyrimidine-2,4-diamine. Again, as predicted from the docked complexes, the methyl-substituted propargyl compound, 6-methyl-5-[3-(3,4,5-trimethoxyphenyl)but-1-yn-1-yl]pyrimidine-2,4-diamine, exhibited very good potency with $IC_{50}$ values better than 100 μM against ChDHFR and TgDHFR, respectively. The hydroxy- and methoxy-substituted propargyl compounds also exhibited $IC_{50}$ values better than 100 μM. Both of the enantiomers of the doubly methylated derivative 6-methyl-5-[3-(3,4,5-trimethoxyphenyl)but-1-yn-1-yl]pyrimidine-2,4-diamine in ChDHFR and TgDHFR inhibition assays were explored. To accomplish the synthesis of the two enantiomeric analogues, an Evans oxazolidinone mediated asymmetric alkylation was performed (see Scheme III). Addition of two different lithio oxazolidinones to the mixed anhydride derived from acid led to imides 29 and 30 that could be alkylated to produce 31 and 32 with fairly high diastereoselectivity. It was logical to examine the individual isomers at the stereogenic center to determine if one of the enantiomers was more active than the other.

Scheme III

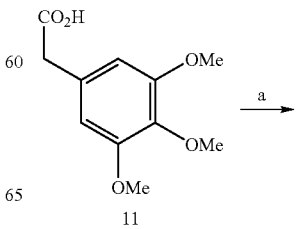

11

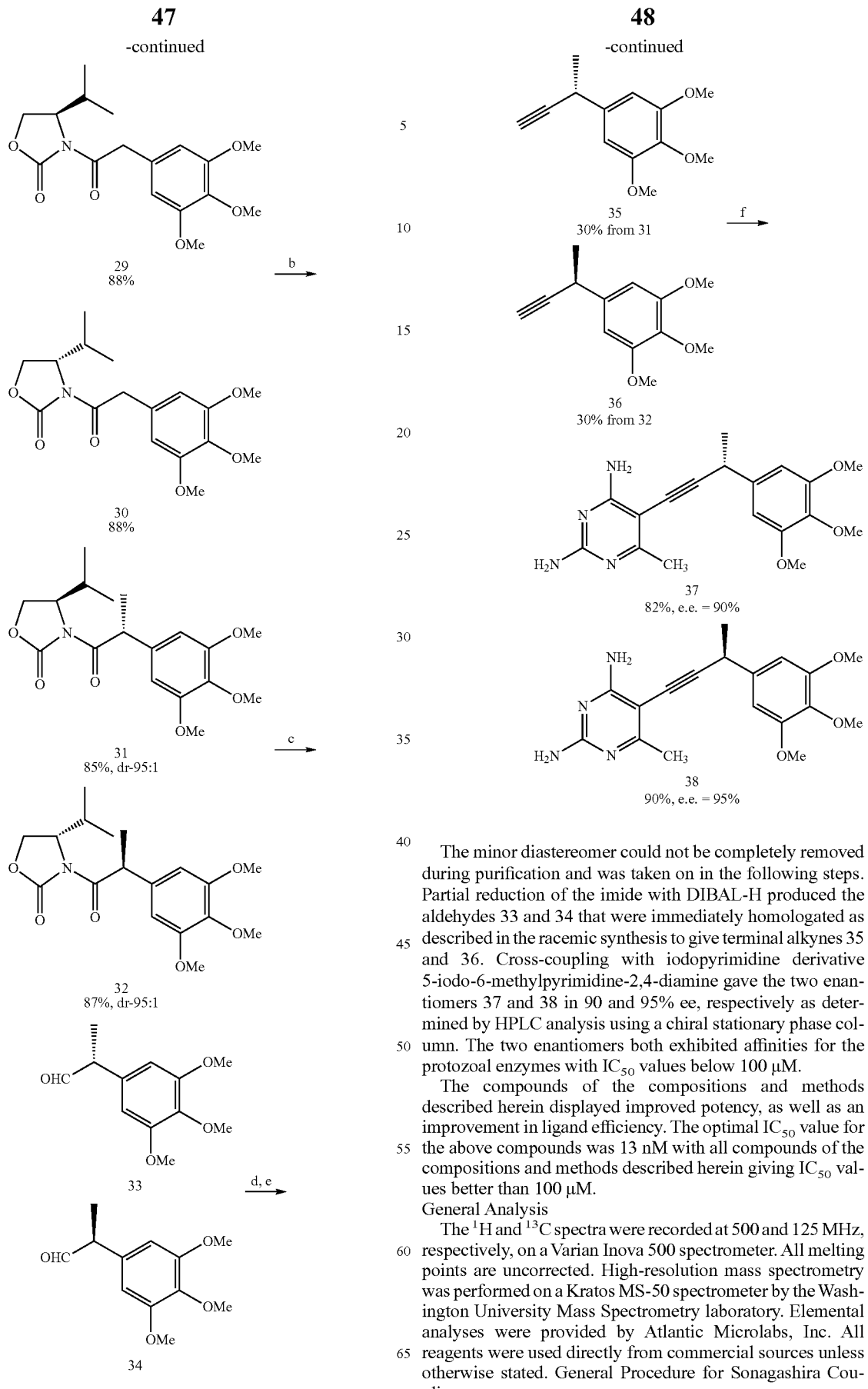

The minor diastereomer could not be completely removed during purification and was taken on in the following steps. Partial reduction of the imide with DIBAL-H produced the aldehydes 33 and 34 that were immediately homologated as described in the racemic synthesis to give terminal alkynes 35 and 36. Cross-coupling with iodopyrimidine derivative 5-iodo-6-methylpyrimidine-2,4-diamine gave the two enantiomers 37 and 38 in 90 and 95% ee, respectively as determined by HPLC analysis using a chiral stationary phase column. The two enantiomers both exhibited affinities for the protozoal enzymes with $IC_{50}$ values below 100 μM.

The compounds of the compositions and methods described herein displayed improved potency, as well as an improvement in ligand efficiency. The optimal $IC_{50}$ value for the above compounds was 13 nM with all compounds of the compositions and methods described herein giving $IC_{50}$ values better than 100 μM.

General Analysis

The $^1$H and $^{13}$C spectra were recorded at 500 and 125 MHz, respectively, on a Varian Inova 500 spectrometer. All melting points are uncorrected. High-resolution mass spectrometry was performed on a Kratos MS-50 spectrometer by the Washington University Mass Spectrometry laboratory. Elemental analyses were provided by Atlantic Microlabs, Inc. All reagents were used directly from commercial sources unless otherwise stated. General Procedure for Sonagashira Couplings To a sealed tube was added the iodopyrimidine (1.0 mmol). DMF (5.0 mL) was added and the mixture stirred until all solids dissolved. Pd—(PPh3)$_2$Cl$_2$ (49.0 mg, 0.07 mmol) was added followed by CuI (13.3 mg, 0.07 mmol), Et$_3$N (5.0 mL), and the aryl acetylene (2.0 mmol). The tube was sealed and placed into a 100° C. oil bath. The reaction was stirred at 100° C. for 2 h and cooled to room temperature. The solvent was removed and the residue purified by flash chromatography (SiO$_2$, 30 g) using 2% MeOH in CHCl$_3$ as the eluent to afford the coupled products. Analytical samples were prepared by recrystallization from MeCN.

2,4-Diamino-5-iodopyrimidine. To a flame-dried 100 mL round-bottom flask was added 2,4-diaminopyrimidine (1.0 g, 9.08 mmol) in MeOH (30 mL) followed by dropwise addition of ICl (30 mL, 29.06 mmol). The solution was stirred at 25° C. for 15 h and then the solvent removed under reduced pressure. The resulting viscous oil was stirred in Et$_2$O (40 mL) for 45 min. The resulting solid was filtered off and washed with Et$_2$O (3×10 mL) to afford the HCl salt as a yellow solid (3.14 g). The crude salt was suspended in 1.0 N NaOH (100 mL) and stirred at 25° C. for 2 h. The solids were filtered, washed with water (2×10 mL), and dried to afford 2,4-Diamino-5-iodopyrimidine as a brown powder (1.71 g, 80%). An analytical sample was prepared by recrystallization from MeCN to give 2,4-Diamino-5-iodopyrimidine as colorless crystals: Rf=0.25 (9:1, CHCl$_3$:MeOH); mp=212-214° C.; $^1$H NMR (DMSO-d6) δ 7.92 (s, 1H), 6.40 (s, 2H), 6.10 (s, 2H); $^{13}$C NMR (DMSO-d6) δ 162.8, 162.7, 162.0, 61.2; HREI[M+] 235.9559 (calculated C$_4$H$_5$IN$_4$: 235.9559); Anal. (C$_4$H$_5$IN$_4$) C, H, N.

5-Ethynyl-1,2,3-trimethoxybenzene. To a flame-dried 50 mL round-bottom flask was added CBr$_4$ (2.54 g, 7.65 mmol). DCM (20 mL) was added and the solution cooled to 0° C. Ph$_3$P (4.01 g, 15.30 mmol) was added and the solution stirred at 0° C. for 15 min. 3,4,5-Trimethoxybenzaldehyde (1.0 g, 5.10 mmol) in DCM (6.0 mL) was added dropwise. The solution was stirred at 0° C. for 5 min. The solvent was removed under reduced pressure, and the resulting oil was filtered through a plug of silica and washed with Hex:EtOAc (9:1, 500 mL; 4:1, 500 mL). The combined organics were concentrated to give the crude dibromo-olefin (2.31 g, 128%), which was dissolved in THF (60 mL) and cooled to −78° C. n-BuLi (13.1 mL, 19.68 mmol, 1.5 M) was added dropwise and the solution stirred at −78° C. for 30 min. Saturated NH$_4$Cl (10 mL) was added and the solution warmed to room temperature. The layers were separated, and the organics were washed with brine (10 mL), dried over anhydrous Na$_2$SO$_4$, and concentrated. The residue was purified by flash chromatography (SiO$_2$, 80 g) using 10% EtOAc in hexanes as the eluent to afford 5-Ethynyl-1,2,3-trimethoxybenzene as a colorless oil (0.770 g, 79%): Rf=0.30 (4:1, Hex:EtOAc); $^1$H NMR (CDCl$_3$) δ 6.71 (s, 2H), 3.84 (s, 3H), 3.83 (s, 6H), 3.03 (s, 1H); $^{13}$C NMR (CDCl$_3$) δ 153.1, 117.1, 109.4, 103.3, 83.8, 76.4, 61.0, 56.2, 56.1; HRFAB[M+Li]199.0952 (calculated C$_{11}$H$_{12}$O$_3$Li: 199.0946).

2,4-Diamino-5-(2-(3,4,5-trimethoxyphenyl)ethynyl)pyrimidine. 2,4-Diamino-5-iodopyrimidine (236 mg) was allowed to react with 5-Ethynyl-1,2,3-trimethoxybenzene (384 mg) as per the general procedure to afford 2,4-Diamino-5-(2-(3,4,5-trimethoxyphenyl)ethynyl)pyrimidine as a white powder (270 mg, 90%): Rf=0.28 (9:1, CHCl$_3$:MeOH); mp=202-204° C.; $^1$H NMR (DMSO-d6) δ 7.94 (s, 1H), 6.90 (s, 2H), 6.37 (s, 2H), 3.79 (s, 6H), 3.67 (s, 3H); $^{13}$C NMR (DMSO-d6) δ 163.4, 162.2, 159.4, 159.2, 152.8, 137.6, 118.6, 108.3, 108.2, 94.7, 89.8, 83.4, 60.2, 60.1, 56.0, 55.9; Anal. (C$_{15}$H$_{16}$N$_4$O$_3$) C, H, N.

(Z)-2,4-Diamino-5-(3,4,5-trimethoxystyryl)pyrimidine. (300 mg, 1.00 mmol) was placed into a 100 mL shaker flask. EtOH (30 mL) was added, and the mixture was swirled until all solids dissolved. 5% Pd/C (50 mg) was added, and the suspension was placed into a hydrogenation apparatus. The reaction was allowed to run at 45 psi H2 for 5 h. The mixture was filtered through Celite and washed with EtOAc (15 mL). The solvent was removed and the residue purified by flash chromatography (SiO$_2$, 30 g) using 5% MeOH in CHCl$_3$ as the eluent to afford (Z)-2,4-Diamino-5-(3,4,5-trimethoxystyryl)pyrimidine as a white powder (100 mg, 33%, 81% borsm) which was recrystallized from MeCN: Rf=0.33 (9:1, CHCl$_3$:MeOH); mp=175-177° C.; $^1$H NMR (acetone-d6) δ 7.69 (s, 1H), 6.63 (s, 2H), 6.47 (d, J) 11.9 Hz, 1H), 6.27 (d, J) 11.9 Hz, 1H), 5.66 (s, 2H), 5.49 (s, 2H), 3.68 (s, 3H), 3.67 (s, 6H); $^{13}$C NMR (CD3OD) δ 163.5, 163.3, 156.2, 154.3, 138.6, 134.0, 133.0, 122.6, 107.3, 106.4, 61.1, 56.4; HRESI[M+H] 303.1446 (calculated C$_{15}$H$_{19}$N$_4$O$_3$: 303.1457).

(E)-2,4-Diamino-5-(3,4,5-trimethoxystyryl)pyrimidine. (45.0 mg, 0.149 mmol) was suspended in dry THF (1.5 mL). I2 (4.0 mg, 0.0149 mmol) was added and the reaction allowed to stir at 23° C. for 30 min after which time all material was in solution. The red solution was diluted with THF (5.0 mL), and saturated Na$_2$S$_2$O$_3$ (1.0 mL) was added. The layers were separated and the organics washed with water (5.0 mL) and brine (5.0 mL) and dried over anhydrous MgSO$_4$. The solvent was removed and the residue purified by flash chromatography (SiO$_2$, 5.0 g) using 5% MeOH in CHCl$_3$ as the eluent to afford (E)-2,4-Diamino-5-(3,4,5-trimethoxystyryl)pyrimidine as a yellow powder (36 mg, 80%) which was recrystallized from MeCN: Rf=0.28 (9:1, CHCl$_3$: MeOH); mp=182-184° C.; $^1$H NMR (acetone-d6) δ 8.09 (s, 1H), 7.07 (d, J) 15.9 Hz, 1H), 6.85 (s, 2H), 6.82 (d, J) 15.9 Hz, 1H), 5.94 (s, 2H), 5.51 (s, 2H), 3.83 (s, 6H), 3.71 (s, 3H); $^{13}$C NMR (CDCl$_3$) δ 161.6, 161.3, 154.7, 153.4, 138.0, 132.9, 129.1, 119.8, 107.0, 103.4, 60.9, 56.1; HRESI[M+H] 303.1446 (calculated C$_{15}$H$_{19}$N$_4$O$_3$: 303.1457).

2,4-Diamino-5-(3,4,5-trimethoxyphenethyl)pyrimidine. (100 mg, 0.333 mmol) was placed into a 100 mL shaker flask. MeOH (20 mL) was added, and the mixture was swirled until the solids dissolved. 10% Pd/C (100 mg) was added, and the suspension was placed into a hydrogenation apparatus. The reaction was allowed to run for 10 h at 50 psi H2. The solid residue was filtered through Celite and washed with methanol (10 mL). The solvent was removed, and the residue was purified by flash chromatography (SiO$_2$, 10 g) using 10% MeOH in CHCl$_3$ as the eluent to afford 2,4-Diamino-5-(3,4,5-trimethoxyphenethyl)pyrimidine as a white powder (88.0 mg, 87%): Rf=0.06 (9:1, CHCl$_3$:MeOH); mp=155-157° C.; $^1$H NMR (DMSO-d6) δ 7.46 (s, 1H), 6.56 (s, 2H), 6.22 (s, 2H), 5.65 (s, 2H), 3.74 (s, 6H), 3.61 (s, 3H), 2.65-2.62 (m, 2H), 2.52-2.49 (m, 2H); $^{13}$C NMR (DMSO-d6) δ 162.3, 162.0, 155.0, 152.6, 137.5, 135.5, 105.8, 105.8, 60.0, 55.6, 35.0, 29.1; Anal. (C$_{15}$H$_{20}$N$_4$O$_3$) C, H, N.

1,2,3-Trimethoxy-5-(prop-2-ynyl)benzene. To a flame dried 1 L flask was added LiAlH$_4$ (3.85 g, 101.4 mmol). Et$_2$O (250 mL) was added and the suspension cooled to 0° C. Trimethoxyphenylacetic acid (15.3 g, 67.6 mmol) in Et$_2$O (50 mL) was added dropwise and the reaction allowed to stir at 0° C. for 1 h. Water (50 mL) was added and the solution warmed to room temperature. The solids were filtered off and washed with Et$_2$O (3×25 mL). The combined organics were washed with brine (25 mL), dried over anhydrous Na$_2$SO$_4$, and concentrated to give the crude alcohol (13.4 g, 93%). The crude alcohol (13.3 g, 62.7 mmol) was dissolved in DCM (125 mL). Dess-Martin periodinane (39.8 g, 94.0 mmol) was added and the reaction stirred at room temperature for 1 h. Saturated NaHCO$_3$:saturated Na$_2$S$_2$O$_3$ (1:1, v:v, 20 mL) was added and the reaction stirred for 30 min. The organic layer was washed with brine (25 mL), dried over anhydrous Na$_2$SO$_4$, and concentrated to give aldehyde 12 (13.1 g, 96%). Spectra were identical to literature values.

The Ohira-Bestmann reagent (15.1 g, 78.6 mmol) was dissolved in MeOH (260 mL) and the reaction cooled to 0° C. 12 (11.0 g, 52.3 mmol) was added followed by K$_2$CO$_3$ (15.9 g, 115.0 mmol). The reaction was allowed to stir at 0° C. for 1 h and warmed to room temperature, and the solids were filtered. The organics were concentrated and the residue purified by flash chromatography (SiO$_2$, 500 g) using 10% EtOAc in hexanes as the eluent to afford 1,2,3-Trimethoxy-5-(prop-2-ynyl)benzene as a colorless oil (5.61 g, 52%): Rf=0.20 (10% EtOAc); $^1$H NMR (CDCl$_3$) δ 6.58 (s, 2H), 3.86 (s, 6H), 3.83 (s, 3H), 3.55 (s, 2H), 2.22 (s, 1H); $^{13}$C (CDCl$_3$) δ 153.28, 136.75, 131.70, 104.89, 81.87, 70.69, 60.80, 56.06, 24.99; HREI[M+]206.0943 (calculated C$_{12}$H$_{14}$O$_3$: 206.0943).

2,4-Diamino-5-(3-(3,4,5-trimethoxyphenyl)prop-1-ynyl) pyrimidine. 2,4-Diamino-5-iodopyrimidine (236 mg) was allowed to react with 1,2,3-Trimethoxy-5-(prop-2-ynyl)benzene (412 mg) as per the general procedure to afford 2,4-Diamino-5-(3-(3,4,5-trimethoxyphenyl)prop-1-ynyl)pyrimidine as a white powder (251 mg, 80%): Rf=0.23 (9:1, CHCl$_3$:MeOH); mp=decomposed above 190° C.; $^1$H NMR (DMSO-d6) δ 7.84 (s, 1H), 6.71 (s, 2H), 6.26 (s, 2H), 3.80 (s, 2H), 3.77 (s, 6H), 3.63 (s, 3H); $^{13}$C NMR (DMSO-d6) δ 163.8, 162.2, 158.7, 152.8, 136.0, 132.8, 105.2, 93.1, 90.1, 76.5, 60.1, 55.8, 25.6; Anal. (C$_{16}$H$_{18}$N$_4$O$_3$) C, H, N.

2,4-Diamino-5-iodo-6-methylpyrimidine. To a 100 mL steel pressure vessel was added 2-amino-4-chloro-6-methylpyrimidine (4.00 g, 28.00 mmol). A saturated solution of NH$_3$ in MeOH (40 mL) was added and the vessel sealed. The pressure vessel was placed into a 160° C. oil bath and heated for 15 h. The vessel was cooled to 0° C. and opened and the solvent removed to give the crude diaminopyrimidine (4.4 g) as the HCl salt. The crude salt was dissolved in MeOH (82.5 mL), and ICl (82.5 mL) was added dropwise over 50 min. The reaction was stirred at 25° C. for 14 h and the solvent removed. The viscous oil was stirred in Et$_2$O (300 mL) for 30 min. The resulting solid was filtered and washed with Et$_2$O (3×20 mL) to give the crude iodinated pyrimidine as a yellow solid (10.1 g). The solids were suspended in 1, 0 N NaOH (300 mL) and stirred at 25° C. for 2 h. The solids were filtered, washed with water (2×20 mL), and allowed to dry to afford 2,4-Diamino-5-iodo-6-methylpyrimidine as a white powder (5.6 g, 80%). An analytical sample was prepared by recrystallization from MeCN to give 2,4-Diamino-5-iodo-6-methylpyrimidine as colorless crystals: Rf=0.25 (9:1, CHCl$_3$: MeOH); mp=154-156° C.; $^1$H NMR (DMSO-d6) δ 6.38 (s, 2H), 6.09 (s, 2H), 2.24 (s, 3H); $^{13}$C NMR (DMSO-d6) δ 166.7, 163.0, 162.3, 63.8, 28.4; HREI[M+]249.9715 (calculated C$_5$H$_7$IN$_4$: 249.9715); Anal. (C$_5$H$_7$IN$_4$) C, H, N.

2,4-Diamino-5-(3-(3,4,5-trimethoxyphenyl)prop-1-ynyl)-6-methylpyrimidine. 2,4-Diamino-5-iodo-6-methylpyrimidine (250 mg) was allowed to react with 1,2,3-Trimethoxy-5-(prop-2-ynyl)benzene (412 mg) as per the general procedure to afford 2,4-Diamino-5-(3-(3,4,5-trimethoxyphenyl)prop-1-ynyl)-6-methylpyrimidine as a white powder (280 mg, 85%): Rf=0.31 (9:1, CHCl$_3$:MeOH); mp=164-166° C.; $^1$H NMR (DMSO-d6) δ 6.72 (s, 2H), 6.42 (s, 2H), 3.85 (s, 2H), 3.76 (s, 6H), 3.63 (s, 3H), 2.24 (s, 3H); $^{13}$C NMR (DMSO-d6) δ 165.0, 164.3, 159.7, 152.8, 135.9, 132.8, 105.0, 96.3, 89.3, 75.8, 60.0, 55.8, 25.7, 21.7; HRFAB[M+Li]335.1679 (calculated C$_{17}$H$_{20}$N$_4$O$_3$Li: 335.1695).

5-(But-3-yn-2-yl)-1,2,3-trimethoxybenzene. To a flame dried 250 mL round-bottom flask was added methoxymethyltriphenylphosphonium bromide (10.28 g, 30.0 mmol). THF (100 mL) was added and the solution cooled to 0° C. n-BuLi (14.0 mL, 30.0 mmol, 2.2 M) was added dropwise and the solution stirred at 0° C. for 30 min. 3,4,5-Trimethoxyacetophenone (5.26 g, 25.0 mmol) in THF (25 mL) was added dropwise. The reaction was stirred at 0° C. for 30 min, and then water (30 mL) was added. The layers were separated, and the aqueous layer was extracted with Et$_2$O (3×20 mL). The combined organics were washed with brine (30 mL), dried over anhydrous Na$_2$SO$_4$, and concentrated. The residue was purified by flash chromatography (SiO$_2$, 50 g) using 5% EtOAc in hexanes as eluent to afford the enol ether (4.35 g, 73%). The enol ether (4.35 g, 18.26 mmol) was dissolved in THF (37.0 mL). Concentrated HCl (3.0 mL) was added and the solution heated to reflux. The solution was stirred at reflux for 3 h and allowed to cool to room temperature. Water (10 mL) was added, and the organics were washed with sat. NaHCO$_3$ (10 mL) and brine (10 mL), dried over anhydrous Na$_2$SO$_4$, and concentrated. The residue was purified by flash chromatography (SiO$_2$, 50 g) using 20% EtOAc in hexanes as the eluent to afford 2-(3,4,5-trimethoxyphenyl)propanal (3.82 g, 93%). Spectra were the identical to literature values CBr$_4$ (8.47 g, 25.55 mmol) was dissolved in DCM (150 mL) and cooled to 0° C. Ph$_3$P (13.4 g, 51.09 mmol) was added and the solution stirred at 0° C. for 5 min. 2-(3,4,5-trimethoxyphenyl)propanal (3.82 g, 17.03 mmol) in DCM (20 mL) was added dropwise. The reaction was stirred at 0° C. for 30 min and then poured into ice-cooled Et$_2$O (500 mL). The solids were filtered through Celite and washed with Et$_2$O (3×50 mL). The combined organics were concentrated. The residue was filtered through a plug of silica and washed with hexanes (100 mL) followed by 10% EtOAc in hexanes (5×100 mL). The combined organics were concentrated to give the intermediate dibromide (4.86 g, 75%) which was used directly for the next reaction. Mg (0.621 g, 25.57 mmol) was suspended in THF (2.0 mL). 1,2-Dibromoethane (0.442 mL, 5.12 mmol) was added and the reaction stirred at 25° C. for 30 min. The dibromide (4.86 g, 12.79 mmol) in THF (11.0 mL) was added dropwise and the solution heated to reflux where it was stirred for 1 h. The solution was cooled to room temperature and the solvent removed. The residue was purified by flash chromatography (SiO$_2$, 150 g) using 10% EtOAc in hexanes as the eluent to afford 5-(But-3-yn-2-yl)-1,2,3-trimethoxybenzene as a colorless oil (1.97 g, 70%): Rf=0.29 (4:1, Hex:EtOAc); $^1$H NMR (CDCl$_3$) δ 6.62 (s, 2H), 3.88 (s, 6H), 3.84 (s, 3H), 3.74-3.69 (m, 1H), 2.29 (d, J) 2.7 Hz, 1H), 1.52 (d, J) 7.1 Hz, 3H); $^{13}$C NMR (CDCl$_3$) δ 153.4, 138.5, 136.9, 104.0, 104.0, 87.2, 70.5, 61.0, 56.3, 32.1, 24.5; HRFAB[M+Li]227.1243 (calculated C$_{13}$H$_{16}$O$_3$Li: 227.1259).

2,4-Diamino-5-(3-(3,4,5-trimethoxyphenyl)but-1-ynyl) pyrimidine. 2,4-Diamino-5-iodopyrimidine (236 mg) was allowed to react with 5-(But-3-yn-2-yl)-1,2,3-trimethoxybenzene (440 mg) as per the general procedure to afford 2,4-Diamino-5-(3-(3,4,5-trimethoxyphenyl)but-1-ynyl)pyrimidine as a yellow powder (295 mg, 90%): Rf=0.29 (9:1, CHCl$_3$:MeOH); mp=220-222° C.; $^1$H NMR (DMSO-d6) δ 7.85 (s, 1H), 6.75 (s, 2H), 6.28 (s, 2H), 3.99 (q, J) 6.8 Hz, 1H), 3.78 (s, 6H), 3.63 (s, 3H), 1.50 (d, J) 7.1 Hz, 3H); $^{13}$C NMR (DMSO-d6) δ 163.7, 152.8, 139.3, 136.0, 104.2, 104.1, 97.9, 76.2, 60.0, 60.0, 55.9, 55.8, 32.3, 24.3; Anal. (C$_{17}$H$_{20}$N$_4$O$_3$) C, H, N.

2,4-Diamino-5-(3-(3,4,5-trimethoxyphenyl)but-1-ynyl)-6-methylpyrimidine. 2,4-Diamino-5-iodo-6-methylpyrimidine (250 mg) was allowed to react with 5-(But-3-yn-2-yl)-1,2,3-trimethoxybenzene (440 mg) as per the general procedure to afford 2,4-Diamino-5-(3-(3,4,5-trimethoxyphenyl)but-1-ynyl)-6-methylpyrimidine as a white powder (294 mg, 86%): Rf=0.29 (9:1, CHCl₃:MeOH); mp=191-193° C.; ¹H NMR (DMSO-d6) δ 6.76 (s, 2H), 6.19 (s, 2H), 4.02 (q, J) 7.1 Hz, 1H), 3.77 (s, 6H), 3.63 (s, 3H), 2.21 (s, 3H), 1.51 (d, J) 7.1 Hz, 3H); ¹³C NMR (DMSO-d6) δ 167.0, 164.1, 161.0, 152.8, 139.4, 136.0, 104.0, 100.8, 88.6, 76.4, 60.0, 55.8, 32.5, 24.6, 22.5; Anal. ($C_{18}H_{22}N_4O_3$) C, H, N.

1-(3,4,5-Trimethoxyphenyl)prop-2-yn-1-ol. To a flame dried 250 mL round-bottom flask was added 3,4,5-trimethoxybenzaldehyde (3.92 g, 20.0 mmol). THF (40 mL) was added and the solution was cooled to 0° C. Ethynylmagnesium bromide (48.0 mL, 24.0 mmol, 0.5 M) was added dropwise. The solution was stirred at 0° C. for 30 min, warmed to 25° C., and stirred for 30 min. Saturated $NH_4Cl$ (5.0 mL) was added, and the layers were separated.

The aqueous layer was extracted with $Et_2O$ (3×5 mL). The combined organics were washed with brine (10 mL), dried over anhydrous $Na_2SO_4$, and concentrated. The residue was purified by flash chromatography ($SiO_2$, 100 g) using 20% EtOAc in hexanes as the eluent to afford 1-(3,4,5-Trimethoxyphenyl)prop-2-yn-1-ol as a yellow oil (4.22 g, 95%): Rf=0.25 (1:1, Hex:EtOAc); ¹H NMR (CDCl₃) δ 6.77 (s, 2H), 5.39 (dd, J) 5.5, 2.0 Hz, 1H), 3.86 (s, 6H), 3.82 (s, 3H), 2.76 (d, J) 5.9 Hz, 1H); ¹³C NMR (CDCl₃) δ 153.4, 138.1, 135.9, 103.7, 83.6, 74.9, 64.5, 61.0, 56.2; HRFAB[M+Li]229.1054 (calculated $C_{12}H_{14}O_4$— Li: 229.1052).

3-(2,4-Diaminopyrimidin-5-yl)-1-(3,4,5-trimethoxyphenyl)-prop-2-yn-1-ol. 2,4-Diamino-5-iodopyrimidine (236 mg) was allowed to react with 1-(3,4,5-Trimethoxyphenyl)prop-2-yn-1-ol (444 mg) as per the general procedure to afford 3-(2,4-Diaminopyrimidin-5-yl)-1-(3,4,5-trimethoxyphenyl)-prop-2-yn-1-ol as a yellow powder (257 mg, 78%): Rf=0.12 (9:1, CHCl₃:MeOH); mp=203-205° C.; ¹H NMR (DMSO-d6) δ 7.84 (s, 1H), 6.83 (s, 2H), 6.34 (s, 2H), 6.01 (d, J) 5.6 Hz, 1H), 5.50 (d, J) 5.4 Hz, 1H), 3.78 (s, 6H), 3.65 (s, 3H); ¹³C NMR (DMSO-d6) δ 163.8, 162.3, 158.2, 152.7, 138.3, 136.7, 109.3, 103.6, 96.3, 79.3, 63.4, 60.0, 55.8; Anal. ($C_{16}H_{18}N_4O_4$) C, H, N.

3-(2,4-Diamino-6-methylpyrimidin-5-yl)-1-(3,4,5-trimethoxyphenyl) prop-2-yn-1-ol. 2,4-Diamino-5-iodo-6-methylpyrimidine (250 mg) was allowed to react with 1-(3,4,5-Trimethoxyphenyl)prop-2-yn-1-ol (444 mg) as per the general procedure to afford 3-(2,4-Diamino-6-methylpyrimidin-5-yl)-1-(3,4,5-trimethoxyphenyl) prop-2-yn-1-ol as a yellow powder (275 mg, 80%): Rf=0.12 (9:1, CHCl₃:MeOH); mp=174-176° C.; ¹H NMR (DMSO-d6) δ 6.85 (s, 2H), 6.27 (s, 2H), 5.98 (d, J) 5.6 Hz, 1H), 5.53 (d, J) 5.4 Hz, 1H), 3.78 (s, 6H), 3.65 (s, 3H), 2.19 (s, 3H), 1.51 (d, J) 7.1 Hz, 3H); ¹³C NMR (DMSO-d6) δ 167.1, 164.3, 161.2, 152.7, 138.3, 136.7, 103.7, 99.1, 87.9, 79.5, 63.6, 60.0, 55.8, 22.5; HRFAB[M+Li]351.1638 (calculated $C_{17}H_{20}N_4O_4Li$: 351.1645).

1,2,3-Trimethoxy-5-(1-methoxyprop-2-ynyl)benzene. To a flame-dried 100 mL round-bottom flask was added NaH (0.240 mg, 6.0 mmol) that had been prewashed with pentane (3×15 mL) and dried. THF (48 mL) was added and the suspension cooled to 0° C. 1-(3,4,5-Trimethoxyphenyl)prop-2-yn-1-ol (1.11 g, 5.0 mmol) in THF (2.0 mL) was added dropwise and the reaction stirred at 0° C. for 25 min. Me2SO4 (0.571 mL, 6.0 mmol) was added and the reaction stirred at 0° C. for 20 min. Water (10 mL) was added, and the layers were separated. The aqueous layer was extracted with $Et_2O$ (20 mL). The combined organics were washed with brine (20 mL), dried over anhydrous $Na_2SO_4$, and concentrated. The residue was purified by flash chromatography ($SiO_2$, 20 g) using 10% EtOAc in hexanes as the eluent to afford 1,2,3-Trimethoxy-5-(1-methoxyprop-2-ynyl)benzene as a colorless oil (1.06 g, 90%): Rf=0.18 (4:1, Hex:EtOAc); ¹H NMR (CDCl₃) δ 6.75 (s, 2H), 5.01 (d, J) 2.2 Hz, 1H), 3.88 (s, 6H), 3.84 (s, 3H), 3.45 (s, 3H), 2.68 (d, J) 2.2 Hz, 1H); ¹³C NMR (CDCl₃) δ 153.4, 138.2, 133.7, 104.4, 81.3, 76.0, 73.1, 61.0, 56.3, 56.2; HRFAB[M+Li]243.1208 (calculated $C_{13}H_{16}O_4Li$: 243.1209).

2,4-Diamino-5-(3-methoxy-3-(3,4,5-trimethoxyphenyl) prop-1-ynyl)pyrimidine. 2,4-Diamino-5-iodopyrimidine (236 mg) was allowed to react with 1,2,3-Trimethoxy-5-(1-methoxyprop-2-ynyl)benzene (473 mg) as per the general procedure to afford 2,4-Diamino-5-(3-methoxy-3-(3,4,5-trimethoxyphenyl)prop-1-ynyl)pyrimidine as an orange powder (310 mg, 90%): Rf=0.31 (9:1, CHCl₃:MeOH); mp=184-186° C.; ¹H NMR (DMSO-d6) δ 7.91 (s, 1H), 6.82 (s, 2H), 6.40 (s, 2H), 5.30 (s, 1H), 3.79 (s, 6H), 3.66 (s, 3H), 3.35 (s, 3H); ¹³C NMR (DMSO-d6) δ 163.8, 162.3, 159.7, 152.8, 137.2, 134.8, 104.6, 92.6, 89.1, 81.9, 73.0, 60.0, 55.9, 55.4; Anal. ($C_{17}H_{20}N_4O_4$) C, H, N.

2,4-Diamino-5-(3-methoxy-3-(3,4,5-trimethoxyphenyl) prop-1-ynyl)-6-methylpyrimidine. 2,4-Diamino-5-iodo-6-methylpyrimidine (250 mg) was allowed to react with 1,2,3-Trimethoxy-5-(1-methoxyprop-2-ynyl)benzene (473 mg) as per the general procedure to afford 2,4-Diamino-5-(3-methoxy-3-(3,4,5-trimethoxyphenyl)prop-1-ynyl)-6-methylpyrimidine as a yellow powder (335 mg, 93%): Rf=0.29 (9:1, CHCl₃:MeOH); mp=127-129° C.; ¹H NMR (DMSO-d6) δ 6.84 (s, 2H), 6.37 (s, 2H), 5.34 (s, 1H), 3.78 (s, 6H), 3.66 (s, 3H), 3.35 (s, 3H), 2.23 (s, 3H); ¹³C NMR (DMSO-d6) δ 167.6, 164.3, 161.1, 152.8, 137.2, 134.8, 104.6, 95.7, 87.5, 81.8, 73.1, 60.0, 55.8, 55.3, 22.4; HRFAB[M+Li]359.1701 (calculated $C_{18}H_{22}N_4O_4Li$: 359.1719). (R)-4-Isopropyl-3-(2-(3,4,5-trimethoxyphenyl)acetyl)oxazolidin-2-one. To a flame-dried 100 mL round-bottom flask was added 3,4,5-trimethoxyphenylacetic acid (2.10 g, 9.29 mmol). THF (25 mL) was added followed by $Et_3N$ (1.42 mL, 10.22 mmol). The solution was cooled to −78° C. Pivaloyl chloride (1.26 mL, 10.22 mmol) was added dropwise and the solution warmed to 0° C. and stirred for 1 h. In a separate flame-dried 50 mL round-bottom flask was added (R)-4-isopropyloxazolidin-2-one (1.0 g). THF (20 mL) was added and the solution cooled to −78° C. n-BuLi (6.83 mL, 9.29 mmol, 1.36 M) was added dropwise and the solution stirred at −78° C. for 15 min and then warmed to 25° C. where it was stirred for 15 min. The organolithium solution was transferred to the solution of the mixed anhydride via cannula at −78° C. The reaction was stirred at −78° C. for 15 min, warmed to 0° C., and stirred for 1 h. Water (10 mL) was added and the aqueous layer extracted with EtOAc (2×10 mL). The combined organics were washed with brine (10 mL), dried over anhydrous $MgSO_4$, and concentrated under reduced pressure. The residue was purified by flash chromatography ($SiO_2$, 30 g) using 25% EtOAc in hexanes as the eluent to afford trimethoxyphenyl)acetyl)oxazolidin-2-one as a colorless oil (2.30 g, 88%): Rf=0.28 (1:1, Hex:EtOAc); ¹H NMR (CDCl₃) δ 6.55 (s, 2H), 4.44-4.41 (m, 1H), 4.29-4.24 (m, 2H), 4.19 (dd, J) 9.0, 3.0 Hz, 1H), 4.12-4.07 (m, 1H), 3.82 (s, 6H), 3.80 (s, 3H), 2.36-2.30 (m, 1H), 0.87 (d, J) 6.8 Hz, 3H), 0.78 (d, J) 7.1 Hz, 3H); ¹³C NMR (CDCl₃) δ 171.2, 154.1, 153.2, 129.4, 106.7, 63.4, 60.9, 58.6, 56.2, 41.6, 28.4, 18.0, 14.7, 14.3; HRFAB[M+Li]344.1686 (calculated $C_{17}H_{23}NO_6Li$: 344.1686).

(S)-4-Isopropyl-3-(2-(3,4,5-trimethoxyphenyl)acetyl)oxazolidin-2-one. (S)-4-Isopropyl-3-(2-(3,4,5-trimethoxyphenyl)acetyl)oxazolidin-2-one was synthesized in an analogous manner as trimethoxyphenyl)acetyl)oxazolidin-2-one using (S)-4-isopropyloxazolidin-2-one. The residue was purified by flash chromatography ($SiO_2$, 30 g) using 25% EtOAc in hexanes as the eluent to afford (S)-4-Isopropyl-3-(2-(3,4,5-trimethoxyphenyl)acetyl)oxazolidin-2-one as a colorless oil (2.30 g, 88%): Rf=0.28 (1:1, Hex:EtOAc); $^1$H NMR (CDCl$_3$) δ 6.54 (s, 2H), 4.44-4.41 (m, 1H), 4.29-4.24 (m, 2H), 4.19 (dd, J) 9.0, 3.0 Hz, 1H), 4.12-4.07 (m, 1H), 3.82 (s, 6H), 3.80 (s, 3H), 2.36-2.30 (m, 1H), 0.87 (d, J) 6.8 Hz, 3H), 0.78 (d, J) 7.1 Hz, 3H); $^{13}$C NMR (CDCl$_3$) δ 171.2, 154.1, 153.2, 129.4, 106.7, 63.4, 60.9, 58.6, 56.2, 41.6, 28.4, 18.0, 14.6, 14.3; HRFAB[M+Li]344.1700 (calculated C$_{17}$H$_{23}$NO$_6$Li: 344.1686).

(R)-3-((R)-2-(3,4,5-trimethoxyphenyl)propanoyl)-4-isopropyloxazolidin-2-one). To a flame-dried 200 mL round-bottom flask was added trimethoxyphenyl)acetyl)oxazolidin-2-one (2.77 g, 8.21 mmol). THF (85 mL) was added and the solution cooled to −78° C. LHMDS (12.5 mL, 12.32 mmol, 1.0 M) was added dropwise, and the reaction was allowed to stir at −78° C. for 1 h. MeI (1.54 mL, 24.63 mmol) was added and the solution stirred at −78° C. for 1 h. The solution was then warmed to 0° C. for 1 h and quenched with sat. NH$_4$Cl (10 mL). The aqueous layer was extracted with EtOAc (2×10 mL). The combined organics were washed with brine (10 mL), dried over anhydrous Na$_2$SO$_4$, and concentrated. The residue was purified by flash chromatography (SiO$_2$, 25 g) using 25% EtOAc in hexanes as the eluent to afford (R)-3-((R)-2-(3,4,5-trimethoxyphenyl)propanoyl)-4-isopropyloxazolidin-2-one) as a colorless oil (2.44 g, 85%, 95:1 d.r): Rf=0.37 (1:1, Hex:EtOAc); $^1$H NMR (CDCl$_3$) δ 6.56 (s, 2H), 5.07 (q, J) 7.1 Hz, 1H), 4.14-4.13 (m, 2H), 3.81 (s, 6H), 3.77 (s, 3H), 2.42-2.36 (m, 1H), 2.12 (s, 1H), 1.47 (d, J) 7.1 Hz, 3H), 0.88 (t, J) 7.1 Hz, 6H); $^{13}$C NMR (CDCl$_3$) δ 174.6, 153.1, 135.8, 105.2, 63.1, 60.8, 59.1, 56.1, 42.8, 28.6, 19.7, 18.0, 14.7; HRFAB[M+Li]358.1852 (calculated C$_{18}$H$_{25}$NO$_6$Li: 358.1842).

(S)-3-((S)-2-(3,4,5-Trimethoxyphenyl)propanoyl)-4-isopropyloxazolidin-2-one. (S)-3-((S)-2-(3,4,5-Trimethoxyphenyl)propanoyl)-4-isopropyloxazolidin-2-one was prepared in an analogous manner as 31. The residue was purified by flash chromatography (SiO$_2$, 25 g) using 25% EtOAc in hexanes as the eluent to afford (S)-3-((S)-2-(3,4,5-Trimethoxyphenyl)propanoyl)-4-isopropyloxazolidin-2-one as a colorless oil (2.08 g, 87%, 95:1 d.r): Rf=0.37 (1:1, Hex: EtOAc); $^1$H NMR (CDCl$_3$) δ 6.58 (s, 2H), 5.09 (q, J) 7.1 Hz, 1H), 4.17-4.15 (m, 2H), 3.83 (s, 6H), 3.80 (s, 3H), 2.45-2.39 (m, 1H), 2.15 (s, 1H), 1.49 (d, J) 7.1 Hz, 3H), 0.90 (t, J) 7.1 Hz, 6H); $^{13}$C NMR (CDCl$_3$) δ 174.7, 153.2, 135.9, 105.3, 63.2, 60.9, 59.2, 56.2, 42.9, 28.6, 19.8, 18.1, 14.8; HRFAB[M+Li] 358.1856 (calculated C$_{18}$H$_{25}$NO$_6$Li: 358.1842).

General Procedure for the Synthesis of R and S 1,2,3-trimethoxy-5-(1-methylprop-2-yn-1-yl)benzene. To a flame dried 200 mL round-bottom flask was added the desired oxazolidinone (1.0 equiv). DCM (0.1 M) was added, and the solution was cooled to −78° C. DIBAL-H (2.0 equiv) was added dropwise, and the reaction was allowed to stir at −78° C. for 2 h. Saturated NH4-Cl (20 mL) was added and the solution warmed to room temperature. The solids were filtered off and washed with DCM (3×5 mL). The aqueous layer was extracted with EtOAc (3×10 mL). The combined organics were washed with brine (10 mL), dried over anhydrous Na$_2$SO$_4$, and concentrated. An NMR measurement of the crude material was taken, and the spectrum matched that for the racemic aldehyde (18). The crude material was used without further purification. CBr4 (1.5 equiv) was dissolved in DCM (0.1 M) and cooled to 0° C. Ph$_3$P (3.0 equiv) was added and the solution stirred at 0° C. for 5 min. The crude aldehyde (1.0 equiv) in DCM (5.0 mL) was added dropwise. The reaction was allowed to stir at 0° C. for 30 min and then poured into ice-cooled Et$_2$O (200 mL). The reaction was filtered through silica gel and washed with hexanes (100 mL) followed by 25% EtOAc in hexanes (300 mL). The organics were combined and concentrated under reduced pressure. The crude material was taken on to the next step without further purification. Mg (2.0 equiv) was suspended in THF (1.0 mL). Dibromoethane (0.4 equiv) was added, and the suspension was stirred at 25° C. for 30 min. The crude dibromide (1.0 equiv) in THF (6.0 mL) was added dropwise, and the reaction was heated at reflux for 30 min. The solution was cooled to room temperature and the solvent removed. The residue was purified by flash chromatography to afford the respective enantioenriched acetylenes. NMR spectra were taken, and the spectra matched that for the racemic acetylene (19).

2,4-Diamino-5-((R)-3-(3,4,5-trimethoxyphenyl)but-1-ynyl)-6-methylpyrimidine. (R)-3-((R)-2-(3,4,5-trimethoxyphenyl)propanoyl)-4-isopropyloxazolidin-2-one) (2.44 g, 6.94 mmol) was subjected to the general procedure to afford R-1,2,3-triilnethoxy-5-(1-methylprop-2-yn-1-yl)benzene (460 mg, 30%). 2,4-Diamino-5-iodo-6-methylpyrimidine (250 mg) was allowed to react with R-1,2,3-trimethoxy-5-(1-methylprop-2-yl)benzene (290 mg) as per the general Sonagashira coupling procedure to afford 2,4-Diamino-5-((R)-3-(3,4,5-trimethoxyphenyl)but-1-ynyl)-6-methylpyrimidine as a brown powder (280 mg, 82%, 90% ee): Rf=0.29 (9:1, CHCl$_3$:MeOH); $^1$H NMR (DMSO-d6) δ 6.76 (s, 2H), 6.19 (s, 2H), 4.02 (q, J) 7.1 Hz, 1H), 3.77 (s, 6H), 3.63 (s, 3H), 2.21 (s, 3H), 1.51 (d, J) 7.1 Hz, 3H); $^{13}$C NMR (DMSO-d6) δ 166.9, 164.1, 160.9, 152.8, 139.4, 135.9, 104.0, 100.7, 88.6, 76.4, 60.0, 55.8, 32.5, 24.7, 22.5; HRFAB[M+Li]349.1851 (calculated C$_{18}$H$_{22}$N$_4$O$_3$Li: 349.1851).

2,4-Diamino-5-((S)-3-(3,4,5-trimethoxyphenyl)but-1-ynyl)-6-methylpyrimidine (38). (S)-3-((S)-2-(3,4,5-Trimethoxyphenyl)propanoyl)-4-isopropyloxazolidin-2-one (1.66 g, 4.72 mmol) was subjected to the general procedure to afford S-1,2,3-trimethoxy-5-(1-methylprop-2-yn-1-yl)benzene (312 mg, 30%). 2,4-Diamino-5-iodo-6-methylpyrimidine (250 mg) was allowed to react with S-1,2,3-trimethoxy-5-(1-methylprop-2-yn-1-yl)benzene (290 mg) as per the general Sonagashira coupling procedure to afford 38 as a yellow powder (308 mg, 90%, 95% ee): Rf=0.29 (9:1, CHCl$_3$: MeOH); $^1$H NMR (DMSO-d6) δ 6.76 (s, 2H), 6.19 (s, 2H), 4.02 (q, J) 7.1 Hz, 1H), 3.77 (s, 6H), 3.63 (s, 3H), 2.21 (s, 3H), 1.51 (d, J) 7.1 Hz, 3H); $^{13}$C NMR (DMSO-d6) δ 167.0, 164.1, 161.0, 152.8, 139.4, 136.0, 104.0, 100.8, 88.6, 76.4, 60.0, 55.8, 32.5, 24.6, 22.5; HRFAB[M+Li]349.1851 (calculated C$_{18}$H$_{22}$N$_4$O$_3$Li: 349.1851).

Example 6

Chemistry and Modeling

Structural Analysis of ChDHFR and hDHFR.

Based on the structure of ChDHFR-TS, a novel series of DHFR inhibitors defined by a propargyl linker between a 2,4-diaminopyrimidine ring and aryl ring were developed. Through these efforts, a highly efficient ligand (compound X) with an inhibition constant (IC$_{50}$) of 38 nM and molecular weight of 342 Da was identified. A series of second generation propargyl analogs inspired by structural analysis that not only maintained high levels of potency against the parasitic enzyme but also exhibited extremely high levels of selectivity were subsequently developed and analyzed.

Analysis of the interactions of biphenyl compounds with ChDHFR.

The docked conformations of both the 5' and 4' series of biphenyl compounds displayed a substantial increase in lipophilic contacts between the ligand and receptor over UCP111A. The results showed that unsubstituted and methyl-substituted analogs in both families are more potent than the initial lead, UCP111A, and are more potent than biphenyl analogs with isopropyl substitutions.

Figures 9A, 9B, 9C:
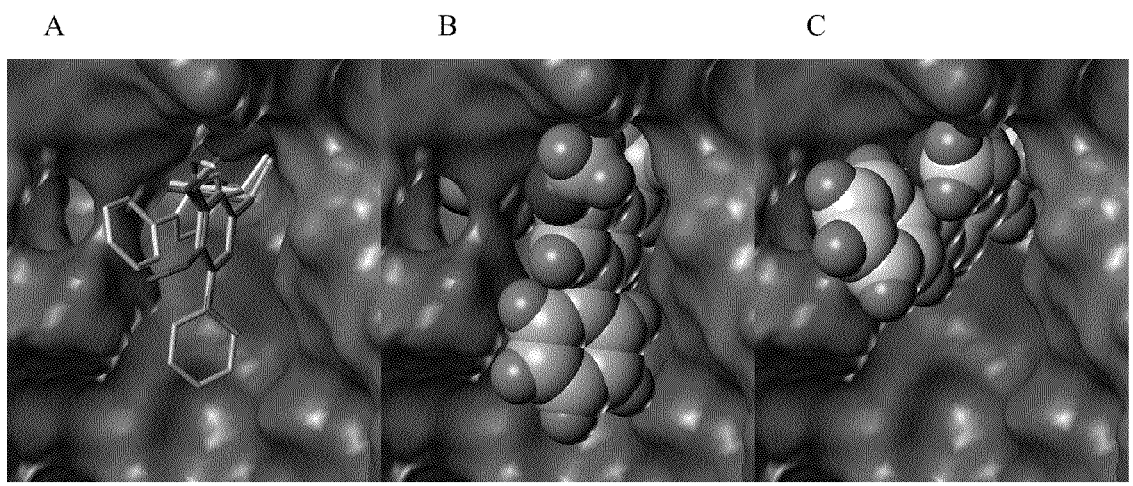

Computational analysis of the compounds docked into ChDHFR explains the clear preference for the 5' substituted compounds as opposed to the 4' substituted compounds. The preferred location of the 3'-OMe on the first biphenyl ring is directed upwards in the active site opening to a pocket formed by Leu 25, Gln 24, Gly 23 and Ser 61, with a hydrogen bonding opportunity using the backbone NH of Leu 25. There is also lipophilic interaction with the alkyl portions of Leu 25 and Gln 24. With the 3'-OMe in the preferred orientation, the second phenyl ring is either projected down in the opening in the 5' series, or directly out of the active site in the 4' series with minimal ChDHFR contacts. As seen in FIG. 9, the region at the opening of the active site is lipophilic, and may have several contacts with the second phenyl in the 5' series, but would have only limited contact with the second phenyl ring in the 4' series.

Interestingly, a docking analysis of the UCP111D enantiomers showed an inverted trend to the ChDHFR assay results. The space around the propargyl substituted region is largely dictated by Ile 62, which does not explore much conformational space across the ensemble but has room to rotate towards the back of the active site. In the crystallized location, the iso-methyl group is projected into the active site, creating a single lipophilic pocket above the residue. In this case, there is only space for the propargyl-methyl to direct into one region above the iso-methyl, thus dictating the wrong stereochemistry. If Ile 62 were rotated towards the back of the active site, there would be sufficient room for the propargyl methyl to be docked in either up or down conformation. To test this theory, Ile 62 was altered using a Lovell dictionary of angles to project back into the pocket. This single structure was used for docking, and showed that the R configuration at the propargylic center was preferred.

Analysis of the interactions of biphenyl compounds with hDHFR.

The biphenyl compounds were docked into human DHFR using the ensemble member with the 'widest' opening at the active site, as defined by comparative measures at several points. This ensemble member averaged 0.25 Å wider than the crystal structure. This structure was chosen as it presented the most available space for bulky substitutions and the most difficult case for achieving selectivity. It also presented an opportunity to explore the potential flexibility of this region.

Figures 10A, 10B, 10C:
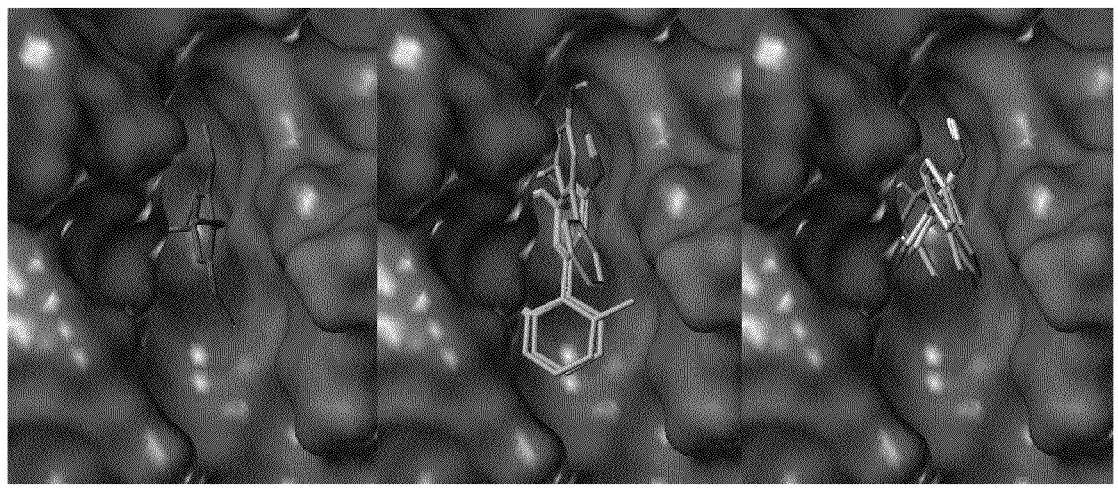

A clear trend was seen in both the docking and assay results for the 5' and 4' series in hDHFR. As seen in FIG. 10, the active site opening in hDHFR is substantially narrower and less lipophilic than ChDHFR. The PEKN loop is projected perpendicularly from the receptor in a disc-like shape, creating a cleft below the loop. This region is readily accessible to the 5'-substituted family as compared to the 4'-substituted family. UCP111D prefers an orientation with the first phenyl located farther up in the pocket than UCP111A, providing equivalent lipophilic contacts. Substituting the second phenyl ring shifts the preference down to the more lipophilic cleft under the ring, yielding a substantial increase in lipophilic contacts. The cleft is a tight fit for the methyl substitutions but is balanced by an increase in lipophilic contacts. These orientations also preserve the 3'-OMe in the ideal "up" location, mimicking the contacts made with UCP111A 3'-OMe.

The 4' series presents a different mode of binding. In order for the pyrimidine and propargyl region of the ligand to be oriented properly, the biphenyl moiety needs to project directly out of the pocket, as with ChDHFR. However, this region is substantially hindered in hDHFR between the PEKN loop and the opposing receptor wall. The orientations in FIG. 10 are the computationally preferred poses, but present substantial steric hindrance. The di-methyl substituted analog (shown in blue) prefers an orientation with the 3'-OMe pointing down in order to limit the steric interference. This orientation also places the propargyl methyl in an orientation farther up in the pocket with fewer contacts, easily accounting for the clear trend in decreasing affinity. Many orientations in the 4' series were explored, but none were found that could take advantage of the cleft below the PEKN loop while preserving the 3'-OMe and propargyl methyl orientation. It is likely that the flexibility of hDHFR that can accommodate the 5' series' increasing steric bulk beneath the PEKN ring does not extend to the regions that the 4' series would project into, or at least not in ways that would accommodate the conformations needed for high affinity.

By probing of flexible space at the active site opening in hDHFR it is evidenta that there is clearly enough flexibility to account for methyl substitutions in the UCP111Dx series, especially in the region around and below the PEKN loop. However, this flexibility is limited, as the loop cannot move enough to accommodate the bulk of the di-isopropyl groups of UCP111D26IPr. It is anticipated that this limited flexibility will be important to account for in future hDHFR design schemes.

Example 7

Biological Evaluation of ChDHFR and hDHFR

All compounds were evaluated in spectrophotometric enzyme assays using ChDHFR-TS and hDHFR. Inhibition constants ($IC_{50}$) were measured (see Table 3). The lead compound, X, has an inhibition constant of 38 nM and modest selectivity (8-fold). All of the biphenyl compounds are more potent than the initial lead compound (X) and exhibit greater selectivity for the pathogenic enzyme. The most potent racemic compound, X, a 5'-biphenyl derivative, is also the most selective of the racemic compounds (944-fold). The single R enantiomer of this 5'-biphenyl analog is the most potent (1.1 nM) and most selective (1273-fold) of all known compounds tested against the *Cryptosporidium* DHFR enzyme. The compound abbreviations in Table 3 refer to the following compounds:

111A: Compound X; D (rac): racemic form of 5-[3-(5-methoxy-biphenyl-3-yl)but-1-yn-1-yl]-6-methylpyrimidine-2,4-diamine; D6M: 5-[3-(5-methoxy-6'-methylbiphenyl-3-yl)but-1-yn-1-yl]-6-methylpyrimidine-2,4-diamine; D26M: 5-[3-(5-methoxy-2'6'-dimethylbiphenyl-3-yl)but-1-yn-1-yl]-6-methylpyrimidine-2,4-diamine; D26I:5-[3-(5-methoxy-2'6'-diisopropylbiphenyl-3-yl)but-1-yn-1-yl]-6-methylpyrimidine-2,4-diamine; F: 5-[3-(3-methoxy-biphenyl-4-yl)but-1-yn-1-yl]-6-methylpyrimidine-2,4-diamine; F2M: 5-[3-(3-methoxy-2'-methylbiphenyl-4-yl)but-1-yn-1-yl]-6-methylpyrimidine-2,4-diamine; F26M: 5-[3-(3-methoxy-2'6'-dimethylbiphenyl-4-yl)but-1-yn-1-yl]-6-methylpyrimidine-2,4-diamine; F26I:5-[3-(3-methoxy-2'6'-diisopropylbiphenyl-4-yl)but-1-yn-1-yl]-6-methylpyrimidine-2,4-diamine; D(R): R—enantiomer of D; and D(S): S—enantiomer of D.

TABLE 3

Inhibitory Potency and Selectivity of DHFR Ligands ($IC_{50}$ values in nM)

| Compound | $IC_{50}$ (ChDHFR) (nM) | $IC_{50}$ (hDHFR) (nM) | Selectivity Ratio ($IC_{50}$ ChDHFR/$IC_{50}$ hDHFR) |
|---|---|---|---|
| 111A | 169 ± 6 | 1380 ± 20 | 8 |
| D (rac) | 1.8 ± n.d. | 1700 ± 10 | 944 |

TABLE 3-continued

Inhibitory Potency and Selectivity
of DHFR Ligands (IC$_{50}$ values in nM)

| Compound | IC$_{50}$ (ChDHFR) (nM) | IC$_{50}$ (hDHFR) (nM) | Selectivity Ratio (IC$_{50}$ ChDHFR/IC$_{50}$ hDHFR) |
|---|---|---|---|
| D6M | 2.1 ± 0.3 | 1360 ± 50 | 648 |
| D26M | 2.1 ± 0.5 | 1250 ± 6 | 595 |
| D26I | 10 ± n.d. | 7200 ± 150 | 720 |
| F | 19 ± 3 | 1420 ± 12 | 75 |
| F2M | 36 ± 0.6 | 2770 ± 59 | 77 |
| F26M | 7.4 ± 1.9 | 3370 ± 15 | 455 |
| F26I | 16 ± n.d. | 4200 ± 0.1 | 262 |
| D (R) | 1.1 ± n.d. | 1360 ± 26 | 1273 |
| D (S) | 30 ± n.d. | 1380 ± 26 | 46 | n.d.—not determined

Example 8

Chemistry and Modeling

Scaffold B of CgDHFR

CgDHFR was incubated with 1.5 mM NADPH and 1 mM compound 11 for two hours at 4° C. Suitable crystals (0.2 mm each side) were grown using the hanging drop vapor diffusion method and by mixing equal volumes of protein:ligand with 0.1 M Tris (pH 8.5), 30% PEG 4000 and 0.2 M MgCl$_2$. Before flash-cooling, the crystals were transferred to a solution containing the crystallization mix and 15% glycerol. All diffraction data were measured at 100 K. The initial data set was measured using an Oxford Excalibur diffractometer and processed using CrysAlis software. The high resolution data set was measured at beamline X25A at Brookhaven National Laboratory using an ADSC CCD detector and processed with HKL2000. Data processing and refinement statistics are reported in Table 4.

TABLE 4

Data collection and refinement statistics

| | |
|---|---|
| Space group | P4$_1$ |
| Unit cell (a, b, c in Å) | a = b = 42.69, c = 230.4, α = 90, β = 90, γ = 120 |
| Resolution (Å) | 40-1.6 |
| Completeness, % (last shell*, %) | 93% (92%) |
| Unique reflections | 47,676 |
| Redundancy (last shell) | 4.7 (2.9) |
| Rsym, % (last shell, %) | 6.8 (38.6) |
| <I/σ> (last shell) | 12.0 (2.5) |
| R-factor/R$_{free}$ (last shell) | 0.19, 0.23 (0.247, 0.303) |
| Average B factor, Å$^2$ | 24.8 |
| Number of atoms (protein, ligands, solvent) | 4,222 |
| No. of nonhydrogen protein atoms | 3684 |
| No. of ligand atoms | 140 |
| No. of solvent molecules | 388 |
| Rms deviation bond lengths (Å), angles (°) | 0.02, 2.2 |

*highest resolution shell: 1.64-1.60 Å

The structure of CgDHFR was resolved by molecular replacement using the program, Phaser, a model of *C. albicans* DHFR (PDB ID: 1M79) as a search probe, and the data obtained on the Oxford system. The molecular replacement solution was used as initial phase information for the high resolution data. Electron density maps were inspected and models were built using Coot. The model was refined using Refmac5 in the CCP4 suite. Water molecules were added automatically using functionality within Coot. The model shows good agreement with the Ramachandran plot (97.3% residues in preferred regions, 2.5% in acceptable regions and 0.2% (1 residue) in a disallowed region. Figures were prepared using Pymol.

Figures 11A, 11B:
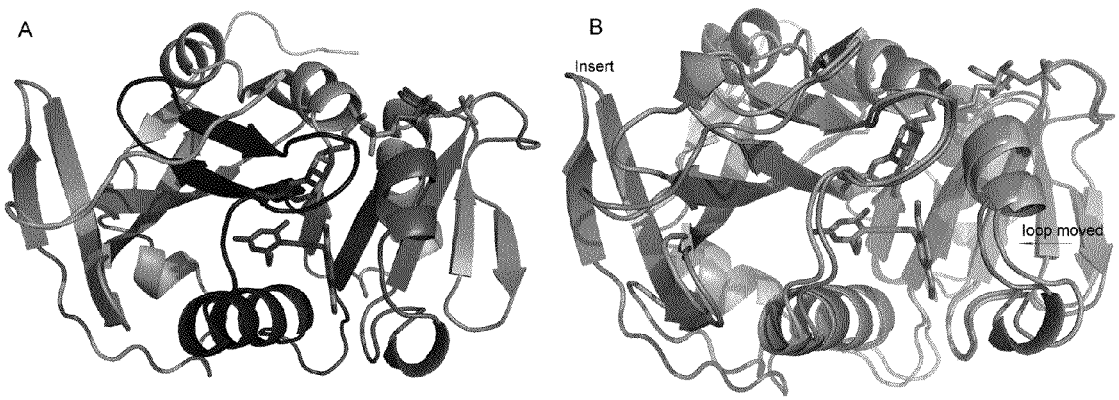

The crystal structure of CgDHFR in complex with compound 11 and NADPH using diffraction amplitudes that extended to 1.6 Å was determined as described above. The crystals belong to the tetragonal space group P4$_1$ and there are two molecules in the asymmetric unit. The overall structure of the 217-residue CgDHFR protein consisted of a ten-strand β-sheet and five flanking alpha helices (FIG. 11a). The eight-residue histidine tag used for purification formed part of the crystal packing interactions and displayed ordered electron density.

CgDHFR and CaDHFR share 85% sequence homology and can be superimposed with an rms deviation of 1.62 Å over the CaDHFR Cα atoms (FIG. 11b). Despite high sequence similarity to CaDHFR, there are several key differences, including a 25-residue insert (residues 177-202 in CgDHFR) that adds two strands to the central beta sheet. There are also two structural differences at the active site: CgDHFR has a methionine (Met 33) interacting with the pyrimidine ring of the inhibitor; CaDHFR has an isoleucine in this position (Ile 33). The loop containing residues 61-66 in CgDHFR is displaced 2.4 Å closer to the active site than the same loop (with residues 61-66) in CaDHFR.

Figures 12A, 12B:
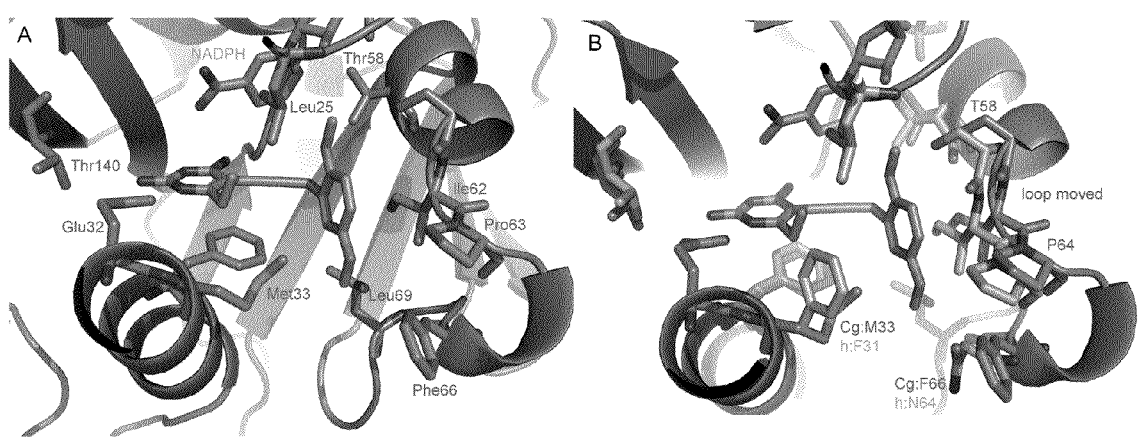

The initial lead, compound 11, is bound in the active site with hydrogen bonds between the pyrimidine ring and Glu 32, Thr 140, Tyr 120, as well as the backbone carbonyl oxygen atoms of Ile 9 and Ile 121 (FIG. 12a). The C6 ethyl group forms limited van der Waals interactions with Met 33 and Phe 36. The acetylinic linker forms van der Waals interactions with the nicotinamide ring of NADPH, Leu 25 and Ile 121. The 2',5'-OMe phenyl ring fits in a hydrophobic pocket comprised of Ile 62, Leu 69, Phe 66, Pro 63 and Thr 58.

The overall fold of CgDHFR is similar to that of human DHFR, however there are several structural differences at the active site (FIG. 12b). There are four residue differences: Met 33 (h:Phe 31) near C6 of the pyrimidine ring, Phe 66 (h:Asn 64) near the aryl ring, Ile 121 (h:Val 115) near the pyrimidine ring and Arg 37 (h:Gln 35) further away at the opening of the active site. The latter two residue differences are farther from the core of the active site. Importantly, the CgDHFR loop comprising residues Thr 58-Phe 66 is displaced 1.2 Å away from the active site, relative to the same loop comprising Thr 56-Asn 64 in hDHFR. The residues in this loop form key interactions with the dimethoxyphenyl ring of the ligand. The modest selectivity (156-fold) of compound 11 potentially results from interactions between the dimethoxyphenyl ring and Met 33 (Phe 31 in hDHFR) or the dimethoxyphenyl ring and the loop containing Ser 59-Pro 61, which is closer to the active site in hDHFR than in CgDHFR and may exhibit some repulsive van der Waals interactions.

Example 9

Chemistry and Modeling

Scaffold A of CgDHFR

In addition to the interactions observed with compounds from scaffold B (Table 2), derivatives of scaffold A also showed potent inhibition and greater antifungal activity. Specifically, docking compound 6 in the CgDHFR structure revealed potential interactions of the propargyl methyl group with a pocket comprised of Ile 121, Thr 58 and Ile 62. The trimethoxyphenyl group presents a 3'-methoxy group to interact with Ser 61 and Leu 25, a 4'-methoxy group that has very few interactions with the protein and a 5'-methoxy group that interacts with Ile 62, Pro 63, Met 33 and distally, Phe 66.

Example 10

Chemistry and Modeling of Second Generation CgDHFR Inhibitors

Several moieties of the first generation inhibitors including a small alkyl group at the C6 position of the pyrimidine ring, the propargyl methyl group of compound 6 and the 3'-methoxy group on the phenyl ring yielded favorable van der Waals interactions with CgDHFR. However, additional interactions, relative to those used by compounds 11 and 6, were available in the ligand binding pocket. It was suspected that larger lipophilic moieties at the 5' position on the aryl ring, relative to the methoxy group of compounds 11 and 6, could take better advantage of the hydrophobic interactions available from Ile 62, Pro 63, Met 33 and Phe 66 (FIG. 13). A bulkier hydrophobic group at this position, designed to increase potency against CgDHFR, was also predicted to decrease potency (and increase selectivity) against hDHFR. The loop containing residues 56-64 in hDHFR is closer to the active site and modeling suggested that it would need to relocate to accommodate steric bulk at the 5' position of a second generation inhibitor.

Therefore, using the structure of CgDHFR and features of compounds 11 and 6, second generation inhibitors were designed to be significantly more potent and selective. The series of second generation derivatives include a methyl group at the C6 position of the pyrimidine, a propargyl methyl group and a phenyl ring at the meta (5') position of the aryl ring while maintaining the 3' methoxy group on the aryl ring (see scaffold in Table 2). In addition to the predicted new interactions with the enzyme, the design of the biphenyl compounds presents a facile route for synthesis. The original propargyl design takes advantage of a key Sonagashira coupling to join an iodinated pyrimidine with an acetylene partner. The synthesis of the biphenyl compounds expands on this modular design to include a Suzuki coupling to install the second aryl ring. Substituents on the second aryl ring were envisioned to project bulk toward the loop region and increase both potency and selectivity, therefore biphenyl derivatives with methyl groups at the meta (compound 12) and para (compound 13) positions on the second ring were synthesized and analyzed (see Table 5).

Example 11

Biological Evaluation of CgDHFR and hDHFR

The second generation compounds were tested in enzyme assays using CgDHFR and human DHFR as well as in antifungal assays. Not only were the compounds found to be extremely potent, with $IC_{50}$ values in the subnanomolar range against DHFR, they also exhibited strong selectivity (2,350-fold) for the fungal enzyme (see Table 5). Significantly, these second generation compounds also displayed superior antifungal activity in vitro with levels of inhibition comparable to clinically used therapeutics.

TABLE 5

Enzyme inhibition and antifungal properties of second generation compounds

| Compound | R | CgDHFR $IC_{50}$ (nM) | hDHFR $IC_{50}$ (nM) | Selectivity (h/CgDHFR) | Antifungal activity MIC (µg/mL) |
|---|---|---|---|---|---|
| 12 | 3', 5' (meta) Me | 0.55 | 750 | 1364 | 3 |
| 13 | 4' (para) Me | 0.6 | 1410 | 2350 | 1.5 |

It should be understood that a plurality of Markush members and provisos have been disclosed above. It is contemplated and therefore within the scope of the compositions and methods described herein that any proviso can be combined with any other proviso enumerated above to give a genus of the compositions and methods described herein. Alternatively, to disclaim any compound disclosed in any of the genera of the compositions and methods described herein, any member of any of the above enumerated Markush groups can be disclaimed to generate a genus.

All scientific articles, publications, abstracts, patents and patent applications mentioned above are hereby incorporated by reference in their entirety.

While this invention has been described in specific detail with reference to the disclosed embodiments, it will be understood that many variations and modifications may be effected within the spirit and scope of the invention.

We claim:

1. A compound of formula I

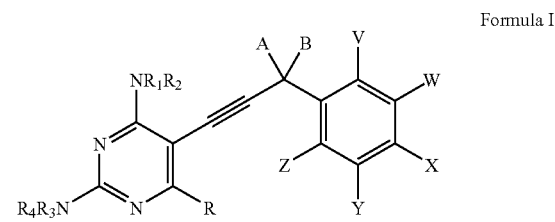

Formula I wherein R is selected from the group consisting of H, $C_{1-5}$-alkyl, $C_{1-3}$-alkoxy, and hydroxy;

wherein $R_1$, $R_2$, $R_3$, and $R_4$ are each independently selected from the group consisting of hydrogen, $C_{1-5}$-alkyl, and cycloalkyl;

wherein A and B are each independently selected from the group consisting of hydrogen, $C_{1-5}$ alkyl, hydroxy, and $C_1$ to $C_6$ alkoxy, provided that at least one of A and B is not $C_{1-5}$ alkyl, or A and B together with the carbon to which they are connected form a ring of from 3 to 7 members wherein the ring members are selected form the group consisting of alkylene, alkenylene, and alkynylene; and wherein V, W, X, Y, and Z are each independently selected from the group consisting of hydrogen, halogen, lower alkoxy, and phenyl, wherein the phenyl substituent may itself be optionally substituted with halogen, lower haloalkyl, lower alkyl, lower alkoxy, or lower alkylsulfonyl, wherein "lower" used in conjunction with any of the above groups is $C_1$ to $C_6$, and at least one of V, W, X, Y, and Z is a methoxy group;

or a pharmaceutically acceptable salt thereof.

2. The compound of claim 1, wherein at least one of W, X, and Y is a methoxy group.

3. The compound of claim 2, wherein all of W, X, and Y are methoxy groups.

4. The compound of claim 1, wherein at least one of V and Y is a methoxy group.

5. The compound of claim 4, wherein both of V and Y are methoxy groups.

6. The compound of claim 1, wherein the compound is selected from the group consisting of 5-[3-(2,5-dimethoxyphenyl)prop-1-yn-1-yl]-6-methylpyrimidine-2,4-diamine;

5-[3-(2,5-dimethoxyphenyl)prop-1-yn-1-yl]pyrimidine-2,4-diamine;

5-[3-(2,5-dimethoxyphenyl)prop-1-yn-1-yl]-6-ethylpyrimidine-2,4-diamine;

5-[3-(3,4,5-trimethoxyphenyl)prop-1-yn-1-yl]pyrimidine-2,4-diamine;

6-methyl-5-[3-(3,4,5-trimethoxyphenyl)prop-1-yn-1-yl]pyrimidine-2,4-diamine;

5-[3-(3,4,5-trimethoxyphenyl)but-1-yn-1-yl]pyrimidine-2,4-diamine;

6-methyl-5-[3-(3,4,5-trimethoxyphenyl)but-1-yn-1-yl]pyrimidine-2,4-diamine;

(R)-6-methyl-5-[3-(3,4,5-trimethoxyphenyl)but-1-yn-1-yl]pyrimidine-2,4-diamine;

(S)-6-methyl-5-[3-(3,4,5-trimethoxyphenyl)but-1-yn-1-yl]pyrimidine-2,4-diamine;

3-(2,4-diaminopyrimidin-5-yl)-1-(3,4,5-trimethoxyphenyl)prop-2-yn-1-ol;

3-(2,4-diamino-6-methylpyrimidin-5-yl)-1-(3,4,5-trimethoxyphenyl)prop-2-yn-1-ol;

5-[3-methoxy-3-(3,4,5-trimethoxyphenyl)prop-1-yn-1-yl]pyrimidine-2,4-diamine;

5-[3-(2,5-dimethoxyphenyl)prop-1-yl-1-yl]-6-propylpyrimidine-2,4-diamine;

6-methlyl-5-[3-(3,4,5-trimethoxyphenyl)pent-1-yn-1-yl]pyrimidine-2,4-diamine;

5-[3-(5-methoxybiphenyl-3-yl)but-1-yn-1-yl]-6-methylpyrimidine-2,4-diamine;

5-[3-(5-methoxy-2'-methylbiphenyl-3-yl)but-1-yn-1-yl]-6-methylpyrimidine-2,4-diamine;

5-[3-(5-methoxy-3',5'-dimethylbiphenyl-3-yl)but-1-yn-1-yl]-6-methylpyrimidine-2,4-diamine;

5-[3-(5-methoxy-4'-methylbiphenyl-3-yl)but-1-yn-1-yl]-6-methylpyrimidine-2,4-diamine;

5-[3-(5-methoxy-2',6'-dimethylbiphenyl-3-yl)but-1-yn-1-yl]-6-methylpyrimidine-2,4-diamine;

5-[3-(3-bromo-5-methoxyphenyl)but-1-yn-1-yl]-6-methylpyrimidine-2,4-diamine;

5-[3-(2,5-dimethoxybiphenyl-3-yl)but-1-yn-1-yl]-6-methylpyrimidine-2,4-diamine; and 5-[3-methoxy-3-(3,4,5-trimethoxyphenyl)prop-1-yn-1-yl]-6-methylpyrimidine-2,4-diamine.

7. A pharmaceutical composition comprising a compound of formula I or a pharmaceutically acceptable salt thereof, according to claim 1 in combination with one or more pharmaceutically acceptable diluents, excipients or carriers.

8. A pharmaceutical composition comprising a compound of formula I or a pharmaceutically acceptable salt thereof, according to claim 6 in combination with one or more pharmaceutically acceptable diluents, excipients or carriers.

9. The compound of claim 1, wherein one of V, W, X, Y, and Z is phenyl, optionally, substituted with halogen, lower haloalkyl, lower alkyl, lower alkoxy, or lower alkylsulfonyl.

10. The compound of claim 1, wherein W is phenyl, optionally, substituted with halogen, lower haloalkyl, lower alkyl, lower alkoxy, or lower alkylsulfonyl, and Y is methoxy.

11. A method of inhibiting dihydrofolate reductase comprising administering a pharmaceutically effective amount of the compound of formula I or a pharmaceutically acceptable salt thereof to an individual in need thereof wherein formula I is

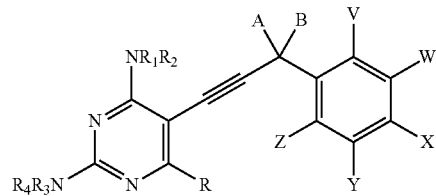

Formula I wherein R is selected from the group consisting of H, $C_{1-5}$ alkyl, $C_{1-3}$ alkoxy, and hydroxy;

wherein $R_1$, $R_2$, $R_3$, and $R_4$ are each independently selected from the group consisting of hydrogen, $C_{i-5}$ alkyl, and cycloalkyl;

wherein A and B are each independently selected from the group consisting of hydrogen, $C_{1-5}$ alkyl, hydroxy, and $C_1$ to $C_6$ alkoxy;, provided that at least one of A and B is not $C_{1-5}$ alkyl, or A and B together with the carbon to which they are connected form a ring of from 3 to 7 members wherein the ring members are selected form the group consisting of alkylene, alkenylene, and alkynylene; and wherein V, W, X, Y, and Z are each independently selected from the group consisting of hydrogen, halogen, lower alkoxy, and phenyl, wherein the phenyl substituent may itself be optionally substituted with halogen, lower haloalkyl, lower alkyl, lower alkoxy, or lower alkylsulfonyl, wherein "lower" used in conjunction with any of the above groups is $C_1$ to $C_6$, and at least one of V, W, X, Y, and Z is a methoxy group.

12. The method of claim 11, wherein at least one of W, X, and Y is a methoxy group.

13. The method of claim 12, wherein all of W, X, and Y are methoxy groups.

14. The method of claim 11, wherein at least one of V and Y is a methoxy group.

15. The method of claim 14, wherein both of V and Y are methoxy groups.

16. A composition comprising the compound of claim 1, and further comprising a sulfa compound.

17. The method of claim 11, further comprising administering a sulfa compound.

* * * * *